United States Patent
Harris et al.

(10) Patent No.: US 8,013,170 B2
(45) Date of Patent: Sep. 6, 2011

(54) SUBSTITUTED PYRROLO[1,2-D][1,4]-DIAZONINES AND TREATMENT OF BRAIN DAMAGE

(76) Inventors: Paul William Richard Harris, Waitakere (NZ); Margaret Anne Brimble, Auckland (NZ)

(*) Notice: Subject to any disclaimer, the term of this patent is extended or adjusted under 35 U.S.C. 154(b) by 833 days.

(21) Appl. No.: 12/002,178

(22) Filed: Dec. 14, 2007

(65) Prior Publication Data

US 2011/0052528 A1   Mar. 3, 2011

Related U.S. Application Data

(62) Division of application No. 10/549,951, filed as application No. PCT/US2004/008108 on Mar. 16, 2004, now Pat. No. 7,485,630.

(60) Provisional application No. 60/456,136, filed on Mar. 20, 2003, provisional application No. 60/505,119, filed on Sep. 23, 2003.

(51) Int. Cl.
*C07D 487/02* (2006.01)
*C07D 491/02* (2006.01)
*C07D 495/02* (2006.01)
*C07D 497/02* (2006.01)

(52) U.S. Cl. ...................................... 548/453

(58) Field of Classification Search .................. 548/453
See application file for complete search history.

(56) References Cited

U.S. PATENT DOCUMENTS

2006/0217295 A1   9/2006   Harris et al.
2006/0258663 A1   11/2006  Brimble

OTHER PUBLICATIONS

Jordan, V. C. Nature Reviews: Drug Discovery, 2, 2003, 205.*
Hackam, et al. JAMA, 296(14), 2006, 1731-1732.*
U.S. Appl. No. 12/421,871, filed Apr. 10, 2009, Bickerdike.
Int'l Preliminary Report, Apr. 23, 2009.
Harris, Paul W.R., et al., "Synthesis of Cyclic Proline-Containing Peptides via Ring-Closing Metathesis", Organic Letters, 2003, vol. 5, No. 11, 1847-1850.
Soave, Rafaella, et al., "Crystal Structure Communications", Organic Compounds, 2002 International Union of Crystallography, C58, 507-509.
European Search Report dated May 5, 2008 (2 pp.).
Belvisi, et al., "Conformational Preferences of Peptides Containing Reverse-Turn Mimetic Bicyclic Lactams: Inverse y-Turns versus Type II B-Turns" Eur.J.Org.Chem. 1999,389-400.
Vippagunta, Sudha, "Crystalline Solids," Advanced Drug Delivery Reviews 48 (2001) 3-26, Elsevier Science BV.
University of Montreal, Canada, Blackwell Munksgaard, 2002.
File history of U.S. Appl. No. 10/549,951, now Patent No. 7,485,630 issued Feb. 3, 2009.

* cited by examiner

*Primary Examiner* — James O Wilson
*Assistant Examiner* — Douglas M Willis
(74) *Attorney, Agent, or Firm* — D. Benjamin Borson; Borson Law Group PC

(57) ABSTRACT

Embodiments of this invention provide novel peptidomimetics that contain a macrocycle, an embodiment of which is 2S,9'S,12'S)-2-{[(1',4'-Diaza-2'-oxobicyclo[7.3.0]dodecyl)-12'-carbonyl]amino}-1,5-pentanedioic acid trifluoroacetate. Such compounds are neuroprotective and have utility as therapeutic agents for treatment of diseases, injuries and other conditions characterized by neuronal degeneration and/or neuronal cell death caused by in embodiments, toxicity or hypoxia. Compounds are also useful for manufacture of medicaments useful for treatment of such conditions.

2 Claims, 3 Drawing Sheets

SUBSTITUTED PYRROLO[1,2-D][1,4]-DIAZONINES AND TREATMENT OF BRAIN DAMAGE

CLAIM OF PRIORITY

This application is a Division of U.S. Utility patent application Ser. No. 10/549,951, which is a 371 of PCT/US04/08108, International filing date Mar. 16, 2004, which claims priority to U.S. Provisional patent application Ser. Nos. 60/456,136, filed Mar. 20, 2003 and Ser. No. 60/505,119, filed Sep. 23, 2003. Each of the aforementioned applications is herein incorporated fully by reference as if separately so incorporated.

FIELD OF THE INVENTION

The present invention relates to novel peptidomimetics containing a macrocycle and methods of their use. This invention also relates to the neuroprotective activity of such compounds. More particularly, this invention relates to the use of these compounds and pharmaceutical compositions thereof in the treatment of diseases and conditions characterised by neuronal degeneration and/or death.

BACKGROUND

The degeneration and/or death of cells in the nervous system is a major factor in many diseases and medical conditions. Such diseases and conditions include traumatic brain injuries, traumatic spinal cord injuries, stroke, hypoxia or ischemia related to decreased neural perfusion secondary to cardiac arterial bypass graft surgery (CABG), Parkinson's disease, Alzheimer's disease, multiple sclerosis, amyotrophic lateral sclerosis and other neurodegenerative diseases. It is of interest to prevent or decrease such cell death and degeneration and to minimize the loss of neural function.

Certain compounds are useful as neuroprotective agents. One such compound is insulin-like growth factor 1 (IGF-1) (Scheepens et al, WO00/13650). IGF-1 is a naturally occurring peptide that can decrease the binding of glutamate to the glutamate receptors of neurons (Bourguinon, U.S. Pat. No. 5,804,550). IGF-1 can also decrease neuronal degradation caused by damage and disease. IGF-1 is cleaved by proteolysis in vivo to give $des_{1-3}$ IGF-1 and the N-terminal tripeptide Gly-Pro-Glu (GPE). GPE and analogues have been found to be neuroprotective (Gluckman et al, U.S. Pat. No. 6,187,906 incorporated herein by reference).

However, such peptides may not be ideal for the treatment of neural death and degeneration especially in conditions in which they are rapidly metabolised in vivo. There is a need for compounds that have neuroprotective and neuroregenerative properties and that are more metabolically stable, especially to enzymatic degradation.

The use of peptidomimetics to mimic the behaviour of biologically active peptides is common in the pursuit of a drug candidate. Peptidomimetics that are more metabolically stable and protease resistant than peptides are desirable, and they often adopt well-defined conformations. Cyclic structures can provide a rigid geometry that can be used to probe the bioactive conformation of a given peptide. This rigidity conformationally restricts the molecule and thus provides a method to design molecules with enhanced biological activity.

SUMMARY

Aspects of this invention include novel cyclic peptidomimetics that can mimic certain properties of the tripeptide Gly-Pro-Glu (GPE). Certain aspects of the invention include molecules having the structural formulae and substituents described below:

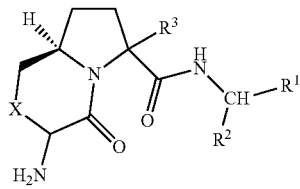

Formula 1

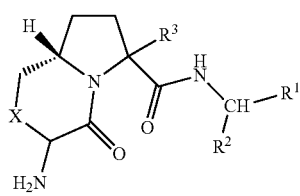

Formula 2

In certain embodiments, compounds of Formula 1 and Formula 2 include substituents where:

$R^1$ and $R^2$ are independently selected from the group consisting of —OR', —SR', —NR'R', —NO$_2$, —CN, —C(O)R', —C(O)OR', —C(O)NR'R', —C(NR')NR'R', trihalomethyl, halogen, alkyl, substituted alkyl, heteroalkyl, substituted heteroalkyl, alkenyl, substituted alkenyl, alkynyl, substituted alkynyl, aryl, substituted aryl, heteroaryl, substituted heteroaryl, arylalkyl, substituted arylalkyl, heteroarylalkyl and substituted heteroarylalkyl; each $R^1$ is independently selected from the group consisting of —H, alkyl, heteroalkyl, alkenyl, alkynyl, aryl, arylalkyl, heteroaryl and heteroarylalkyl and;

$R^3$ is selected from the group consisting of —H, —OR', —SR', —NR'R', —NO$_2$, —CN, —C(O)R', —C(O)OR', —C(O)NR'R', —C(NR')NR'R', trihalomethyl, halogen, alkyl, substituted alkyl, heteroalkyl, substituted heteroalkyl, alkenyl, substituted alkenyl, alkynyl, substituted alkynyl, aryl, substituted aryl, heteroaryl, substituted heteroaryl, arylalkyl, substituted arylalkyl, heteroarylalkyl and substituted heteroarylalkyl; each $R^1$ is independently selected from the group consisting of —H, alkyl, heteroalkyl, alkenyl, alkynyl, aryl, arylalkyl, heteroaryl and heteroarylalkyl and;

X is a linear alkyl or alkenyl chain of $C_0$-$C_3$.

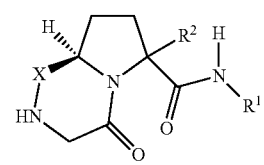

Formula 3

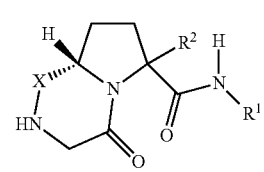

Formula 4

In other embodiments, compounds of Formula 3 and Formula 4 include substituents where:

$R^1$ and $R^2$ are independently selected from the group consisting of —H, —OR', —SR', —NR'R', —NO$_2$, —CN, —C(O)R', —C(O)OR', —C(O)NR'R', —C(NR')NR'R', trihalomethyl, halogen, alkyl, substituted alkyl, heteroalkyl, substituted heteroalkyl, alkenyl, substituted alkenyl, alkynyl, substituted alkynyl, aryl, substituted aryl, heteroaryl, substituted heteroaryl, arylalkyl, substituted arylalkyl, heteroarylalkyl and substituted heteroarylalkyl; each $R^1$ is independently selected from the group consisting of —H, alkyl, heteroalkyl, alkenyl, alkynyl, aryl, arylalkyl, heteroaryl and heteroarylalkyl and;

X is a linear alkyl or alkenyl chain of $C_0$-$C_4$.

Formula 5

Formula 6

In other embodiments, compounds of Formula 5 and Formula 6 include substituents where:

R is independently selected from the group consisting of —H, —OR', —SR', —NR'R', —NO$_2$, —CN, —C(O)R', —C(O)OR', —C(O)NR'R', —C(NR')NR'R', trihalomethyl, halogen, alkyl, substituted alkyl, heteroalkyl, substituted heteroalkyl, alkenyl, substituted alkenyl, alkynyl, substituted alkynyl, aryl, substituted aryl, heteroaryl, substituted heteroaryl, arylalkyl, substituted arylalkyl, heteroarylalkyl and substituted heteroarylalkyl; each $R^1$ is independently selected from the group consisting of —H, alkyl, heteroalkyl, alkenyl, alkynyl, aryl, arylalkyl, heteroaryl and heteroarylalkyl and;

X is a linear alkyl or alkenyl chain of $C_0$-$C_4$.

Formula 7

Formula 8

In other embodiments, compounds of Formula 7 and Formula 8 include substituents where:

R is independently selected from the group consisting of —H, —OR', —SR', —NR'R', —NO$_2$, —CN, —C(O)R', —C(O)OR', —C(O)NR'R', —C(NR')NR'R', trihalomethyl, halogen, alkyl, substituted alkyl, heteroalkyl, substituted heteroalkyl, alkenyl, substituted alkenyl, alkynyl, substituted alkynyl, aryl, substituted aryl, heteroaryl, substituted heteroaryl, arylalkyl, substituted arylalkyl, heteroarylalkyl and substituted heteroarylalkyl; each $R^1$ is independently selected from the group consisting of —H, alkyl, heteroalkyl, alkenyl, alkynyl, aryl, arylalkyl, heteroaryl and heteroarylalkyl.

Other aspects of the invention provide pharmaceutically acceptable salts of the compounds described in formulas 1-8.

In still other aspects, this invention provides pharmaceutical compositions comprising a pharmaceutically acceptable excipient and a therapeutically effective amount of at least one compound of this invention. These compositions find use as anti-apoptotic and anti-necrotic agents and for other conditions involving neural degeneration or injury.

In yet further aspects, this invention provides a method of treating an animal having a disease or injury capable of treatment by administration of a suitable compound, comprising administration to that animal of at least one compound of this invention, optionally in conjunction with at least one other conventional therapeutic agent for the disease being treated.

In still further aspects the animal to be treated is a human.

In still further aspects, this invention provides methods of preparing the compounds of Formulas 1-8 of this invention.

In yet other aspects, this invention provides methods of synthesising, formulating and preparing pharmaceutical preparations comprising compounds of Formulas 1-8 of this invention.

DETAILED DESCRIPTION OF THE INVENTION

Definitions

Figure 1:
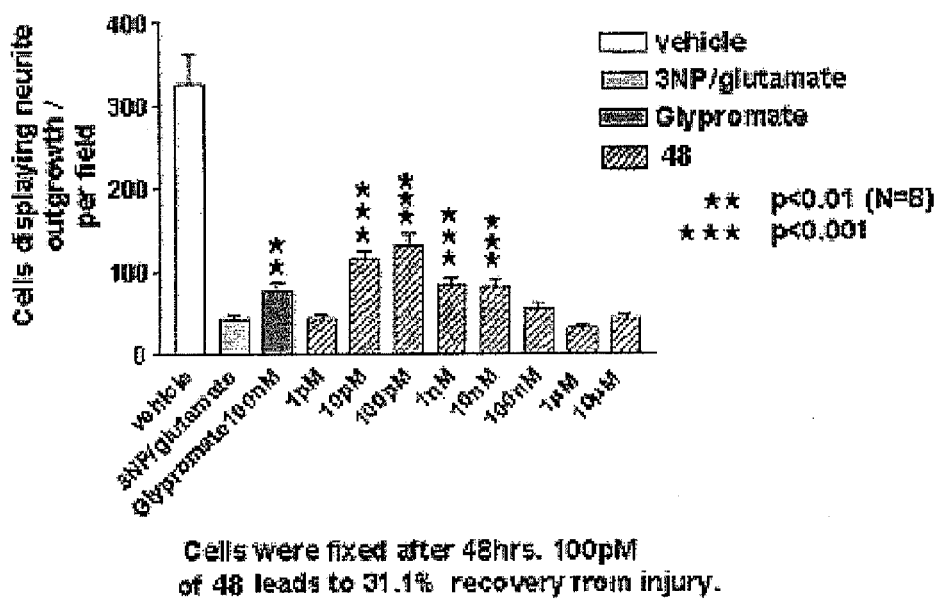
FIG. 1 is a graph showing effects of (2S, 3'S, 8'R, 11'S) 2-{[(3'-Amino-1'-aza-2'-oxobicyclo[6.3.0]-undecyl)-11'-carbonyl]amino}-1,5-pentanedioic acid trifluoroacetate salt 48 on neuronal survival in animals following excitotoxic oxidative stress.

"Alkenyl" refers to an unsaturated branched, straight chain or cyclic hydrocarbon radical having at least one carbon-carbon double bond. The radical can be in either the cis or trans conformation about the double bond(s). Exemplary alkenyl groups include allyl, ethenyl, propenyl, isopropenyl, butenyl, isobutenyl, cyclopentenyl and the like. In some embodiments the alkenyl groups are ($C_2$-$C_6$) alkenyl and in other embodiments allyl can be particularly useful.

"Alkyl" refers to a saturated branched, straight chain or cyclic hydrocarbon radical. Exemplary alkyl groups include methyl, ethyl, isopropyl, cyclopropyl, tert-butyl, cyclopropylmethyl, hexyl and the like. In some embodiments the alkyl groups are ($C_1$-$C_6$) alkyl.

"Alkynyl" refers to an unsaturated branched, straight chain or cyclic hydrocarbon radical having at least one carbon-carbon triple bond. Exemplary alkynyl groups include ethynyl, propynyl, butynyl, isobutynyl and the like. In some embodiments the alkynyl group is ($C_2$-$C_6$) alkynyl.

"Aryl" refers to an unsaturated cyclic hydrocarbon radical with a conjugated π electron system. Exemplary aryl groups include phenyl, naphthyl and the like. In some embodiments the aryl group is ($C_5$-$C_{20}$) aryl.

"Arylalkyl" refers to a straight chain alkyl, alkenyl or alkynyl group wherein one of the hydrogen atoms bonded to the terminal carbon is replaced with an aryl group. Exemplary arylalkyl groups include benzyl, naphthylmethyl, benzylidene and the like.

A "growth factor" refers to an extracellular polypeptide-signalling molecule that stimulates a cell to grow or proliferate.

"Heteroalkyl" refers to an alkyl moiety wherein one or more carbon atoms are replaced with another atom such as N, P, O, S etc. Exemplary heteroalkyl groups include pyrrolidine, morpholine, piperidine, piperazine, imidazolidine, pyrazolidine, terahydrofuran, ($C_1$-$C_{10}$) substituted amines, ($C_2$-$C_6$) thioethers and the like.

"Heteroaryl" refers to an aryl moiety wherein one or more carbon atoms are replaced with another atom such as N, P, O, S etc. Exemplary heteroaryl groups include carbazole, furan, imidazole, indazole, indole, isoquinoline, purine, pyrazine, pyrazole, pyridazine, pyridine, pyrrole, thiazole, thiophene, triazole and the like.

"Injury" includes any acute or chronic damage of an animal that results in degeneration or death of cells in the nervous system or results in loss of function. Such cells include neuronal cells and non-neuronal cells. Injury includes stroke, non-hemorrhagic stroke, traumatic brain injury, perinatal asphyxia associated with fetal distress such as following abruption, cord occlusion or associated with intrauterine growth retardation, perinatal asphyxia associated with failure of adequate resuscitation or respiration, severe CNS insults associated with near miss drowning, near miss cot death, carbon monoxide inhalation, ammonia or other gaseous intoxication, cardiac arrest, coma, meningitis, hypoglycemia and status epilepticus, episodes of cerebral asphyxia associated with coronary bypass surgery, hypotensive episodes and hypertensive crises, and cerebral trauma. It is to be understood that the above examples are by way of illustration only, and are not intended to be a complete listing of injuries capable of being treated by the compounds and methods of this invention.

A "pharmaceutically acceptable excipient" refers to an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

A "pharmaceutically acceptable salt" refers to a salt that is pharmaceutically acceptable and has the desired pharmacological properties. Such salts include salts that can be formed where acidic protons present in the compounds are capable of reacting with inorganic or organic bases. Suitable inorganic salts include those formed with the alkali metals, e.g. sodium and potassium, magnesium, calcium, and aluminium. Suitable organic salts include those formed with organic bases such as the amine bases e.g. ethanolamine, diethanolamine, triethanolamine, tromethamine, N-methylglucamine, and the like. Such salts also include acid addition salts formed with inorganic acids (e.g. hydrochloric and hydrobromic acids) and organic acids (e.g. acetic acid, citric acid, maleic acid, and the alkane- and arene-sulfonic acids such as methanesulfonic acid and benzenesulfonic acid). When there are two acidic groups present, a pharmaceutically acceptable salt can be a mono-acid mono-salt or a di-salt; and similarly where there are more than two acidic groups present, some or all of such groups can be salified.

A "protecting group" has the meaning conventionally associated with it in organic synthesis, i.e. a group that selectively blocks one or more reactive sites in a multifunctional compound such that a chemical reaction can be carried out selectively on another unprotected reactive site and such that the group can readily be removed after the selective reaction is complete.

"Substituted" refers to where one or more of the hydrogen atoms on an alkyl, heteroalkyl, alkenyl, alkynyl, aryl, heteroaryl or arylalkyl radical are independently replaced with another substituent. Substituents include —R', —OR', —SR', —NR'R', —NO$_2$, —CN, —C(O)R', —C(O)OR', —C(O)NR'R', —C(NR')NR'R', —NR'—C(NR')—OR', —NR'—C(NR')—SR', NR'—C(NR')—NR'R', trihalomethyl and halogen where each $R^1$ is independently —H, alkyl, heteroalkyl, alkenyl, alkynyl, aryl, arylalkyl, heteroaryl or heteroarylalkyl.

A "therapeutically effective amount" means the amount that, when administered to an animal for treating a disease, is sufficient to effect treatment for that disease; that is, an amount that decreases adverse symptoms or findings, promotes desirable symptoms or findings, and/or treats an underlying disorder, and/or is curative.

"Treating" or "treatment" of a disease includes preventing the disease from occurring in an animal that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease).

Implicit hydrogen atoms (such as the hydrogens on the pyrrole ring, etc.) are omitted from the formulae for clarity, but should be understood to be present.

Compounds of the Invention

Certain aspects of the invention provide molecules having the structural formulae and substituents described below:

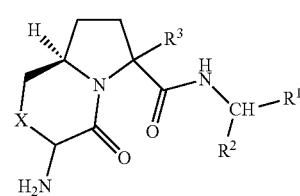

Formula 1

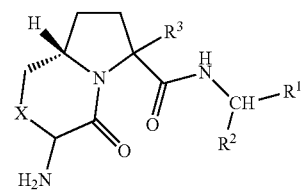

Formula 2

In certain embodiments, compounds of Formula 1 and Formula 2 include substituents where:

$R^1$ and $R^2$ are independently selected from the group consisting of —OR', —SR', —NR'R', —NO$_2$, —CN, —C(O)R', —C(O)OR', —C(O)NR'R', —C(NR')NR'R', trihalomethyl, halogen, alkyl, substituted alkyl, heteroalkyl, substituted heteroalkyl, alkenyl, substituted alkenyl, alkynyl, substituted alkynyl, aryl, substituted aryl, heteroaryl, substituted heteroaryl, arylalkyl, substituted arylalkyl, heteroarylalkyl and substituted heteroarylalkyl; each $R^1$ is independently selected from the group consisting of —H, alkyl, heteroalkyl, alkenyl, alkynyl, aryl, arylalkyl, heteroaryl and heteroarylalkyl and;

$R^3$ is selected from the group consisting of —H, —OR', —SR', —NR'R', —NO$_2$, —CN, C(O)R', —C(O)OR', —C(O)NR'R', —C(NR')NR'R', trihalomethyl, halogen, alkyl, substituted alkyl, heteroalkyl, substituted heteroalkyl, alkenyl, substituted alkenyl, alkynyl, substituted alkynyl, aryl, substituted aryl, heteroaryl, substituted heteroaryl, arylalkyl, substituted arylalkyl, heteroarylalkyl and substituted heteroarylalkyl; each $R^1$ is independently selected from the group consisting of —H, alkyl, heteroalkyl, alkenyl, alkynyl, aryl, arylalkyl, heteroaryl and heteroarylalkyl and;

X is a linear alkyl or alkenyl chain of $C_0$-$C_3$.

In further embodiments of the invention the compounds are compounds of Formula 1 where $R^1$=—COOH; $R^2$=—(CH$_2$)$_2$—COOH; $R^3$=H; X=—(CH$_2$)$_3$—

In other embodiments of the invention the compounds are compounds of Formula 1 where $R^1$=—COOH; $R^2$=—(CH$_2$)$_2$—COOH; $R^3$=—CH$_3$; X=—(CH$_2$)$_3$—

In still other embodiments of the invention the compounds are compounds of formula 1 where $R^1$=—COOH; $R^2$=—(CH$_2$)$_2$—COOH; $R^3$=allyl; X=-(CH$_2$)$_3$—

In yet further embodiments of the invention the compounds are compounds of formula 1 where $R^1$=—COOH; $R^2$=—(CH$_2$)$_2$—CH$_3$; $R^3$=H; X=—(CH$_2$)$_3$—

In still other embodiments of the invention the compounds are compounds of formula 1 where $R^1$=—COOH; $R^2$=—(CH$_2$)$_2$—COOH; $R^3$=H; X=—(CH$_2$)$_2$—

In further embodiments of the invention the compounds are compounds of formula 1 where $R^1$=—COOH; $R^2$=—(CH$_2$)$_2$—COOH; $R^3$=H; X=—CH$_2$—CH=CH—, (where the CH$_2$ of X is adjacent to the carbon attached to the NH$_2$ group).

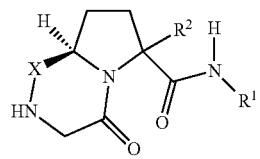

Formula 3

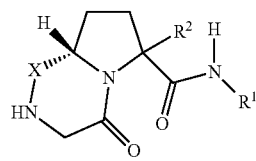

Formula 4

In other embodiments, compounds of Formula 3 and Formula 4 include substituents where:

$R^1$ and $R^2$ are independently selected from the group consisting of —H, —OR', —SR', —NR'R', —NO$_2$, —CN, —C(O)R', —C(O)OR', —C(O)NR'R', —C(NR')NR'R', trihalomethyl, halogen, alkyl, substituted alkyl, heteroalkyl, substituted heteroalkyl, alkenyl, substituted alkenyl, alkynyl, substituted alkynyl, aryl, substituted aryl, heteroaryl, substituted heteroaryl, arylalkyl, substituted arylalkyl, heteroarylalkyl and substituted heteroarylalkyl; each $R^1$ is independently selected from the group consisting of —H, alkyl, heteroalkyl, alkenyl, alkynyl, aryl, arylalkyl, heteroaryl and heteroarylalkyl and;

X is a linear alkyl or alkenyl chain of $C_0$-$C_4$.

In further embodiments of the invention the compounds are compounds of formula 3 where $R^1$=—CH(COOH)—(CH$_2$)$_2$—COOH; $R^2$=H; X=—(CH$_2$)$_4$—

In still other embodiments of the invention the compounds are compounds of formula 3 where $R^1$=—CH(COOH)—(CH$_2$)$_2$—COOH; $R^2$=CH$_3$; X=—(CH$_2$)$_4$—

In yet further embodiments of the invention the compounds are compounds of formula 3 where $R^1$=—CH(COOH)—(CH$_2$)$_2$—COOH; $R^2$=allyl; X=—(CH$_2$)$_4$—

In further embodiments of the invention the compounds are compounds of formula 3 where $R^1$=—CH(COOH)—(CH$_2$)$_2$—CH$_3$; $R^2$=H; X=—(CH$_2$)$_4$—

In other embodiments of the invention the compounds are compounds of formula 3 where $R^1$=—CH(COOH)—(CH$_2$)$_2$—COOH; $R^2$=H; X=—(CH$_2$)$_3$—

In still other embodiments of the invention the compounds are compounds of formula 3 where $R^1$=—CH(COOH)—(CH$_2$)$_2$—COOH; $R^2$=H; X=—CH$_2$—CH=CH—CH$_2$—

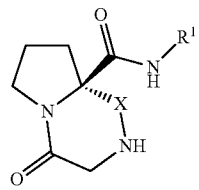

Formula 5

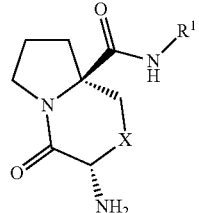

Formula 6

In other embodiments, compounds of Formula 5 and Formula 6 include substituents where:

R is independently selected from the group consisting of —H, —OR', —SR', —NR'R', —NO$_2$, —CN, —C(O)R', —C(O)OR', —C(O)NR'R', —C(NR')NR'R', trihalomethyl, halogen, alkyl, substituted alkyl, heteroalkyl, substituted heteroalkyl, alkenyl, substituted alkenyl, alkynyl, substituted alkynyl, aryl, substituted aryl, heteroaryl, substituted heteroaryl, arylalkyl, substituted arylalkyl, heteroarylalkyl and substituted heteroarylalkyl; each $R^1$ is independently selected from the group consisting of —H, alkyl, heteroalkyl, alkenyl, alkynyl, aryl, arylalkyl, heteroaryl and heteroarylalkyl and;

X is a linear alkyl or alkenyl chain of $C_0$-$C_4$.

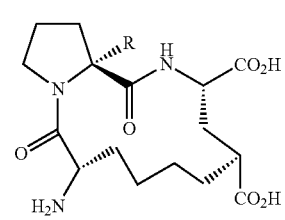

Formula 7

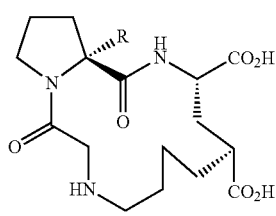

Formula 8

In other embodiments, compounds of Formula 7 and Formula 8 include substituents where:

R is independently selected from the group consisting of —H, —OR', —SR', —NR'R', —NO$_2$, —CN, —C(O)R', —C(O)OR', —C(O)NR'R', —C(NR')NR'R', trihalomethyl, halogen, alkyl, substituted alkyl, heteroalkyl, substituted heteroalkyl, alkenyl, substituted alkenyl, alkynyl, substituted alkynyl, aryl, substituted aryl, heteroaryl, substituted heteroaryl, arylalkyl, substituted arylalkyl, heteroarylalkyl and substituted heteroarylalkyl; each R$^1$ is independently selected from the group consisting of —H, alkyl, heteroalkyl, alkenyl, alkynyl, aryl, arylalkyl, heteroaryl and heteroarylalkyl.

In further embodiments of the invention the compounds are compounds of formula 7 where R=H.

In yet other embodiments of the invention the compounds are compounds of formula 7 where R=CH$_3$.

In yet further embodiment of the invention the compounds are compounds of formula 7 where R=allyl.

Other aspects of the invention provide pharmaceutically acceptable salts of the compounds described in Formulas 1-8.

In still other aspects, this invention provides pharmaceutical compositions comprising a pharmaceutically acceptable excipient and a therapeutically effective amount of at least one compound of this invention. These compositions find use as anti-apoptotic and anti-necrotic agents and for other conditions involving neural degeneration or injury.

In further aspects, this invention provides methods of treating an animal having a disease or injury capable of treatment by administration of a suitable compound of Formulas 1-8, comprising administration to that animal of at least one compound of this invention, optionally in conjunction with at least one other conventional therapeutic agent for the disease being treated.

In yet further aspects, the animal to be treated is a human.

In still further aspects, this invention provides methods of synthesizing, formulating and preparing pharmaceutical preparations comprising compounds of Formulas 1-8 of this invention.

Those with skill in the art will appreciate that the above structural formulae contain chiral centres, the number of which will depend on the different substituents. The chirality is only indicated for some centres. The chirality can be either R or S at each centre. The formulae drawings represent only one of the possible tautomeric, conformational isomeric or enantiomeric forms, it should be understood that the invention encompasses any tautomeric, conformational isomeric or enantiomeric forms which exhibit biological or pharmacological activity as described herein.

Pharmacology and Utility

Certain aspects of this invention include the use of compounds of the invention in treatment or prevention of cell damage, degeneration and/or death in mammals in response to injury or disease. Some embodiments comprise delivering a composition containing a compound of the invention to an animal suffering from neural degeneration, and in some cases, conditions involving apoptotic and necrotic cell death.

In some embodiments, compositions are desirable to treat an injury or disease of the CNS affecting or liable to affect brain cells. Compositions are provided that can also include one or more other agents that promote neural regeneration, decrease cell degeneration or death, or are neuroprotective.

Such other agents can be selected from the group consisting of for example, growth factors and associated derivatives, e.g., insulin-like growth factor-I [IGF-I], insulin-like growth factor-II [IGF-II], the tripeptide GPE, transforming growth factor-β1, activin, growth hormone, nerve growth factor, growth hormone binding protein, and/or IGF-binding proteins.

Other aspects of the invention include compositions and methods of promoting fasiculation of axons. By promoting formation of nerve bundles, compounds of the invention can be useful in treating conditions in which nerve processes (axons and/or dendrites) have become severed, such as in sharp force injuries, local areas of necrosis or disease, or other localized injuries to nerve processes.

In yet other embodiments, compositions and methods to treat or prevent cell damage and death in response to injury and disease, including CNS injury and disease, comprise administration of a therapeutic amount of a compound of the invention alone or in combination with other agents, after the insult. These embodiments can be particularly desirable in situations of unexpected injury, such as in cardiac arrest, trauma such as head injuries caused by automobile accidents, head wounds and the like.

In still further embodiments, compounds of the invention can be used either alone or in combination with other agents to prevent adverse effects of planned brain injury. Such conditions include CABG or other planned surgeries such as brain surgery, vascular surgery or other interventions that can lead to decreased perfusion of the nervous system. By treating an animal, such as a human being, in advance and/or simultaneously and/or after the surgery, adverse neurological effects may be ameliorated.

As indicated above, the present invention is broadly based upon the applicant's finding that compounds of the invention can protect cells, particularly nerve cells, against damage, loss of neurites, and/or apoptotic or necrotic cell death.

It is herein demonstrated that compounds of the invention exhibit neuroprotection in cell culture models of neurodegenerative disease and can therefore be an effective addition or alternative to conventional therapies for neural degeneration.

Although the mechanism of the protective effects is not known, one possible mechanism involves protecting cells from apoptotic and necrotic cell death. However, regardless of the mechanism of action, compounds of the invention can be used as an effective therapy for a variety of neurological diseases, including hypoxia, ischemia and neurotoxin-induced nerve damage. Moreover, compounds of the invention can be used in the absence of any particular neurological deficit to promote neurite outgrowth and fasiculation of nerves. Thus, in situations in which cell death is not necessarily associated with the neurological disorder (e.g., axonal damage such as caused by spinal cord injury), administration of compounds of the invention may be an effective way of promoting neurite regeneration.

Therapeutic Applications

Compositions and methods of the invention find use in the treatment of animals, such as human patients, suffering from neural injury or disease. Still more generally, the compositions and methods of the invention find use in the treatment of mammals, such as human patients, suffering from nerve damage or potential apoptotic and/or necrotic cell death, due to injuries and diseases.

Specific conditions and diseases characterised by neuronal degeneration, apoptosis and/or necrosis include but are not limited to Alzheimer's disease, Parkinson's disease, multiple sclerosis, amyotrophic lateral sclerosis, spinal muscular atrophy, peripheral neuropathy, Creutzfeldt-Jakob disease, AIDS dementia, progressive supranuclear palsy, myelinopathia centralis diffusa (vanishing white matter disease), chronic neurodegenerative disease, Huntington's disease, stroke, ischemic injury, hypoxic injury, reperfusion injury, head injury, CNS trauma, epilepsy, cerebral ischemia, glaucoma, retinal disorders, optic neuropathy, optic neuritis, Down's syndrome, encephalomyelitis, meningitis, panencephalitis, neuroblastoma, schizophrenia and depression. Each of the above conditions exhibits pathophysiological findings and symptoms that are mimicked by neurotoxicity associated with glutamate toxicity.

Still more generally, the invention has application in the induction of nerve bundle formation following insult in the form of trauma, toxin exposure, asphyxia or hypoxia-ischemia. Additionally, the invention has application in the treatment or prevention of apoptosis in response to injury or disease in the form of cancers, viral infections, autoimmune diseases, neurological diseases and injuries and cardiovascular diseases.

Treatment can be given before an injury, for example, before elective surgery. Examples of relevant elective procedures include neural surgery, in which retraction of lobes of the brain can lead to cerebral oedema, or heart operations, such as valve replacement, in which inevitable small emboli are said to lead to detectable impairment of brain function in some 75% of cases.

Determining Efficacy

The anti-apoptotic and anti-necrotic activity of compounds of the invention can be measured by in vivo using cell counts by methods known to those skilled in the art including the methods of Klempt et al (Klempt et al, 1992, *Molecular Brain Research:* 13: 93-101), microscopic examinations of morphology, cell counts of surviving and dead neurons stained with thionin/fuchsin and the like. Compounds of the invention can also be measured in vitro using mass spectroscopy, immunological, or chromatographic methods known in the art.

CNS damage can for example be measured clinically by the degree of permanent neurological deficit cognitive function, and/or propensity to seizure disorders. Herein are disclosed histological techniques suitable for measuring effects in vivo.

The therapeutic ratio of a compound is understood to be the ratio of (1) the mean dose that causes adverse side effect over (2) the mean dose that causes a desirable therapeutic effect. Thus, for compounds for which have therapeutic effects at relatively low doses and undesirable side effects at high doses, the therapeutic ratio is >1. Therapeutic ratio can be determined, for example, by comparing the dose that produces significant weight loss (or other observable side-effect) divided by the dose that produces anti-apoptotic and anti-necrotic activity in a suitable in vivo animal species such as the rat or mouse. Suitable models include a hypoxic-ischemic injury (Sirimanne et al, 1994 *Journal of Neuroscience Methods:* 55: 7-14) and experimental immune encephalomyelitis (Mendel et al., 1995 *Eur. J. Immunol.:* 25: 1951-1959).

Pharmaceutical Compositions and Administration

Compounds of the invention can be administered as part of a medicament or pharmaceutical preparation. This can involve combining a compound of the invention with any pharmaceutically appropriate carrier, adjuvant or excipient. The selection of the carrier, adjuvant or excipient will of course usually be dependent upon the route of administration to be employed.

In general, compounds of this invention will be administered in therapeutically effective amounts by any of the usual modes known in the art, either singly or in combination with other conventional therapeutic agents for the disease being treated. A therapeutically effective amount can vary widely depending on the disease or injury, its severity, the age and relative health of the animal being treated, the potency of the compound(s), and other factors. As anti-apoptotic and anti-necrotic agents, therapeutically effective amounts of compounds of this invention can range from 0.001 to 100 milligrams per kilogram mass of the animal, with lower doses such as 0.001 to 0.1 mg/kg being appropriate for administration through the cerebrospinal fluid, such as by intracerebroventricular administration, and higher doses such as 1 to 100 mg/kg being appropriate for administration by methods such as oral, systemic (e.g. transdermal), or parenteral (e.g. intravenous) administration. A person of ordinary skill in the art will be able without undue experimentation, having regard to that skill and this disclosure, to determine a therapeutically effective amount of a compound of this invention for a given disease or injury.

Compounds of the invention can be administered peripherally via any peripheral route known in the art. These can include parenteral routes for example injection into the peripheral circulation, subcutaneous, intraorbital, ophthalmic, intraspinal, intracisternal, topical, infusion (using e.g. slow release devices or minipumps such as osmotic pumps or skin patches), implant, aerosol, inhalation, scarification, intraperitoneal, intracapsular, intramuscular, intranasal, oral, buccal, transdermal, pulmonary, rectal or vaginal. The compositions can be formulated for parenteral administration to humans or other mammals in therapeutically effective amounts (e.g. amounts which eliminate or reduce the patient's pathological condition) to provide therapy for the neurological diseases described above.

Desirably, if possible, when administered as anti-apoptotic and anti-necrotic agents, compounds of this invention will be administered orally. The amount of a compound of this invention in the composition can vary widely depending on the type of composition, size of a unit dosage, kind of excipients, and other factors well known to those of ordinary skill in the art. In general, the final composition can comprise from 0.0001 percent by weight (% w) to 10% w of the compound of this invention, preferably 0.001% w to 1% w, with the remainder being the excipient or excipients.

Other convenient administration routes include subcutaneous injection (e.g. dissolved in a physiologically compatible carrier such as 0.9% sodium chloride) or direct administration to the CNS. Using stereotactic devices and accurate maps of an animal's CNS, a compound can be injected directly into a site of neural damage. Such routes of administration can be especially desired in situations in which perfusion of that location is compromised either by decreased vascular perfusion or by decreased cerebral spinal fluid (CSF) flow to that area. Examples include administration by lateral cerebroventricular injection or through a surgically inserted shunt into the lateral cerebroventricle of the brain of the patient, intraveneously, direct injection into the desired location or other routes.

The effective amount of compound in the CNS can be increased by administration of a pro-drug form of a compound which comprises a compound of the invention and a carrier, where the carrier is joined to a compound of the invention by a linkage which is susceptible to cleavage or digestion within the patient. Any suitable linkage can be employed which will be cleaved or digested following administration.

However, there is no intention on the part of the applicants to exclude other forms of administration.

In further embodiments of the invention, restoring nerve function in an animal can comprise administering a therapeutic amount of a compound of the invention in combination with another neuroprotective agent, selected from, for example, growth factors and associated derivatives (insulin-like growth factor-I [IGF-I], insulin-like growth factor-II [IGF-II], transforming growth factor-[3], activin, growth hormone, nerve growth factor, growth hormone binding protein, IGF-binding proteins [especially IGFBP-3], basic fibroblast growth factor, acidic fibroblast growth factor, the hst/Kfgk gene product, FGF-3, FGF-4, FGF-6, keratinocyte growth factor, androgen-induced growth factor. Additional members of the FGF family include, for example, int-2, fibroblast growth factor homologous factor-1 (FHF-1), FHF-2, FHF-3 and FHF-4, karatinocyte growth factor 2, glial-activating factor, FGF-10 and FGF-16, ciliary neurotrophic factor, brain derived growth factor, neurotrophin 3, neurotrophin 4, bone morphogenetic protein 2 [BMP-2], glial-cell line derived neurotrophic factor, activity-dependant neurotrophic factor, cytokine leukaemia inhibiting factor, oncostatin M, interleukin), $\alpha$-, $\beta$-, $\gamma$-, or consensus interferon, and TNF-$\alpha$. Other forms of neuroprotective therapeutic agents include, for example, clomethiazole; kynurenic acid, Semax, tacrolimus, L-threo-1-phenyl-2-decanoylamino-3-morpholino-1-propanol, andrenocorticotropin-(4-9) analogue [ORG 2766] and dizolcipine [MK-801], selegiline; glutamate antagonists such as, NPS1506, GV1505260, MK-801, GV150526; AMPA antagonists such as 2,3-dihydroxy-6-nitro-7-sulfamoylbenzo (f)quinoxaline (NBQX), LY303070 and LY300164; anti-inflammatory agents directed against the addressin MAdCAM-1 and/or its integrin $\alpha$4 receptors ($\alpha$4$\beta$1 and $\alpha$4$\beta$7), such as anti-MAdCAM-1 mAb MECA-367 (ATCC accession no. HB-9478).

The compound can be administered by a sustained-release system. Suitable examples of sustained-release compositions include semi-permeable polymer matrices in the form of shaped articles, e.g., films, or microcapsules. Sustained-release matrices include polylactides (U.S. Pat. No. 3,773,919; EP 58,481), copolymers of L-glutamic acid and gamma-ethyl-L-glutamate (Sidman et al., 1983, *Biopolymers:* 22: 547-56), poly(2-hydroxyethyl methacrylate) (Langer et al., 1981, *J. Biomed. Mater. Res.:* 15: 267), ethylene vinyl acetate (Langer et al., 1981, *J. Biomed. Mater. Res.:* 15: 267), or poly-D-(–)-3-hydroxybutyric acid (EP 133,988). Sustained-release compositions also include a liposomally entrapped compound. Liposomes containing the compound are prepared by methods known per se: DE 3,218,121, EP 52,322, EP 36,676, EP 88,046, EP 143,949, EP 142,641, Japanese Pat. Appln. 83-118008, U.S. Pat. Nos. 4,485,045 and 4,544, 545, and EP 102,324. Ordinarily, the liposomes are of the small (from or about 200 to 800 Angstroms) unilamellar type in which the lipid content is greater than about 30 mol percent cholesterol, the selected proportion being adjusted for the most efficacious therapy.

For parenteral administration, in one embodiment the compound is formulated generally by mixing each at the desired degree of purity, in a unit dosage injectable form (solution, suspension, or emulsion), with a pharmaceutically, or parenterally, acceptable carrier, i.e., one that is non-toxic to recipients at the dosages and concentrations employed and is compatible with other ingredients of the formulation.

Generally, the formulations are prepared by contacting the compound uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, a buffered solution, and dextrose solution. Non-aqueous vehicles such as fixed oils and ethyl oleate are also useful herein.

A carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; glycine; amino acids such as glutamic acid, aspartic acid, histidine, or arginine; monosaccharides, disaccharides, and other carbohydrates including cellulose or its derivatives, glucose, mannose, trehalose, or dextrins; chelating agents such as EDTA; sugar alcohols such as mannitol or sorbitol; counter-ions such as sodium; non-ionic surfactants such as polysorbates, poloxamers, or polyethylene glycol (PEG); and/or neutral salts, e.g., NaCl, KCl, $MgCl_2$, $CaCl_2$, etc.

A compound is typically formulated in such vehicles at a pH of from or about 4.5 to 8. It will be understood that use of certain of the foregoing excipients, carriers, or stabilizers will result in the formation of salts of the compound. The final preparation can be a stable liquid or lyophilized solid.

Formulations of the compound in pharmaceutical compositions can also include adjuvants. Typical adjuvants which can be incorporated into tablets, capsules, and the like are a binder such as acacia, corn starch, or gelatin; an excipient such as microcrystalline cellulose; a disintegrating agent like corn starch or alginic acid; a lubricant such as magnesium stearate; a sweetening agent such as sucrose or lactose; a flavouring agent such as peppermint, wintergreen, or cherry. When the dosage form is a capsule, in addition to the above materials, it can also contain a liquid carrier such as a fatty oil. Other materials of various types can be used as coatings or as modifiers of the physical form of the dosage unit. A syrup or elixir can contain the active compound, a sweetener such as sucrose, preservatives like propyl paraben, a colouring agent, and a flavouring agent such as cherry. Sterile compositions for injection can be formulated according to conventional pharmaceutical practice. For example, dissolution or suspension of the active compound in a vehicle such as water or naturally occurring vegetable oil like sesame, peanut, or cottonseed oil or a synthetic fatty vehicle like ethyl oleate or the like may be desired. Buffers, preservatives, antioxidants, and the like can be incorporated according to accepted pharmaceutical practice.

For injection, intraventricular administration, and other invasive routes of administration, the compounds used must be sterile. Sterility can be accomplished by any method known in the art, for example filtration through sterile filtration membranes (e.g., 0.2 micron membranes). Therapeutic compositions generally are placed into a container having a sterile access port, for example, an intravenous solution bag or vial having a stopper able to be pierced by a hypodermic injection needle.

A pharmaceutical formulation ordinarily will be stored in unit or multi-dose containers, for example, in sealed ampoules or vials, as an aqueous solution or as a lyophilized formulation for reconstitution. As an example of a lyophilized formulation, 10 mL vials are filled with 5 mL of sterile-filtered 1% (w/v) aqueous solution of compound, and the resulting mixture is lyophilized. The infusion solution is prepared by reconstituting the lyophilized compound using bacteriostatic Water-for-Injection. It can be readily appreciated that other dosage forms and types of preparations can be used, and all are considered to be part of this invention.

Preparation of the Compounds of this Invention

Starting materials and reagents used in preparing these compounds are either available from commercial suppliers such as Aldrich Chemical Company (Milwaukee, Wis.), Bachem (Torrance, Calif.), Sigma (St. Louis, Mo.), Strem (Newburyport, Ma.) or are prepared by methods well known to the person of ordinary skill in the art following procedures described in such references as Fieser and Fieser's Reagents for Organic Synthesis, vols 1-17, John Wiley and Sons, New York, N.Y., 1991; Rodd's Chemistry of Carbon Compounds, vols. 1-5 and supplements, Elsevier Science Publishers, 1989; Organic Reactions, vols. 1-40, John Wiley and Sons, New York, N.Y., 1991; March J; Advanced Organic Chemistry, 4$^{th}$ ed. John Wiley and Sons, New York, N.Y., 1992; and Larock: Comprehensive Organic Transformations, VCH Publishers, 1989. In most instances, amino acids and their esters or amides, and protected amino acids, are widely commercially available; and the preparation of modified amino acids and their amides or esters are extensively described in the chemical and biochemical literature and thus well-known to persons of ordinary skill in the art.

Starting materials, intermediates, and compounds of this invention can be isolated and purified using conventional techniques, including filtration, distillation, crystallization, chromatography, and the like. They can be characterized using conventional methods, including physical constants and spectral data.

All patent and literature references cited throughout the specification are expressly incorporated by reference in their entirety.

EXAMPLES

The present invention is further illustrated by the following examples. These examples are offered by way of illustration only and are not intended to limit the invention in any manner.

General Methods

Flash chromatography was performed using Scharlau 60 (40-60 μm mesh) silica gel. Analytical thin layer chromatography was carried out on 0.20 mm pre-coated silica gel plates (ALUGRAM® SIL G/UV$_{254}$) and compounds visualized using UV fluorescence, or heating of plates dipped in potassium permanganate in alkaline solution.

Melting points in degrees Celsius (° C.) were determined on an Electrothermal® melting point apparatus and are uncorrected.

Optical rotations were measured at 20° C. on a Perkin Elmer 341 polarimeter using 10 cm path length cells and are given in units of $10^{-1}$ degcm$^2$g$^{-1}$. Samples were prepared in the solvent indicated at the concentration specified (measured in g/100 cm$^3$). IR spectra were recorded on a Perkin Elmer Spectrum One FT-IR spectrometer. The samples were prepared as thin films on sodium chloride discs or as solids in potassium bromide discs. A broad signal indicated by br. The frequencies (υ) as absorption maxima are given in wavenumbers (cm$^{-1}$).

NMR spectra were recorded on a Bruker AVANCE DRX400 ($^1$H, 400 MHz; $^{13}$C, 100 MHz) or a Bruker AVANCE 300 ($^1$H, 300 MHz; $^{13}$C, 75 MHz) spectrometer at ambient temperatures. For $^1$H NMR data chemical shifts are described in parts per million downfield from SiMe$_4$ and are reported consecutively as position ($\delta_H$), relative integral, multiplicity (s=singlet, d=doublet, t=triplet, dd=doublet of doublets, m=multiplet, br=broad), coupling constant (J/Hz) and assignment. For $^{13}$C NMR data, chemical shifts are described in parts per million relative to CDCl$_3$ and are reported consecutively as position ($\delta_C$), degree of hybridization as determined by DEPT experiments, and assignment. $^1$H NMR spectra were referenced internally using SiMe$_4$ (δ 0.00) or CDCl$_3$ (δ 7.26). $^{13}$C NMR spectra were referenced internally using CDCl$_3$ (δ 77.0). When two sets of peaks arise in the NMR spectra due to different conformations around the glycine-proline amide bond, the chemical shift for the minor cis conformer is marked with an asterisk (*).

Accurate mass measurements were recorded on a VG-70SE mass spectrometer. Hexane and dichloromethane were distilled prior to use. Methanol was dried using magnesium turnings and iodine, and distilled under nitrogen. Triethylamine was dried over calcium hydride and distilled under nitrogen.

Analytical HPLC was performed on a Waters 600 system using an Alltech Econosphere C18 RP column (150 mm×4.6 mm). A 5 minute flush with water (containing 0.05% trifluoroacetic acid) followed by gradient elution of water (containing 0.05% trifluoroacetic acid) to acetonitrile over 25 mins was used at a flow rate of 1 ml min$^{-1}$. For semi-preparative purification an Alltech Econosil C18 RP column (250 mm×22 mm) was used under isocratic conditions, typically 80% water (containing 0.05% trifluoroacetic acid):20% acetonitrile at a flow rate of 13 ml min$^{-1}$.

Example 1

Synthesis of (2S, 3'S, 8'S)-2-{[(3'-Amino-1'-aza-2'-oxobicyclo[6.3.0]undecyl)-8'-carbonyl]amino}-1,5-pentanedioic acid trifluoroacetate salt Scheme 1 Reagents, conditions and yields:

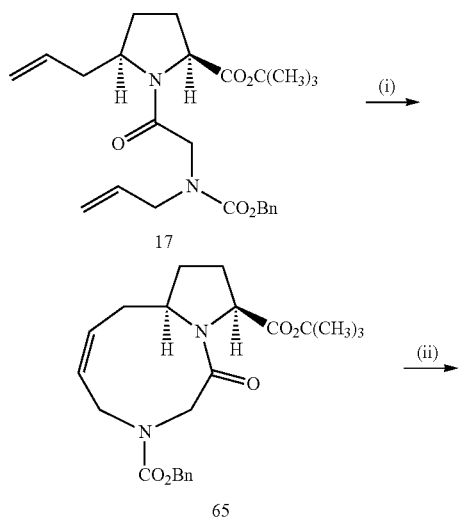

-continued

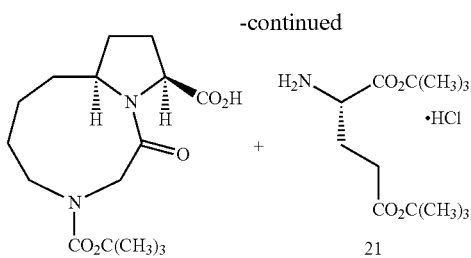

66

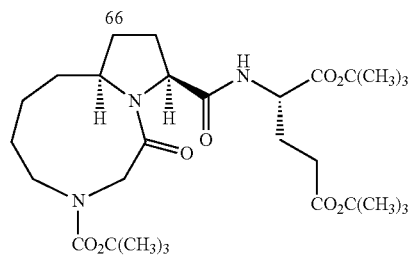

67

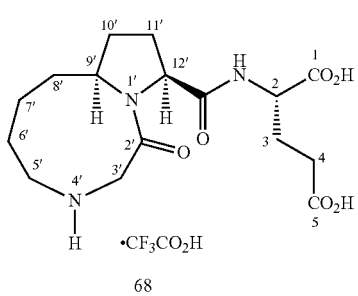

68

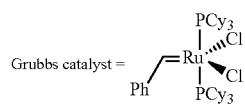

Grubbs catalyst =

(i) Grubbs catalyst, CH$_2$Cl$_2$, reflux, 48 h, then DMSO, RT, 24 h (46%);
(ii) PtO$_2$, THF, H$_2$, RT, 16 h then 30% HBr/HOAc, RT, 2 h then NaHCO$_3$, H$_2$O, dioxane, Boc$_2$O, RT, 4 d(78%, 3 steps);
(iii) BoP-Cl, Et$_3$N, CH$_2$Cl$_2$, 0° C. to RT, 24 h (64%);
(iv) CF$_3$CO$_2$H, CH$_2$Cl$_2$, RT, 4 h (80%).

N-tert-Butoxy-(S)-allylglycine 2

A solution of allylglycine 1 (0.1 g, 0.87 mmol) and sodium hydrogen carbonate (0.08 g, 0.96 mmol) in water/dioxane (1:1, v/v, 4 cm$^3$) was cooled to 0° C., di-tert-butyl dicarbonate (0.07 g, 0.32 mmol) was added and the solution stirred for 2 h at 0° C. Di-tert-butyl dicarbonate (0.07 g, 0.32 mmol) was then added and the solution stirred for a further 2 h at 0° C., after which time further di-tert-butyl dicarbonate (0.1 g, 0.46 mmol) was added and the solution allowed to warm to room temperature and stirred overnight. Dioxane was removed under reduced pressure at 40° C. and the resultant residue was dissolved in water, washed with ether and the aqueous layer acidified with 2 M aqueous hydrochloric acid and extracted with ethyl acetate. The combined organic layers were dried (MgSO$_4$), filtered and the solvent removed in vacuo to give crude carbamate 2 (0.14 g, ca. 72%) as a colourless oil. This material was used as such for the subsequent step. Carbamate 2 was shown to be a 73:27 mixture of rotamers: $\delta_H$ (400 MHz; CDCl$_3$; Me$_4$Si) 1.45 [9H, s, C(CH$_3$)$_3$], 2.51-2.63 [2H, m, CH$_2$(allyl)], 4.19* (0.27H, br s, 2-H), 4.41 (0.73H, d, J 6.1, 2-H), 5.13-5.20 (2.73H, m, =CH$_2$, N—H), 5.70-5.80 [1H, m, C(H)=CH$_2$], 6.26 (0.27H, br s, N—H*) and 9.16 (1H, br s, OH); $\delta_C$ (100 MHz; CDCl$_3$) 28.2 [CH$_3$, C(CH$_3$)$_3$], 36.3 [CH$_2$, CH$_2$(allyl)], 52.7 (CH, 2-C), 54.2* (CH, 2-C), 80.2 [quat., C(CH$_3$)$_3$], 81.6* [quat., C(CH$_3$)$_3$], 119.2 (CH$_2$, =CH$_2$), 132.1 [CH, C(H)=CH$_2$], 155.4 (quat., NCO$_2$), 155.4* (quat., NCO$_2$), and 176.1 (quat., 1-CO).

N-tert-Butyloxy-(S)-allylglycl-(S)-allylproline methyl ester 4

N,N'-Dicyclohexylcarbodiimide (0.1 g, 0.49 mmol) was added to a stirred solution of (S)-allylproline methyl ester 3 (0.1 g, 0.49 mmol), N-tert-butoxy-(S)-allylglycine 2 (0.12 g, 0.54 mmol), N-hydroxybenzotriazole (0.065 g, 0.486 mmol) and triethylamine (0.07 cm$^3$, 0.486 mmol) in dichloromethane (10 cm$^3$) at 0° C. The mixture was stirred overnight at room temperature, refrigerated for 2 h and filtered through Celite™ to remove dicyclohexyl urea. The filtrate was washed with saturated aqueous sodium hydrogen carbonate, 2 M aqueous hydrochloric acid, dried (Na$_2$SO$_4$), filtered and the solvent removed to yield an oil which was purified by chromatography (SiO$_2$, 4:1, 3:1, hexane-ethyl acetate) to afford diene 4 (0.041 g, ca. 23%) as a colourless oil. Diene 4 existed exclusively as the trans GlyC(O)—NPro conformer: $\delta_H$ (400 MHz; CDCl$_3$; Me$_4$Si) 1.43 [9H, s, C(CH$_3$)$_3$], 1.94-2.15 (4H, m, Proβ-H$_2$, Proγ-H$_2$), 2.35 [1H, p, J 7.1, allyl-H$_A$H$_B$(Pro)], 2.50 [1H, p, J 7.2, allyl-H$_A$H$_B$(Pro)], 2.62 [1H, dd, J 14.0 and 8.4, allyl-H$_A$H$_B$(Gly)], 3.18 [1H, dd, J 14.1 and 6.5, allyl-H$_A$H$_B$(Gly)], 3.65-3.80 (5H, m, OCH$_3$ and Pro δH$_2$), 4.46 (1H, dd, J 15.4 and 6.7, Glyα-H), 5.08-5.25 (5H, m, 2×=CH$_2$ and N—H) and 5.63-5.86 (2H, m, 2×C(H)=CH$_2$); $\delta_C$ (100 MHz; CDCl$_3$) 23.6 (CH$_2$, Proγ-C), 28.2 [CH$_3$, C(CH$_3$)$_3$], 35.0 (CH$_2$, Proγ(3-C), 36.3 [CH$_2$, CH$_2$(allyl)Gly], 37.7 [CH$_2$, CH$_2$(allyl)Pro], 48.5 (CH$_2$, Pro δ-C), 51.6 (CH, Glyα-C), 52.2 (CH$_3$, OCH$_3$), 68.5 (quat., Proα-C), 79.6 [quat., C(CH$_3$)$_3$], 118.5 (CH$_2$, =CH$_2$), 119.1 (CH$_2$, =CH$_2$), 132.7 [CH, C(H)=CH$_2$], 133.0 [CH, C(H)=CH$_2$], 155.4 (quat., NCO$_2$), 170.2 (quat., Gly-CO) and 173.7 (quat., Pro-CO).

(3S,8S)-1-Aza-3-(tert-butyloxycarbonylamino)-8-methoxycarbonyl-2-oxobicyclo[6.3.0]undec-5-ene 5

A solution of freshly sublimed potassium tert-butoxide (0.0018 g, 0.0157 mmol) in dry tetrahydrofuran (1 cm$^3$) was added to a stirred suspension of 1,3-bis(2,4,6-trimethylphenyl)-4,5-dihydro-imidazolium tetrafluoroborate (0.07 g, 0.0177 mmol) in dry tetrahydrofuran (2 cm$^3$) under an atmosphere of nitrogen. Dry tetrahydrofuran (1 cm$^3$) was used to rinse the remaining potassium tert-butoxide from the reaction flask. The resultant suspension was stirred for 2 min then a solution of bis(tricyclohexylphosphine)benzylidineruthenium dichloride (Grubbs's catalyst) (0.010 g, 0.011 mmol) in dry benzene (10 cm$^3$) was added and the purple solution heated at 80° C. for 35 min. The dark brown solution was cooled to room temperature and a solution of diene 4 (0.041 g, 0.112 mmol) in dry benzene (40 cm$^3$) added and the mixture heated at 45° C. for 48 h. The brown solution was cooled to room temperature, dimethyl sulphoxide (0.043 g, 0.56 mmol) was added and the mixture stirred overnight. The solvent was removed in vacuo and the residue purified by chromatography (SiO$_2$, 2:1, 1:1, hexane-ethyl acetate) to give alkene 5 (0.022 g, 58%) as a greenish oil. Alkene 5 existed exclusively as the trans C(O)—NPro conformer: $[\alpha]_D$ −86.3 (c 0.183 in CH$_2$Cl$_2$) [lit.[2], −87.4 (c 0.35 in CHCl$_3$]; $\delta_H$ (400 MHz; CDCl$_3$; Me$_4$Si) 1.44 [9H, s, C(CH$_3$)$_3$], 1.66-1.86 (2H, m, 10-H$_2$), 1.96-2.11 (2H, m, 9-H$_A$H$_B$ and 4-H$_A$H$_B$), 2.46 (1H, dd, J 12.3 and 6.1, 9-H$_A$H$_B$), 2.66 (1H, dd, J 14.8 and 8.2, 7-H$_A$H$_B$), 2.80-2.90 (1H, m, 4-H$_A$H$_B$), 3.04 (1H, dd, J 15.1 and 8.6, 7-$H_AH_B$), 3.40 (1H, ddd, J 11.6, 11.1 and 7.4, 11-$H_AH_B$), 3.76-3.83 (1H, m, 11-$H_AH_B$), 3.78 (3H, s, $OCH_3$), 4.97-5.04 (1H, m, 3-H), 5.52-5.63 (2H, m, 6-H and N—H) and 5.74-5.79 (1H, m, 5-H); $\delta_C$ (100 MHz; $CDCl_3$) 20.6 ($CH_2$, 10-C), 28.2 [$CH_3$, $C(CH_3)_3$], 35.0 ($CH_2$, 7-C), 35.4 ($CH_2$, 4-C), 38.4 ($CH_2$, 9-C), 48.4 ($CH_2$, 11-C), 50.8 (CH, 3-C), 53.0 ($CH_3$, $OCH_3$), 69.7 (quat., 8-C), 79.4 [quat., $C(CH_3)_3$], 122.8 (CH, 5-C), 132.2 (CH, 6-C), 154.8 (quat., $NCO_2$), 171.5 (quat., 2-C) and 173.7 (quat., 8-CO).

(2S, 3'S, 8'S)-Di-tert-butyl 2-{[(1'-aza-3'-(tert-butyloxycarbonylamino)-2'-oxobicyclo[6.3.0]undec-5'-ene)-8'-carbonyl]amino}-1,5-pentadioate 7

To a solution of alkene 5 (0.022 g, 0.065) in dioxane (0.7 cm$^3$) was added 1 M aqueous sodium hydroxide (0.32 cm$^3$, 0.32 mmol) and the opaque solution stirred at room temperature for 17 h. Water was added and the mixture washed with dichloromethane. The aqueous layer was acidified with citric acid and the product extracted with dichloromethane. The organic layers were pooled, dried ($MgSO_4$) and the solvent removed to afford an oil (0.020 g). To a solution of this oil in dichloromethane (4 cm$^3$) was added L-glutamic acid di-tert-butyl ester p-toluenesulphonate 6 (0.025 g, 0.085 mmol) was added and the solution cooled to 0° C. Triethylamine (0.017 g, 0.17 mmol) and bis(2-oxo-3-oxazolidinyl)phosphinic chloride (0.021 g, 0.085 mmol) were added and the solution stirred for 20 h. The reaction mixture was washed with 2 M aqueous hydrochloric acid, saturated aqueous sodium hydrogen carbonate, dried ($Na_2SO_4$), filtered and the solvent removed to yield an oil (0.041 g) which was purified by chromatography ($SiO_2$, 1:1, 2:3, hexane-ethyl acetate) to give amide 7 (0.025 g, 69% in 2 steps) as a colorless oil. Amide 7 existed exclusively as the cis C(O)—NPro conformer: $[\alpha]_D$ −49.6 (c 0.25 in $CH_2Cl_2$); $\delta_H$ (400 MHz; $CDCl_3$; $Me_4Si$) 1.40-1.44 [27H, m, 3×$C(CH_3)_3$], 1.55-1.66 (1H, m), 1.78 (1H, p, J 6.4), 1.89 (1H, td, J 13.2 and 6.1), 2.05-2.39 (5H, m), 2.65-2.75 (2H, m, 4'-$H_2$), 2.80 (1H, dd, J 15.0 and 7.9, 7'-$H_AH_B$), 2.92 (1H, dd, J 14.9 and 8.9, 7'-$H_AH_B$), 3.55 (1H, ddd, J 11.8, 11.8 and 7.0, 11'-$H_AH_B$), 3.65-3.70 (1H, m, 11'-$H_AH_B$), 4.40-4.46 (1H, m, 3'-H), 4.88-4.97 (2H, m, 6'-H and 2-H), 5.67-5.79 (2H, m, 5'-H and N—H) and 8.36 (1H, d, J 8.4, N—H); $\delta_C$ (100 MHz; $CDCl_3$) 20.4 ($CH_2$, 10'-C), 25.4 ($CH_2$, 3-C), 27.9 [$CH_3$, $C(CH_3)_3$], 28.0 [$CH_3$, $C(CH_3)_3$], 28.2 [$CH_3$, $C(CH_3)_3$], 31.5 ($CH_2$, 4-C), 32.2 ($CH_2$, 4'-C), 34.6 ($CH_2$, 7'-C), 37.4 ($CH_2$, 9'-C), 49.3 ($CH_2$, 11'-C), 52.1 (CH, 3'-C), 52.8 (2-C), 71.8 [quat., 8'-C), 80.4 [quat., $C(CH_3)_3$], 81.1 [quat., $C(CH_3)_3$], 125.0 (CH, 5'-C), 130.2 (CH, 6'-C), 156.3 (quat., $NCO_2$), 170.5 (quat., 2'-C), 171.9 (quat., 8'-CO), 171.2 (quat., 1-C) and 173.5 (quat., 5-C); m/z (EI+) 565.3365 (M$^+$. $C_{29}H_{47}N_3O_8$ requires 565.3363).

(2S, 3'S, 8'S) 2-{[(1'-Aza-3'-amino-2'-oxobicyclo[6.3.0]undecyl)-8'-carbonyl]amino}-1,5-pentandioic acid trifluoroacetate salt 8

$PtO_2$ (0.001 g, 0.004 mmol) was added to a stirred solution of amide 7 (0.025 g, 0.044 mmol) in tetrahydrofuran (4 cm$^3$) under a nitrogen atmosphere. The mixture was hydrogenated (1 atm. of hydrogen) for 17 h, filtered through Celite™, and the solvent removed in vacuo. The residue was dissolved in dichloromethane (3 cm$^3$), trifluoroacetic acid (1 cm$^3$) added and the solution stirred for 4 h at room temperature. Removal of the volatiles in vacuo and analysis by HPLC and NMR showed the reaction to be incomplete. The residue was therefore redissolved in dichloromethane-trifluoroacetic acid (3:1, 4 cm$^3$) and the solution stirred at room temperature for 2.5 h. The volatiles were removed in vacuo, and the residue purified by RP HPLC [20% acetonitrile:80% water (containing 0.05% trifluoroacetic acid)] to give an oil which was triturated from ether/toluene to give 8 (0.0167 g, 81%, in 2 steps) as a hygroscopic white solid. Macrocycle 8 existed exclusively as the cis C(O)—NPro conformer: mp 75-85° C.; $[\alpha]_D$ −4.4 (c 0.16 in MeOH); $\delta_H$ (400 MHz; $D_2O$) 1.30-1.39 (1H, m, 5'-$H_AH_B$), 1.57-1.65 (1H, m, 6'-$H_AH_B$), 1.79-1.91 (4H, m, 5'-$H_AH_B$, 6'-$H_AH_B$, 4'-$H_AH_B$ and 10'-$H_AH_B$), 1.98-2.13 (4H, m, 4'-$H_AH_B$, 10'-$H_AH_B$, 7'-$H_AH_B$ and 3-$H_AH_B$), 2.23-2.37 (4H, m, 9'-$H_2$, 3-$H_AH_B$ and 7'-$H_AH_B$), 2.53 (2H, t, J 7.5, 4-$H_2$), 3.68 (1H, dt, J 14.2 and 7.4, 11'-$H_AH_B$), 3.79 (1H, dt, J 14.0 and 7.5, 11'-$H_AH_B$), 4.20 (1H, dd, J 11.2 and 6.3, 3-H) and 4.53 (1H, dd, J 10.2 and 4.9, 2-H); $\delta_C$ (100 MHz; $D_2O$) 20.4 ($CH_2$, 10'-C), 21.2 ($CH_2$, 6'C), 22.1 ($CH_2$, 5'-C), 24.8 ($CH_2$, 3-C), 30.3 ($CH_2$, 4-C), 31.1 ($CH_2$, 4'-C), 36.4 ($CH_2$, 7'-C), 40.9 ($CH_2$, 9'-C), 49.1 ($CH_2$, 11'-C), 51.2 (CH, 3'-C), 52.4 (CH, 2-C), 70.9 (quat., 8'-C), 116.1 (quat., q, J 291, $CF_3$), 162.7 (quat., q, J 36.0, $CF_3CO_2H$), 169.4 (quat., 2'-C), 174.6 (quat., 8'-CO), 175.3 (quat., 1-C) and 177.0 (quat., 5-C); m/z (FAB+) 356.1830 [MH(free base)$^+$. $C_{16}H_{16}N_3O_6$ requires 356.1822].

Example 2

Synthesis of (2S, 9'R, 12'S)-2-{[(1',4'-Diaza-2'-oxobicyclo[7.3.0]dodecyl)-12'-carbonyl]amino}-1,5-pentanedioic acid trifluoroacetate salt Scheme 1 Reagents, conditions and yields:

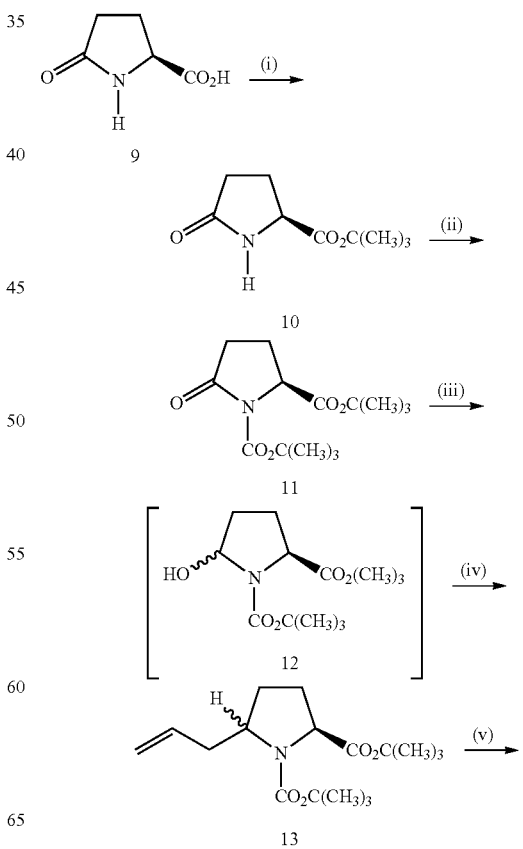

21
-continued

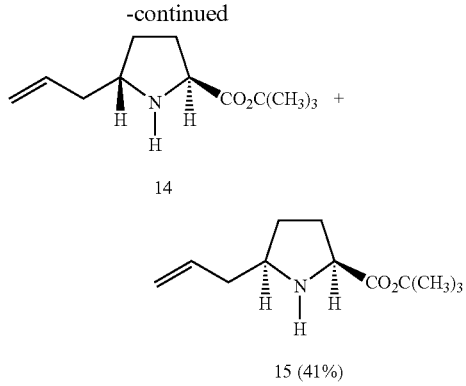

14

15 (41%)

(i) 70% (aq) HClO₄, tert-BuOAc, RT, 24 h (56%);
(ii) DMAP, Boc₂O, CH₃CN, RT, 19 h (95%);
(iii) LiEt₃BH, THF, -78° C., 1 h, then 30% H₂O₂, 0° C., 0.5 h;
(iv) Me₃SiOTf, allyltributyltin, CH₂Cl₂, -78° C., 2 h (70%, 2 steps);
(v) 4M HCl, dioxane, 0° C. 1 h, then RT, 40 min (72%).

Scheme 2 Reagents, conditions and yields:

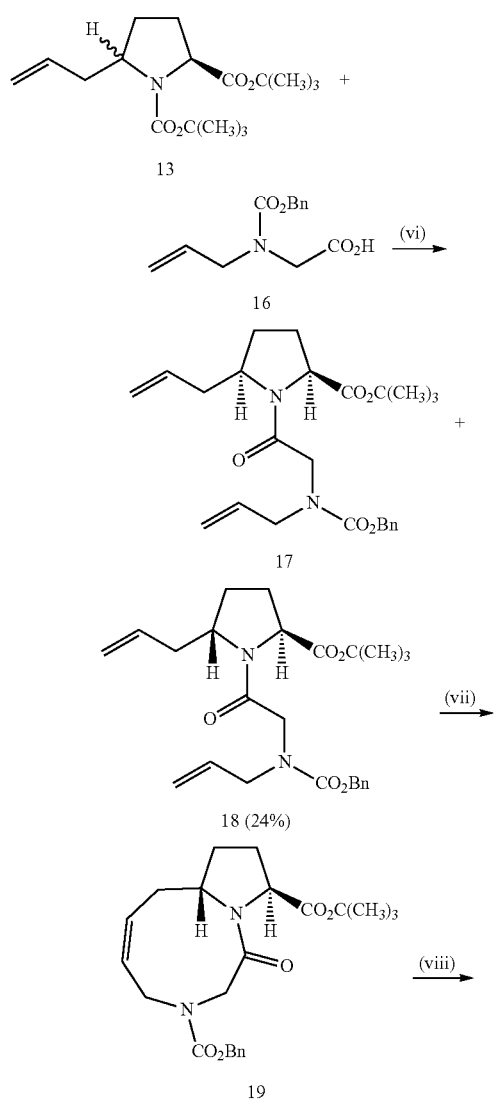

13

16

17

18 (24%)

19

22
-continued

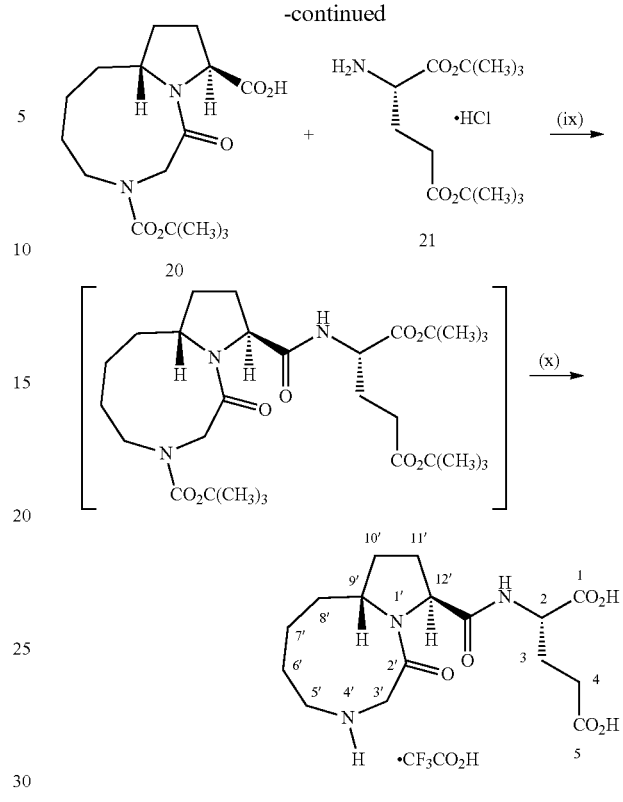

20

21

22

(vi) 4M HCl, dioxane, 0° C. 1 h, then RT, 40 min, then 8, EDCl, CH₂Cl₂, Et₃N, 0° C. to RT, 16 h (64% over 2 steps);
(vii) 9, Grubbs's catalyst, CH₂Cl₂, reflux, 48 h, then DMSO RT, 24 h (42%);
(viii) PtO₂, H₂, THF, RT, 16 h then 30% HBr/HOAc, RT, 2 h, then NaHCO₃, H₂O, dioxane, Boc₂O, RT, 3 d (58%, 3 steps);
(ix) BoP-Cl, Et₃N, 0° C. to RT, 17 h;
(x) CH₂Cl₂, CF₃CO₂H, RT, 6 h (55% 2 steps).

Grubbs catalyst = 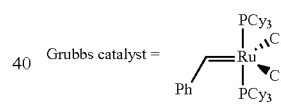

(S)-tert-Butyl pyroglutamate 10

Perchloric acid (70% aqueous, 0.521 cm³, 6.05 mmol) was added dropwise to a stirred suspension of (S)-pyroglutamic acid 9 (1 g, 7.75 mmol) in tent-butyl acetate (12 cm³, 85.5 mmol). The mixture was stirred for 24 h then sodium carbonate (0.80 g, 7.60 mmol) was added cautiously, ether was added and the organic phase washed with saturated sodium hydrogen carbonate solution and brine. The aqueous phase was extracted with ethyl acetate, dried (MgSO₄), filtered and the solvent removed to yield an oil to which was added carbon tetrachloride and the solvent evaporated in vacuo to remove traces of acetic acid to give ester 10 (0.81 g, 56%) as a white solid: $\delta_H$ (300 MHz; CDCl₃; Me₄Si) 1.48 [9H, s, C(CH₃)], 2.33-2.45 (4H, m, 3-H₂, 4-H₂), 4.12-4.16 (1H, m, 5-H) and 6.16 (1H, br s, N—H); $\delta_C$ (75 MHz; CDCl₃) 24.7 (CH₂, 4-C), 27.8 [CH₃, C(CH₃)], 29.2 (CH₂, 3-C), 55.9 (CH, 5-C), 82.3 [quat., C(CH₃)], 170.9 (quat., 5-CO) and 177.7 (quat., 2-C).

(S)-tert-Butyl N-tert-butoxycarbonylpyroglutamate 11

To a solution of ester 10 (0.85 g, 4.58 mmol) and dimethylaminopyridine (0.056 g, 0.458 mmol) in acetonitrile (40 cm³) was added di-tert-butyl dicarbonate (1.12 g, 5.50 mmol). The resultant solution was stirred at room temperature for 19 h, concentrated in vacuo and purified by chromatography (SiO₂, 4:1, 3:1 hexane-ethyl acetate; gradient elution) to give carbamate 11 (1.24 g, 95%) as a white solid: mp 53-55° C. (lit. 54-56° C.); $\delta_H$ (300 MHz; CDCl₃; Me₄Si) 1.48 [9H, s, C(CH₃)₃], 1.50 [9H, s, C(CH₃)₃], 1.93-2.03 (1H, m), 2.16-2.35 (1H, m), 2.40-2.66 (2H, m) and 4.47 (1H, dd, J 9.4 2.7, 5-H); $\delta_C$ (75 MHz; CDCl₃) 21.6 (CH₂, 4-C), 27.8 [CH₃, C(CH₃)₃], 31.0 (CH₂, 3-C), 59.5 (CH, 5-C), 82.2 [quat., C(CH₃)], 83.2 [quat., C(CH₃)₃], 149.2 (quat., NCO₂), 170.3 (quat., 5-CO) and 173.4 (quat., 2-C).

N-tert-Butoxycarbonyl-5-allyl-L-proline tert-butyl ester 13

To a stirred solution of carbamate 11 (1.14 g, 3.98 mmol) in dry tetrahydrofuran (40 cm³) was added a 1 mol L⁻¹ tetrahydrofuran solution of lithium triethylborohydride (4.78 cm³, 4.78 mmol) at −78° C. under at atmosphere of nitrogen. The solution was stirred for 1 h, saturated aqueous sodium hydrogen carbonate (10 cm³) added and the cooling bath removed. The temperature was allowed to reach 0° C. then 30% aqueous hydrogen peroxide (30 drops) was added and stirring was continued at 0° C. for 30 min. The aqueous layer was extracted with ether and the combined organic extracts were washed with brine, dried (MgSO₄), filtered and the solvent removed to give alcohol 12 (1.17 g) which contained ~8% of 11 as determined by NMR. The crude alcohol 12 was dissolved in dry dichloromethane (20 cm³) and added dropwise to a stirred solution of trimethylsilyl triflate (1.44 cm³, 7.96 mmol) and allyltributylstannane (2.46 cm³, 7.96 mmol) in dry dichloromethane (20 cm³) at −78° C. under nitrogen. The solution was stirred at −78° C. for 2 h, saturated aqueous sodium hydrogen carbonate (15 cm³) was added and the reaction warmed to room temperature. The aqueous layer was extracted with dichloromethane and the pooled organic extracts dried (MgSO₄) and filtered. Removal of the solvent in vacuo gave an oil (3.855 g) which was purified by chromatography (SiO₂, 8:1, 7:1, hexane-ethyl acetate; gradient elution) to afford an oil (1.047 g) contaminated with tributylstannane residues. Further chromatography (SiO₂, 12:1, 10:1, 8:1, hexanes-ethyl acetate; gradient elution) gave alkene 13 (0.872 g, 70%, in 2 steps) as a colourless oil. Alkene 13 was shown to be a 57:43 mixture of C(2)/C(5) cis:trans isomers: $\delta_H$ (300 MHz; CDCl₃; Me₄Si) 1.41-1.45 [18H, m, 2×C (CH₃)₃], 1.67-2.24 [5H, m, Proβ-H₂, Proγ-H₂ and CH$_A$CH$_B$(allyl)], 2.39-2.71 [1H, m, CH$_A$CH$_B$(allyl)], 3.79-4.18 (2H, m, Proα-H and Proδ-H), 4.99-5.08 (2H, m, =CH₂) and 5.67-5.85 [1H, m, C(H)=CH₂]; $\delta_C$ (75 MHz; CDCl₃) 26.6 (CH₂, Proγ-C), 27.4 (CH₂, Proγ-C), 27.8 (CH₂, Proγ-C), 27.86 [CH₃, C(CH₃)₃], 27.92 [CH₃, C(CH₃)₃], 28.25 [CH₃, C(CH₃)₃], 28.31 [CH₃, C(CH₃)₃], 28.4 (CH₂, Proβ-C), 29.4 (CH₂, Proβ-C), 30.2 (CH₂, Proβ-C), 38.1 [CH₂, CH₂(allyl)], 38.5 [CH₂, CH₂(allyl)], 38.98 [CH₂, CH₂(allyl)], 39.1 [CH₂, CH₂(allyl)], 57.4 (CH, Proδ-C), 58.0 (CH, Proδ-C), 60.6 (CH, Proα-C), 60.9 (CH, Proα-C), 79.5 [quat., C(CH₃)₃], 79.6 [quat., C(CH₃)₃], 80.7 [quat., C(CH₃)₃], 80.74 [quat., C(CH₃)₃], 116.9 (CH₂, =CH₂), 116.99 (CH₂, =CH₂), 117.0 (CH₂, =CH₂), 135.12 (CH, C(H)=CH₂), 135.2 (CH, C(H)=CH₂), 135.5 (CH, C(H)=CH₂), 153.7 (quat., NCO₂), 153.8 (quat., NCO₂), 154.3 (quat., NCO₂), 172.1 (quat., Proα-CO), 172.2 (quat., Proα-CO) and 172.3 (quat., Proα-CO); m/z (EI+) 312.2171 (M⁺. C₁₇H₃₀NO₄ requires 312.2175).

(1S,2S)-5-Allylproline tert-butyl ester (trans) 14 and (1S,2R) 5-allylproline tert-butyl ester (cis) 15

To alkene 13 (0.24 g, 0.77 mmol) was added a 4 mol L⁻¹ solution of hydrogen chloride in dioxane (4 cm³) at 0° C. The solution was stirred for 1 h at 0° C. then room temperature for 40 min at which time reaction was complete (by tlc). The mixture was cooled to 0° C., neutralized with a saturated solution of aqueous sodium hydrogen carbonate and the product extracted with dichloromethane. Removal of the solvent in vacuo yielded an oil (0.142 g) which was purified by chromatography (SiO₂, 2:1, 5:4, 1:1, hexanes-ethyl acetate) to give (i) amine 14 (trans) (0.051 g, 31%) as a colourless oil. This compound showed no NOE between the Proα-H atom at δ3.70 and the Proδ-H atom at δ3.26: $[\alpha]_D$ −31 (c 0.47 in CH₂Cl₂); δH (300 MHz; CDCl₃; Me₄Si) 1.35-1.41 (1H, m, Proγ-H$_A$H$_B$), 1.43 [9H, m, C(CH₃)₃], 1.72-1.90 (2H, Proγ-H$_A$H$_B$ and Proβ-H$_A$H$_B$), 2.11-2.20 [3H, m, Proβ-H$_A$H$_B$ and CH₂(allyl)], 2.47 (1H, s, N—H), 3.26 (1H, p, J 6.5, Proδ-H), 3.70 (1H, dd, J 8.5 and 5.9, Proα-H), 4.98-5.10 (2H, m, =CH₂) and 5.73-5.84 [1H, m, C(H)=CH₂]; $\delta_C$ (75 MHz; CDCl₃) 27.9 [CH₃, C(CH₃)₃], 29.5 (CH₂, Proβ-C), 30.7 (CH₂, Proγ-C), 40.8 [CH₂, CH₂(allyl)], 57.6 (CH, Proδ-C), 59.7 (CH, Proα-C), 80.7 [quat., C(CH₃)₃], 116.1 (CH₂, =CH₂), 136.0 [CH, C(H)=CH₂], and 174.9 (quat., Proα-CO); (ii) amine 15 (cis) (0.066 g, 41%) as a colourless oil. This compound showed an NOE between the Proα-H atom at 63.57-3.62 and the Proδ-H atom at 63.03-3.12: $[\alpha]_D$ −22.1 (c 0.66 in CH₂Cl₂); $\delta_H$ (300 MHz; CDCl₃; Me₄Si) 1.24-1.30 (1H, m, Proγ-H$_A$H$_B$), 1.42 [9H, m, C(CH₃)₃], 1.78-1.87 (2H, Proγ-H$_A$H$_B$ and Proβ-H$_A$H$_B$), 1.98-2.07 (1H, m, H$_A$H$_B$), 2.18-2.31 [3H, m, CH₂(allyl) and N—H], 3.03-3.12 (1H, m, Proδ-H), 3.57-3.62 (1H, m, Proα-H), 4.99-5.1 (2H, m, =CH₂) and 5.72-5.86 [1H, m, C(H)=CH₂]; $\delta_C$ (75 MHz; CDCl₃) 27.9 [CH₃, C(CH₃)₃], 30.4 (CH₂, Proβ-C), 31.1 (CH₂, Proγ-C), 39.9 [CH₂, CH₂(allyl)], 59.1 (CH, Proδ-C), 60.5 (CH, Proα-C), 80.8 [quat., C(CH₃)], 116.5 (CH₂, =CH₂), 135.5 [CH, C(H)=CH₂], and 174.3 (quat., Proα-CO); m/z (CH+) 212.1647 (MH⁺. C₁₂H₂₂NO₂ requires 212.1651).

(1S,2S)-N-Allyl-N-benzyloxycarbonylglycine-5-allylproline tert-butyl ester (trans) 18 and (1S,2R)N-allyl-N-benzyloxycarbonylglycine-5-allylproline tert-butyl ester (cis) 17

To alkene 13 (0.87 g, 0.77 mmol) was added a 4M solution of hydrogen chloride in dioxane (4 cm³) at 0° C. The solution was stirred for 1 h at 0° C. then room temperature for 35 min after which time reaction was complete (by tlc). The mixture was cooled to 0° C., neutralized with a saturated solution of aqueous sodium hydrogen carbonate and the product extracted with dichloromethane. Removal of the solvent in vacuo yielded an oil (0.568 g) that was dissolved in dichloromethane (30 cm³). To this was added triethylamine (0.54 cm³, 4.0 mmol), N-allyl-N-benzyloxycarbonylglycine 16 (1.0 g, 4.0 mmol) and 1-(3-dimethylaminopropyl)-3-ethyl-carbodiimide hydrochloride) (EDCI) (0.77 g, 4.0 mmol) at 0° C. and the solution stirred for 16 h. The mixture was washed with saturated aqueous sodium hydrogen carbonate, 2 M aqueous hydrochloric acid, dried (MgSO₄), filtered and the solvent removed to yield an oil (1.7 g) which was purified by chromatography (SiO₂, 5:1, 4:1, 3:1, 2:1, hexane-ethyl acetate,) to afford (i) diene 18 (trans) (0.29 g, 24%) as a colourless oil. Diene 18 was shown to be a 1:1 trans:cis mixture of GlyC(O)—NPro conformers. In addition, restricted rotation about the GlyN-CO carbamate bond was also observed resulting in a 1:1 mixture of conformers: $[\alpha]_D$ −56.1 (c 0.77 in $CH_2Cl_2$); $\delta_H$ (400 MHz; $CDCl_3$; $Me_4Si$) 1.43 [9H, s, $C(CH_3)_3$], 1.46 [9H, s, $C(CH_3)_3$], 1.48 [9H, s, $C(CH_3)_3$], 1.74-2.71 [6H, m, Proβ-$H_2$, Proγ-$H_2$ and $CH_2$(allyl)], 3.54 (0.5H, d, J 16.5, Glyα-$H_AH_B$), 3.58 (0.5H, d, J 16.5, Glyα-$H_AH_B$), 3.84-4.40 [5H, m, Glyα-H, $CH_2$(allyl), Proα-H and Proδ-H], 4.98-5.25 (6H, m, $OCH_2Ph$ and 2 x=$CH_2$), 5.56-5.88 [2H, m, 2×C(H)=$CH_2$] and 7.30-7.37 (5H, m, Ph); $\delta_C$ (100 MHz; $CDCl_3$) 25.8 ($CH_2$, Proβ-C or Proγ-C), 25.9 ($CH_2$, Proβ-C or Proγ-C), 26.16 ($CH_2$, Proβ-C or Proγ-C), 26.2 ($CH_2$, Proβ-C or Proγ-C), 27.8 [$CH_3$, $C(CH_3)_3$], 28.3 ($CH_2$, Proβ-C or Proγ-C), 29.3 ($CH_2$, Proβ-C or Proγ-C), 29.4 ($CH_2$, Proβ-C or Proγ-C), 36.9 [$CH_2$, $CH_2$(allyl)], 37.0 [$CH_2$, $CH_2$(allyl)], 39.0 [$CH_2$, $CH_2$(allyl)], 39.3 [$CH_2$, $CH_2$(allyl)], 47.4 ($CH_2$, Glyα-C), 47.6 ($CH_2$, Glyα-C), 47.8 ($CH_2$, Glyα-C), 48.1 ($CH_2$, Glyα-C), 50.14 [$CH_2$, $NCH_2$(allyl)], 50.18 [$CH_2$, $NCH_2$(allyl)], 50.7 [$CH_2$, $NCH_2$(allyl)], 50.8 [$CH_2$, $NCH_2$(allyl)], 56.9 (CH, Proδ-C), 57.1 (CH, Proδ-C), 58.2 (CH, Proδ-C), 58.3, (CH, Proδ-C), 60.0 (CH, Proα-C), 60.1 (CH, Proα-C), 60.2 (CH, Proα-C), 60.3 (CH, Proα-C), 67.3 ($CH_2$, $OCH_2Ph$), 67.4 ($CH_2$, $OCH_2Ph$), 81.1 [quat., $C(CH_3)_3$], 82.3 [quat., $C(CH_3)_3$], 116.9 ($CH_2$, =$CH_2$), 117.1 ($CH_2$, =$CH_2$), 117.2 ($CH_2$, =$CH_2$), 117.6 ($CH_2$, =$CH_2$), 117.7 ($CH_2$, =$CH_2$), 118.1 ($CH_2$, =$CH_2$), 118.2, ($CH_2$, =$CH_2$), 127.6 (CH, Ph), 127.8 (CH, Ph), 127.9 (CH, Ph), 128.2 (CH, Ph), 128.3 (CH, Ph), 133.3 [CH, C(H)=$CH_2$], 133.4 [CH, C(H)= $CH_2$], 133.6 [CH, C(H)=$CH_2$], 133.8 [CH, C(H)=$CH_2$], 134.9 [CH, C(H)=$CH_2$], 135.0 [CH, C(H)=$CH_2$], 136.5 (quat., Ph), 156.0 (quat., $NCO_2$), 156.37 (quat., $NCO_2$), 156.42, (quat., $NCO_2$), 167.1 (quat., Gly-CO), 167.3 (quat., Gly-CO), 167.4 (quat., Gly-CO), 167.6 (quat., Gly-CO) and 170.9 (quat., Proα-CO), 171.0 (quat., Proα-CO), 171.1 (quat., Proα-CO); m/z (EI+) 442.2455 ($M^+$. $C_{25}H_{34}N_2O_5$ requires 442.2468); (ii) a mixture of 17 and 18 (0.044 g, 4%); (iii) diene 17 (cis) (0.424 g, 36%) as a colourless oil. Diene 17 was shown to be a 1:1 trans:cis mixture of GlyC(O)—NPro conformers. In addition, restricted rotation about the GlyN-CO carbamate bond was also observed resulting in a 1:1 mixture of conformers: $[α]_D$ −39.2 (c 0.57 in $CH_2Cl_2$); $\delta_H$(400 MHz; $CDCl_3$; $Me_4Si$) 1.43 [9H, s, $C(CH_3)_3$], 1.45 [9H, s, $C(CH_3)_3$], 1.47 [9H, s, $C(CH_3)_3$], 1.49 [9H, s, $C(CH_3)_3$], 1.69-2.49 [5.75H, m, Proβ-$H_2$, Proγ-$H_2$ and $CH_2$(allyl)], 2.78-2.84 [0.25H, m, $CH_2$(allyl)], 3.61-4.41 [6H, m, Glyα-$H_2$, $CH_2$(allyl), Proα-H and Proδ-H), 5.02-5.12 (6H, m, $OCH_2Ph$ and 2x=$CH_2$), 5.67-5.87 [2H, m, 2×C(H)= $CH_2$] and 7.29-7.34 (5H, m, Ph); $\delta_C$ (100 MHz; $CDCl_3$) 26.5 ($CH_2$, Proβ-C), 27.7 [$CH_3$, $C(CH_3)_3$], 27.8 [$C_3$, $C(CH_3)_3$], 27.9 [$CH_3$, $C(CH_3)_3$], 29.4 ($CH_2$, Proβ-C or Proγ-C), 29.6 ($CH_2$, Proβ-C or Proγ-C), 29.7 ($CH_2$, Proβ-C or Proγ-C), 37.65 [$CH_2$, $CH_2$(allyl)], 37.7 [$CH_2$, $CH_2$(allyl)], 38.9 [$CH_2$, $CH_2$(allyl)], 47.2 ($CH_2$, Glyα-C), 47.6 ($CH_2$, Glyα-C), 47.7 ($CH_2$, Glyα-C), 48.0 ($CH_2$, Glyα-C), 50.2 [$CH_2$, $NCH_2$(allyl)], 50.3 [$CH_2$, $NCH_2$(allyl)], 50.8 [$CH_2$, $NCH_2$(allyl)], 50.9 [$CH_2$, $NCH_2$(allyl)], 57.8 (CH, Proδ-C), 58.5 (CH, Proδ-C), 60.2, 60.4 (CH, Proα-C), 60.5 (CH, Proα-C), 67.3 ($CH_2$, $OCH_2Ph$), 67.4 ($CH_2$, $OCH_2Ph$), 81.0 [quat., $C(CH_3)_3$], 82.2 [quat., $C(CH_3)_3$], 116.9 ($CH_2$, =$CH_2$), 117.0 ($CH_2$, =$CH_2$), 117.5 ($CH_2$, =$CH_2$), 118.0 ($CH_2$, =$CH_2$), 127.6 (CH, Ph), 127.8 (CH, Ph), 127.9 (CH, Ph), 128.0 (CH, Ph), 128.3 (CH, Ph), 133.3 [CH, C(H)=$CH_2$], 133.4 [CH, C(H)=$CH_2$], 133.5 [CH, C(H)=$CH_2$], 133.6 [CH, C(H)= $CH_2$], 134.1 [CH, C(H)=$CH_2$], 134.3 [CH, C(H)=$CH_2$], 134.8 [CH, C(H)=$CH_2$], 134.9 [CH, C(H)=$CH_2$], 136.5 (quat., Ph), 155.8 (quat., $NCO_2$), 155.9 (quat., $NCO_2$), 156.38 (quat., $NCO_2$), 156.44 (quat., $NCO_2$), 166.95 (quat., Gly-CO), 167.01 (quat., Gly-CO), 167.4 (quat., Gly-CO), 167.5 (quat., Gly-CO), 171.0 (quat., Proα-CO), 172.2 (quat., Proα-CO) and 171.3 (quat., Proα-CO); m/z (EI+) 442.2462 ($M^+$. $C_{25}H_{34}N_2O_5$ requires 442.2468).

(6Z, 9S, 12S)N-Benzyloxycarbonyl-1,4-diaza-12-tert-butoxycarbonyl-2-oxobicyclo[7.3.0]dodec-6-ene 19

To a degassed solution of diene 17 (0.10 g, 0.23 mmol) in dry dichloromethane (56 $cm^3$) was added bis(tricyclohexylphosphine)benzylidineruthenium dichloride (Grubbs's catalyst) (0.018 g, 0.023 mmol) under an atmosphere of nitrogen and the resultant purple solution heated at reflux for 24 h. Further bis(tricyclohexylphosphine)benzylidineruthenium dichloride (0.018 g, 0.023 mmol) was added and refluxing continued for 24 h, then the reaction mixture was cooled to room temperature and dimethyl sulphoxide (0.160 $cm^3$, 2.3 mmol) was added and the orange/brown solution stirred for 24 h. The solvent was removed in vacuo and the residue purified by chromatography ($SiO_2$, 3:1, 2:1, 1:1, hexanes-ethyl acetate,) to give an almost colourless oil which was further purified by chromatography ($C_{18}$ RP silica, 100:0, 9:1, 9:3, 1:1, 1:9, water-acetonitrile,) to give alkene 19 [0.039 g, 42% (60% based on recovered starting material)] as a colourless oil. Alkene 19 existed exclusively as the trans C(O)—NPro conformer. In addition, restricted rotation about the N—CO carbamate bond was also observed resulting in a 1:1 mixture of conformers: $[α]_D$ −118.2 (c 0.34 in $CH_2Cl_2$); $\delta_H$ (400 MHz; $CDCl_3$; $Me_4Si$) 1.46 [9H, s, $C(CH_3)_3$], 1.74 (1H, dd, J 11.8 and 5.7, 10-$H_AH_B$), 1.93 (1H, dd, J 12.5 and 6.5, 1'-$H_AH_B$), 2.11-2.45 (4H, m, 8-$H_2$, 10-$H_AH_B$ and 1'-$H_AH_B$), 3.53 (1H, dd, J 15.7 and 8.0, 5-$H_AH_B$), 4.13-4.37 (4H, m, 3-$H_2$, 9-H and 12-H), 4.50 (1H, d, J 15.4, 5-$H_AH_B$), 5.12-5.29 (2H, m, $OCH_2Ph$), 5.54-5.82 (2H, m, 6-H and 7-H) and 7.31-7.43 (5H, m, Ph); $\delta_C$ (100 MHz; $CDCl_3$) 26.7 ($CH_2$, 11-C), 27.8 [$CH_3$, $C(CH_3)_3$], 34.0 ($CH_2$), 34.2 ($CH_2$), 34.3 ($CH_2$), 34.4 ($CH_2$), 43.9 ($CH_2$, 5-C), 44.5 ($CH_2$, 5-C), 48.5 ($CH_2$, 3-C), 49.5 ($CH_2$, 3-C), 57.2 (CH, 9-C), 57.6 (CH, 9-C), 60.1 (CH, 12-C), 67.6 ($CH_2$, $OCH_2Ph$), 81.2 [quat., $C(CH_3)_3$], 126.8 (CH, 6-C), 126.9 (CH, 6-C), 128.0 (CH, Ph), 128.4 (CH, Ph), 128.7 (CH, Ph), 129.9 (CH, 7-C), 136.3 (quat., Ph), 136.4 (quat., Ph), 155.7 (quat., $NCO_2$), 167.8 (quat., 2-C), 167.9 (quat., 2-C) and 170.7 (quat., 12-CO); m/z (EI+) 414.2157 ($M^+$. $C_{23}H_{30}N_2O_5$ requires 414.2155).

(9S, 12S)-1,4-Diaza-4-tert-butyloxycarbonyl-2-oxo-bicyclo[7.3.0]dodecyl-12-carboxylic acid 20

To a stirred solution of alkene 19 (0.11 g, 0.263 mmol) in tetrahydrofuran (4 $cm^3$) was added platinum oxide (0.006 g, 0.026 mmol) under a flow of nitrogen. The mixture was hydrogenated (1 atm. of hydrogen) for 16 h, filtered over Celite™, and the solvent removed in vacuo. The residue was dissolved in a solution of 30% hydrobromic acid in acetic acid (3 $cm^3$) and stirred at room temperature for 2 h. Removal of the volatiles in vacuo at 40° C. followed by repeated evaporation from methanol:water (3:1) yielded the hydrobromide salt which was dissolved in a solution of saturated sodium hydrogen carbonate (3 $cm^3$). Dioxane (2 $cm^3$) and di-tert-butyl dicarbonate (0.07 g, 0.32 mmol) were added and the resultant suspension was stirred for 24 h, then further di-tert-butyl dicarbonate (0.07 g, 0.32 mmol) was added and stirring continued for a further 48 h. Water (10 $cm^3$) was added, the solution washed with dichloromethane and the aqueous layer was acidified with 2 M aqueous hydrochloric acid and extracted with dichloromethane. The combined organic layers were dried ($Na_2SO_4$), filtered and the solvent removed to yield an oil (0.072 g) that was purified by chromatography (SiO$_2$, 1:1:0.3, hexanes-ethyl acetate:acetic acid) to give acid 20 (0.05 g, 58%) as a colourless oil. Acid 20 existed exclusively as the trans C(O)—NPro conformer. In addition, restricted rotation about the N—CO carbamate bond was also observed resulting in a 72:28 mixture of conformers: [α]$_D$ +3.5-4.4 (c 0.23 in CH$_2$Cl$_2$); δ$_H$ (400 MHz; CDCl$_3$; Me$_4$Si) 1.30-1.48 [11H, m, C(CH$_3$)$_3$, 8-H$_A$H$_B$ and 11-H$_A$H$_B$], 1.63-1.79 (5H, m, 8-H$_A$H$_B$, 6-H$_2$ and 7-H$_2$), 2.01-2.07 (1H, m, 11-H$_A$H$_B$), 2.12-2.32 (2H, m, 10-H$_2$), 2.62-2.85 (1H, m, 5-H$_A$H$_B$), 3.73-3.83 (1.28H, 3-H$_A$H$_B$ and 5-H$_A$H$_B$*), 4.0 (0.72H, br d, J 14.2, 5-H$_A$H$_B$), 4.20-4.32 (1H, m, 9-H), 4.41* (0.28H, d, J 8.0, 12-H), 4.50 (0.72H, d, J 8.8, 12-H), 4.57 (0.72H, d, J 17.8, 3-H$_A$H$_B$), 4.69* (0.28H, d, J 16.5, 3-H$_A$H$_B$) and 8.40 (1H, br s, OH); δ$_C$ (100 MHz; CDCl$_3$) 22.1 (CH$_2$, 7-C), 22.6* (CH$_2$, 7-C), 25.1 (CH$_2$, 11-C), 25.7* (CH$_2$, 11-C), 26.6 (CH$_2$, 6-C), 28.1 [CH$_3$, C(CH$_3$)$_3$], 28.3* [CH$_3$, C(CH$_3$)$_3$], 32.5 (CH$_2$, 10-C), 32.7* (CH$_2$, 10-C), 35.9* (CH$_2$, 8-C), 36.3 (CH$_2$, 8-C), 50.3* (CH$_2$, 5-C), 51.8 (CH$_2$, 5-C), 54.9* (CH$_2$, 3-C), 55.4 (CH, 9-C), 56.0* (CH, 9-C), 56.3 (CH$_2$, 3-C), 60.5* (CH, 12-C), 60.8 (CH, 12-C), 80.6* [quat., C(CH$_3$)$_3$], 81.0 [quat., C(CH$_3$)$_3$], 155.2 (quat., NCO$_2$), 155.5* (quat., NCO$_2$), 169.5* (quat., 2-C), 169.8 (quat., 2-C), 174.9 (quat., 12-CO) and 175.1* (quat., 12-CO); m/z (EI+) 326.1837 (M$^+$. C$_{16}$H$_{26}$N$_2$O$_5$ requires 326.1842).

(2S, 9'R, 12'S)-2-{[(1',4'-Diaza-2'-oxobicyclo[7.3.0]dodecyl)-12'-carbonyl]amino}-1,5-pentanedioic acid trifluoroacetate salt 22

Bis(2-oxo-3-oxazolidinyl)phosphinic chloride (BoP-Cl) (0.057 g, 0.225 mmol) was added to a solution of acid 10 (0.05 g, 0.15 mmol), L-glutamic acid di-tent-butyl ester hydrochloride 21 (0.062 g, 0.21 mmol) and triethylamine (0.061 cm$^3$, 0.44 mmol) in dichloromethane (5 cm$^3$) at 0° C. The mixture was stirred for 17 h, washed with saturated aqueous sodium hydrogen carbonate, 2 M aqueous hydrochloric acid, dried (Na$_2$SO$_4$), filtered and the solvent removed to yield an oil (0.108 g) which was purified by chromatography (SiO$_2$, 1:1, 1:2, 1:3, hexane-ethyl acetate) to afford an inseparable mixture (0.074 g) of the desired amide contaminated with a glutamate/bis(2-oxo-3-oxazolidinyl)phosphinic chloride adduct. The mixture was dissolved in dichloromethane (5 cm$^3$), trifluoroacetic acid (2 cm$^3$) was added and the solution stirred for 4 h. Further trifluoroacetic acid (1 cm$^3$) was then added and stirring continued for 2 h. The volatiles were removed in vacuo, the residue suspended in water and filtered through a plug of cotton wool. The filtrate was subsequently purified by RP-HPLC [water (0.05% trifluoroacetic acid):acetonitrile, 90:10, 13 ml min$^{-1}$] to afford trifluoroacetate 22 (0.039 g, 55% from 20) as a white solid after tituration from diethyl ether/toluene. Macrocycle 22 existed exclusively as the trans C(O)—NPro conformer: mp 50-100° C.; [α]$_D$ −22.3 (c 0.35 in MeOH); δ$_H$ (400 MHz; CDCl$_3$; Me$_4$Si) 1.68-2.04 (9H, m, 7'-H$_2$, 6'-H$_2$, 3'-H$_A$H$_B$, 8'-H$_A$H$_B$ and 11'-H$_A$H$_B$), 2.19-2.26 (2H, 8'-H$_A$H$_B$ and 3'-H$_A$H$_B$), 2.42-2.48 (1H, m, 11'-H$_A$H$_B$), 2.50-2.58 (2H, m, 4-H$_2$), 3.04 (1H, td, J 11.2 and 2.5, 5'-H$_A$H$_B$), 3.33 (1H, dt, J 14.1 and 4.9, 5'-H$_A$H$_B$), 3.82 (1H, d, J 14.1, 3'-H$_A$H$_B$), 4.32 (1H, d, J 14.0, 3'-H$_A$H$_B$), 4.38-4.45 (2H, m, 9'-H and 2-H) and 4.59 (1H, dd J 9.6 and 1.8, 12'-H); δ$_C$ (100 MHz; CDCl$_3$) 25.6 (CH$_2$, 6'-C or 7'-C), 26.0 (CH$_2$, 6'-C or 7'-C), 28.1 (CH$_2$, 3-C), 29.9 (CH$_2$, 11'-C), 32.3 (CH$_2$, 4-C), 34.0 (CH$_2$, 10'-C or 8'-C), 35.2 (CH$_2$, 10'-C or 8'-C), 46.9 (CH$_2$, 5'-C), 48.7 (CH$_2$, 3'-C), 54.3 (CH, 2-C), 62.9 (CH, 12'-C), 64.6 (CH, 9'-C), 118.6 (quat., q, J 291, CF$_3$), 165.1 (quat., q, J 36.2, CF$_3$CO$_2$H), 167.9 (quat., 2'-C), 175.9 (quat., 12'-CO), 177.1 (quat., 1-C), and 179.4 (quat., 5-C); m/z (FAB+) 356.1824 [MH(free base)$^+$. C$_{16}$H$_{26}$N$_3$O$_6$ requires 356.1822].

Example 3

Synthesis of (3S, 8R, 10S, 13S) 3-amino-1,11-diaza-8,10-carboxy-2,12-oxobicyclo[13.3.0]hexadecane trifluoroacetate Scheme 1 Reagents, conditions and yields:

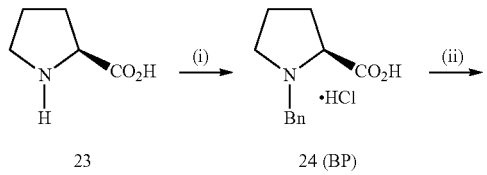

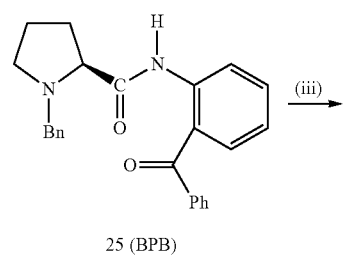

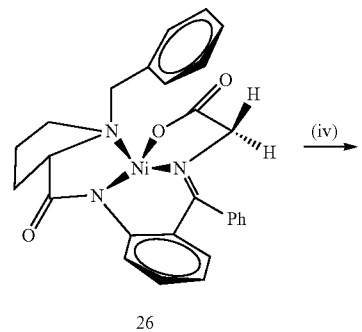

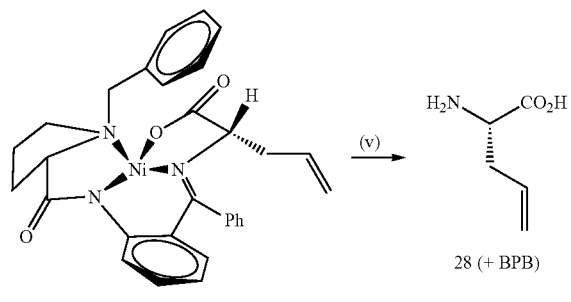

(i) KOH, BnCl, $^i$PrOH, 40° C., 5.5 h (78%);
(ii) SOCl$_2$, CH$_2$Cl$_2$, Et$_3$N -30° C., then 2-aminobenzophenone, RT, overnight (43%);
(iii) KOH, glycine, Ni(NO$_3$)$_2$•6H$_2$O, 60° C., 75 min (78%);
(iv) NaOH, allyl bromide, CH$_3$CN, 2.5 h, RT (68%);
(v) 2M aq. HCl, MeOH, 80° C. 1 h, (84%).

29

Scheme 2 Reagents, conditions and yields:

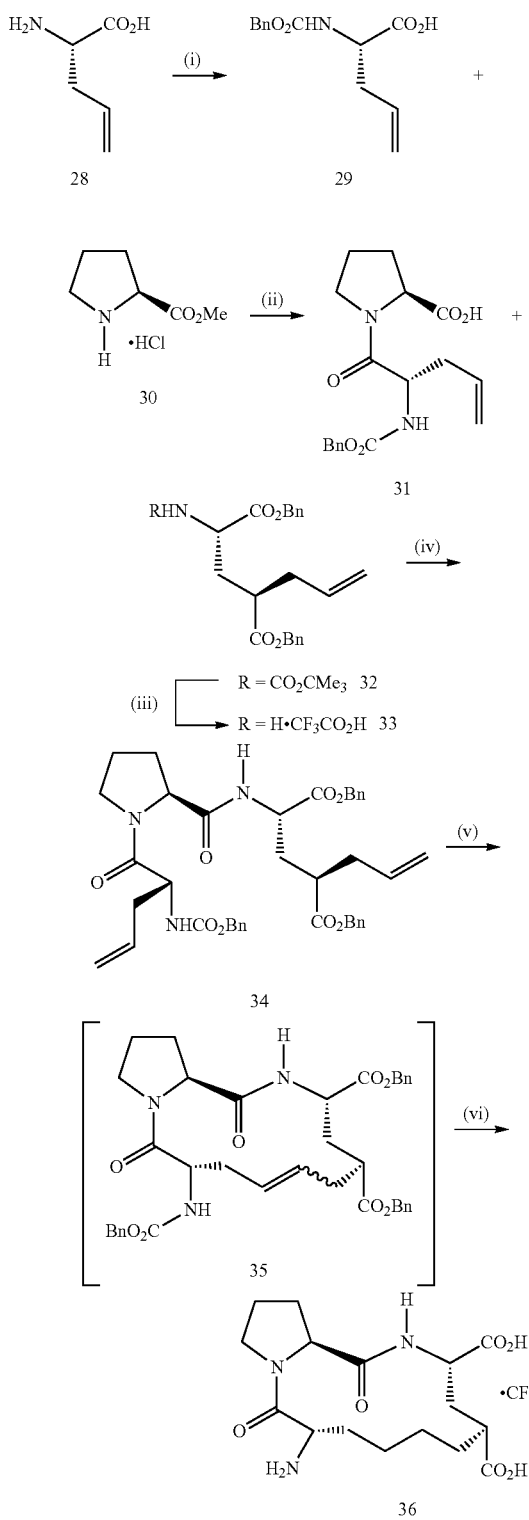

(i) BnOCOCl, Na$_2$CO$_3$, H$_2$O/dioxane, 0° C. to RT, 17 h (53%);
(ii) DCC, HOBt, Et$_3$N, CH$_2$Cl$_2$, 0° C. to RT, overnight, then 1M aq. NaOH, dioxane, RT, 24 h (64% over 2 steps);
(iii) TFA, CH$_2$Cl$_2$, 0° C. 2 h
(iv) 31, EtOCOCl, Et$_3$N, CH$_2$Cl$_2$, 0° C., 40 min, then 33 0° C. to RT overnight (60%);
(v) Grubbs's catalyst, CH$_2$Cl$_2$, reflux, 48 h then DMSO, 24 h;
(vi) 10% Pd/C, H$_2$, THF/H$_2$O (4:1), RT, 21 h or 10% PtO$_2$, THF, RT, 16 h then 10% Pd/C, H$_2$, MeOH/H$_2$O (4:1), RT, 5 h (58% from 34).

30

N-Benzyl-L-proline hydrochloride 24 (BP)

A suspension L-proline 23 (6.0 g, 52.1 mmol) and postassium hydroxide (85%, 11.1 g, 198 mmol) in isopropanol (50 cm$^3$) was heated at 40° C. until mostly dissolved. Benzyl chloride (9.2 cm$^3$, 79.7 mmol) was added dropwise during which the internal temperature rose to 70° C. The addition was stopped, the reaction flask placed in an ice bath until an internal temperature of 40° C. had been obtained, and then the addition continued at 40° C. The milky-white suspension was stirred at 40° C. for 5.5 h, cooled to room temperature and neutralised with 32% hydrochloric acid until pH=4 had been obtained. Chloroform (50 cm$^3$) was added, the suspension stored overnight at 0° C. and the white solid was removed by filtration. The filtrate was concentrated in vacuo, suspended in acetone, the solid filtered and air dried to give BP 24 (9.842 g, 78%) as a white solid: mp 173-176° C. (dec) (lit., 174-175, free base) $[\alpha]_D$, −22.9 (c 0.20 in H$_2$O) (lit.,[1] −25.8 c 1 in EtOH, free base); $\delta_H$ (300 MHz; D$_2$O) 1.91-2.21 (3H, Proγ-H$_2$, Proβ-H$_A$H$_B$), 2.47-2.60 (1H, m, Proβ-H$_A$H$_B$), 3.27-3.36 (1H, m, Proδ-H$_A$H$_B$), 3.60-3.67 (1H, m, Proδ-H$_A$H$_B$), 4.14 (1H, dd, J 9.3 7.0, Proα-H), 4.37 (1H, d, J 12.9, NCH$_A$H$_B$Ph), 4.44 (1H, d, J 12.9, NCH$_A$H$_B$Ph) and 7.45-7.54 (5H, m, Ph); $\delta_C$ (75 MHz; D$_2$O) 22.4 (CH$_2$, Proγ-C), 28.4 (CH$_2$, Proβ-C), 54.6 (CH$_2$, Proδ-C), 58.3 (CH$_2$, NCH$_2$Ph), 67.1 (CH, Proα-C), 129.0, 130.4 (CH, Ph), 129.6 (quat., Ph), 129.9 (CH, Ph) and 172.4 (quat., Proα-CO).

(S)-2-[N-(N'-Benzylprolyl)amino]benzophenone 25 (BPB)

To an opaque solution of BP 24 (10.567 g, 43.84 mmol) and triethylamine (5.9 cm$^3$, 43.84 mmol) in dry dichloromethane (70 cm$^3$) was added thionyl chloride (4.3 cm$^3$, 58.5 mmol) over 5 min at −30° C. The resultant orange suspension was allowed to warm to −10° C. over 30 min, stirred for 30 min at this temperature and cooled to −30° C. A solution of 2-aminobenzophenone (5.76 g, 29.2 mmol) in dry dichloromethane (30 cm$^3$) was added over 5 min and the yellow-orange solution stirred at room temperature overnight. The mixture was cooled to 0° C. and a solution of sodium carbonate (9.1 g) in water (50 cm$^3$) was added carefully. After the evolution of gas had ceased, the organic layer was removed, the aqueous layer extracted with dichloromethane, and combined extracts dried (MgSO$_4$). Evaporation of the solvent and initial purification by chromatography (silica gel, hexanes:ether, 4:1, 3:1, 1:1) [to remove most of 2-aminobenzophenone] gave a solid (6.405 g) which by $^1$H NMR contained 10% 2-aminobenzophenone. Recrystallisation from boiling hexanes afforded BPB 25 (5.218 g, 46%) as yellow crystals: mp 99-102° C. (lit., 101-102° C.); $[\alpha]_D$ −129.1 (c 0.12 in MeOH) (lit., −134 c 1 in MeOH); $\delta_H$ (300 MHz; CDCl$_3$; Me$_4$Si) 1.78-2.04 (3H, Proγ-H$_2$, Proβ-H$_A$H$_B$), 2.21-2.47 (2H, m, Proβ-H$_A$H$_B$, Proδ-H$_A$H$_B$), 3.22-3.24 (1H, m, Proδ-H$_A$H$_B$), 3.34 (1H, dd, J 10.1 and 4.6, Proα-H), 3.61 (1H, d, J 12.9, NCH$_A$H$_B$Ph), 3.94 (1H, d, J 12.9, NCH$_A$H$_B$Ph), 7.08-7.65 (12H, m, Ph), 7.81 (2H, d, J 8.2, Ph) and 11.6 (1H, s, N—H); (75 MHz; CDCl$_3$) 24.1 (CH$_2$, Proγ-C), 30.9 (CH$_2$, Proβ-C), 53.8 (CH$_2$, Proδ-C), 59.8 (CH$_2$, NCH$_2$Ph), 68.2 (CH, Proα-C), 121.4, 122.7 (CH, Ph), 125.2 (quat., Ph), 127.1, 128.1, 128.2, 129.0, 130.0, 132.4, 132.5, 133.3 (CH, Ph), 138.0, 138.5, 139.0 (quat., Ph), 174.6 (quat., Pro-CON) and 198.0 (quat., Ph$_2$CO).

Gly-Ni-BPB complex 26

A solution of potassium hydroxide (4.56 g, 81.3 mmol) in methanol (30 cm$^3$) was added to a suspension of BPB 25 (4.46 g, 11.61 mmol), glycine (4.36 g, 58.07 mmol) and nickel nitrate hexahydrate (6.93 g, 23.2 mmol) at 50° C. under an atmosphere of nitrogen. The mixture was heated at 60° C. for 75 min, cooled to room temperature and acetic acid (4.65 cm$^3$, 81.3 mmol) added. Water (150 cm$^3$) was then added and the mixture allowed to stand at room temperature for 2 h. Extraction of the product with dichloromethane yielded a blood-red syrup which was purified by chromatography (silica gel, dichloromethane:acetone, 7:1, 6:1, 4:1, 3:1, 2:1) to give the crude product which was recrystallised from ethyl acetate at −20° C. to give complex 26 (4.377 g, 78%) as a red solid: mp 226-228° C. (lit., 208-212° C.); [α]$_D$+2010.6 (c 0.104 in MeOH) (lit., +2006 c 0.1 in MeOH); δ$_H$ (400 MHz; CDCl$_3$; Me$_4$Si) 2.03-2.20 (2H, Proγ-H$_A$H$_B$, Proδ-H$_A$H$_B$,), 2.38-2.49 (1H, m, Proβ-H$_A$H$_B$), 2.55 (1H, m, Proβ-H$_A$H$_B$), 3.30-3.42 (1H, m, Proγ-H$_A$H$_B$), 3.48 (1H, dd, J 10.7 and 5.4, Proα-H), 3.66-3.75 (3H, m, Proδ-H$_A$H$_B$, NCH$_A$H$_B$Ph, Glyα-H$_A$H$_B$), 3.79 (1H, d, J 20.1, Glyα-H$_A$H$_B$), 4.49 (1H, d, J 12.9, NCH$_A$H$_B$Ph), 6.71 (1H, t, J 7.2, Ph), 6.81 (1H, dd, J 8.2 and 1.5, Ph), 6.93-7.00 (1H, m, Ph), 7.11 (1H, br d, J 7.2, Ph), 7.20-7.24 (1H, m, Ph), 7.32 (1H, t, J 7.5, Ph), 7.44 (2H, t, J 7.52, Ph), 7.51-7.57 (3H, m, Ph), 8.09 (2H, d, J 7.4, Ph) and 8.30 (1H, d, J 8.6, Ph); δ$_C$ (100 MHz; CDCl$_3$) 23.6 (CH$_2$, Proγ-C), 30.6 (CH$_2$, Proβ-C), 57.4 (CH$_2$, Proδ-C), 61.2 (CH$_2$, Glyα-C), 63.1 (CH$_2$, NCH$_2$Ph), 68.9 (CH, Proα-C), 120.8, 124.2 (CH, Ph), 125.1 (quat., Ph), 125.6, 126.2, 128.8, 129.0, 129.3, 129.5, 129.6, 131.6, 132.1, 133.1 (CH, Ph), 133.3, 134.5, 142.5 (quat., Ph), 171.5 (quat., C=N), 177.7 (quat., Glyα-CO) and 181.3 (quat., Pro-CON).

AllylGly-Ni-BPB complex 27

Powdered sodium hydroxide (0.733 g, 18.34 mmol) and allyl bromide (2.06 cm$^3$, 22.0 mmol) was added to a stirred solution of complex 26 (3.6 g, 7.33 mmol) in dry acetonitrile (160 cm$^3$) under a nitrogen atmosphere. The mixture was stirred for 2.5 h at room temperature, 0.1 M aqueous hydrochloric acid (100 cm$^3$) added and the product extracted with dichloromethane. The combined organic layers were dried (MgSO$_4$), the solvent removed and the residue purified by chromatography (silica gel, dichloromethane:acetone, 2:1) to give a mixture of diastereomers (1.468 g) and one diastereomer (2.174 g). Both fractions were recrystallised from ethyl acetate at −20° C. to give the desired compound (1.9 g); further compound was obtained from crystallization from the mother liquors (0.766 g) to give allyl complex 27 (2.676 g, 68%) as a red solid (single diastereomer): mp 216-219° C. (lit., 217° C.); δ$_H$ (300 MHz; CDCl$_3$; Me$_4$Si) 2.0-2.16 (2H, m, Proγ-H$_A$H$_B$, Proδ-H$_A$H$_B$,), 2.36-2.55 [3H, m, Proβ-H$_A$H$_B$, CH$_2$(allyl)], 2.74-2.83 (1H, m, Proβ-H$_A$H$_B$), 3.41-3.61 (4H, m, Proγ-H$_A$H$_B$, Proα-H, Proδ-H$_A$H$_B$, NCH$_A$H$_B$Ph), 4.01 (1H, dd, J 6.3 and 4.1, Glyα-H), 4.42 (1H, d, J 12.6, NCH$_A$H$_B$Ph), 5.17 (1H, d, J 17, =CH$_A$H$_B$), 5.38 (1H, d, J 10, =CH$_A$H$_B$), 6.36-6.50 (1H, m, C(H)=CH$_2$), 6.61-6.68 (2H, m, Ph), 6.94 (1H, d, J 7.0, Ph), 7.11-7.54 (8H, m, Ph), 8.03 (2H, d, J 7.4, Ph) and 8.17 (1H, d, J 8.7, Ph); δ$_C$ (75 MHz; CDCl$_3$) 23.3 (CH$_2$, Proγ-C), 30.8 (CH$_2$, Proβ-C), 38.5 [CH$_2$, CH$_2$(allyl)], 56.9 (CH$_2$, Proδ-C), 63.1 (CH$_2$, NCH$_2$Ph), 70.27, 70.34 (CH, Proα-C, Glyα-C), 119.7 (CH$_2$, =CH$_2$), 120.6, 123.6 (CH, Ph), 126.4 (quat., Ph), 127.0, 127.7, 128.8, 128.9, 129.0, 129.8, 131.5, 132.1, 132.2, (CH, C(H)=CH$_2$, Ph), 133.2, (quat., Ph), 133.3 (CH, Ph), 133.9, 142.5 (quat., Ph), 170.8 (quat., C=N), 178.8 (quat., Glyα-CO) and 180.3 (quat., Pro-CON).

(S)-Allylglycine 28

A mixture of ally complex 27 (2.520 g, 4.69 mmol) and 2 M aqueous hydrochloric acid (54 cm$^3$) in methanol (78 cm$^3$), was heated (oil bath 80° C.) for 1 h. The light green solution was cooled to room temperature and 28% ammonia solution was added until pH=9-10. The aqueous layer was extracted with dichloromethane to recover BPB (1.82 g, 100% recovery) and the aqueous layer was concentrated in vacuo to afford a blue solid that was purified by ion exchange chromatography (Dowex 50W×8-100, H$_2$O, then 5% ammonia solution). The ammonia fractions were combined, evaporated to dryness, suspended in toluene and concentrated in vacuo (2×) to yield a solid that was dried on a freeze drier to give allylglycine 28 (0.455 g, 84%) as a white powder: mp 195-190° C. (dec.) (lit., 208° C.); [α]$_D$ −40.5 (c 0.11 in H$_2$O) (lit., −42.7 c 4 in H$_2$O); δ$_H$ (400 MHz; D$_2$O) 2.62-2.76 [2H, m, CH$_2$(allyl)], 3.87 (1H, dd, J 6.9 and 5.4, Glyα-H), 5.30-5.35 (2H, m, =CH$_2$) and 5.58-5.88 (1H, m, C(H)=CH$_2$); δ$_C$ (100 MHz; D$_2$O) 34.7 [CH$_2$, CH$_2$(allyl)], 53.8 (CH, Glyα-C), 120.4 (CH$_2$, =CH$_2$), 131.2 (CH, C(H)=CH$_2$) and 174.0 (quat., Glyα-CO).

(S)-N-Benzyloxycarboylallylglycine 29

A solution of benzyl chloroformate (0.135 cm$^3$, 0.956 mmol) in dioxane (1 cm$^3$) was added to a solution of allylglycine 28 (0.1 g, 0.870 mmol) and sodium carbonate (0.275 g, 2.60 mmol) in water (5 cm$^3$) at 0° C. The solution was allowed to warm to room temperature over 2 h, then stirred for a further 17 h. The aqueous layer was washed with ether, acidified with 31% hydrochloric acid to pH=1 and extracted with ethyl acetate. The pooled organic layers were dried (MgSO$_4$) and the solvent removed in vacuo to give carbamate 7 (0.114 g, 53%) as an opaque oil. Carbamate 29 was shown to be a 74:26 mixture of rotamers: δ$_H$ (300 MHz; CDCl$_3$; Me$_4$Si) 2.52-2.67 [2H, m, CH$_2$(allyl)], 4.37* (0.26H, br s, Glyα-H), 4.46-4.52 (0.76H, m, Glyα-H), 5.08-5.18 (4H, m, OCH$_2$Ph, =CH$_2$) 5.48 (0.74H, d, J 7.9, N—H), 5.69-5.79 (1H, m, C(H)=CH$_2$), 6.34 (0.26H, br d, J 5.6, N—H), 7.26-7.34 (5H, m, Ph) and 9.46 (1H, br s, OH); δ$_C$ (75 MHz; CDCl$_3$) 36.4 [CH$_2$, CH$_2$(allyl)], 53.2 (CH, Glyα-C), 53.9* (CH, Glyα-C), 67.2 (CH$_2$, OCH$_2$Ph), 67.7* (CH$_2$, OCH$_2$Ph), 119.6 (CH$_2$, =CH$_2$), 128.1, 128.3, 128.6 (CH, Ph), 131.9 (CH, C(H)=CH$_2$), 136.1 (quat., Ph), 156.1 (quat., NCO$_2$) and 176.0 (quat., Glyα-CO).

(S)-N-Benzyloxycarboylallylglycyl-L-proline 31

N,N-Dicyclohexylcarbodiimide (0.103 g, 0.504 mmol) was added to a solution of carbamate (0.114 g, 0.457 mmol), proline methyl ester hydrochloride 30 (0.083 g, 0.504 mmol), N-hydroxybenzotriazole (0.068 g, 0.504 mmol) and triethylamine (0.071 cm$^3$, 0.504 mmol) in dichloromethane (12 cm$^3$) at 0° C. The mixture was stirred overnight, stored at 0° C. for 3 h and filtered thorough Celite™. The reaction mixture was washed with 2 M aqueous hydrochloric acid, saturated sodium hydrogen carbonate solution, dried (MgSO$_4$) and the solvent removed to yield an oil which was purified by chromatography (silica gel, hexanes:ethyl acetate, 2:1, 1:1) to afford protected dipeptide (0.141 g) that was suspended in dioxane (4 cm$^3$). 1M Aqueous sodium hydroxide (1.95 cm$^3$, 1.95 mmol) was added and the mixture stirred at room temperature for 24 h. Water (5 cm$^3$) was added and the mixture extracted with dichloromethane. The aqueous layer was acidified with 31% hydrochloric acid and the product extracted with dichloromethane. The organic layers were pooled, washed with brine, dried (MgSO$_4$) and the solvent removed to afford an oil (0.152 g) that was purified by chromatography (silica gel, hexane:ethyl acetate, 3:1, then hexane:ethyl acetate:acetic acid, 3:1:0.4, 2:1:0.3) to give acid 31

(0.102 g, 64%) as a colourless oil. Acid 31 was shown to be a 87:13 trans:cis mixture of conformers by $^1$H NMR analysis (the ratio was estimated by integration of multiplets at δ3.33-3.50 and 3.62-3.77 assigned to the Proδ-H$_2$ atoms of the minor and major conformers respectively): [α]–91 (c 0.26 in CH$_2$Cl$_2$); δ$_H$ (300 MHz; CDCl$_3$; Me$_4$Si) 1.65* (0.13H, br s, Proβ-H$_A$H$_B$), 1.84-2.25 (3.87H, m, Proβ-H$_A$H$_B$,* Proβ-H$_2$, Proγ-H$_2$), 2.34-2.53 [2H, m, CH$_2$(allyl)], 3.33-3.50* (0.26H, m, Proδ-H$_2$), 3.62-3.77 (1.74H, m, Proδ-H$_2$), 4.30-4.58 (2H, m, Proα-H, Glyα-H), 4.93-5.15 (4H, m, OCH$_2$Ph, =CH$_2$) 5.71-5.85 (1H, m, C(H)=CH$_2$), 6.0 (0.13H, br d, J 8.5, N—H), 6.06* (0.13H, br d, J 8.7, N—H), 7.26-7.31 (5H, m, Ph) and 8.01 (1H, br s, OH); δ$_C$ (75 MHz; CDCl$_3$) 22.1* (CH$_2$, Proγ-C), 24.8 (CH$_2$, Proγ-C), 28.6 (CH$_2$, Proβ-C), 31.2* (CH$_2$, Proβ-C), 36.6 [CH$_2$, CH$_2$(allyl)], 37.8* [CH$_2$, CH$_2$(allyl)], 46.7* (CH$_2$, Proδ-C), 47.3 (CH$_2$, ProδC), 52.1 (CH, Glyα-C), 52.3* (CH, Glyα-C), 59.2 (CH, Proα-C), 66.6 (CH$_2$, OCH$_2$Ph), 67.1* (CH$_2$, OCH$_2$Ph), 119.1 (CH$_2$, =CH$_2$), 127.9, 128.0, 128.4, 128.5 (CH, Ph), 132.4 (CH, C(H)=CH$_2$), 136.1* (quat., Ph), 136.3 (quat., Ph), 156.1 (quat., NCO$_2$), 170.8* (quat., Glyα-CO), 171.4 (quat., Glyα-CO) and 174.6 (quat., Proα-CO); m/z (EI+) 346.1527 (M$^+$. C$_{18}$H$_{22}$N$_2$O$_5$ requires 346.1529).

(S)-N-Benzyloxycarboylallylglycyl-L-prolyl-L-γ(R)-allylglutamic acid dibenzyl ester 34

Alkene 32 (0.217 g, 0.464 mmol) was dissolved in dichloromethane (7 cm$^3$), cooled to 0° C. and trifluoroacetic acid (1.5 cm$^3$) was added. After stirring for 2 h the volatiles were removed in vacuo to yield trifluoroacetate 33 as an off white solid. To an ice cold solution of acid 31 (0.134 g, 0.387 mmol) and triethylamine (0.062 cm$^3$, 0.461 mmol) in dichloromethane (10 cm$^3$) was added dropwise ethyl chloroformate (0.045 cm$^3$, 0.464 mmol). The solution was stirred at 0° C. for 40 min then an ice cold solution of 33 and triethylamine (0.062 cm$^3$, 0.464 mmol) in dichloromethane (5 cm$^3$) was added dropwise and the mixture stirred overnight. The solution was subsequently washed with 2 M aqueous hydrochloric acid, saturated sodium hydrogen carbonate solution, dried (MgSO$_4$) and the solvent removed to yield an oil which was purified by chromatography (silica gel, hexane:ethyl acetate, 2:1) to give protected tripeptide 34 (0.162 g, 60%) as a colourless oil. Tripeptide 34 was shown to be a 89:11 trans:cis mixture of conformers by $^1$NMR analysis (the ratio was estimated by integration of the doubles at δ 8.04 and 7.10 assigned to the GluN—H atoms of the minor and major conformers respectively): [α]$_{D-31.2}$ (c 0.462 in CH$_2$Cl$_2$); δ$_H$ (400 MHz; CDCl$_3$; Me$_4$Si) 1.90-1.99 (2H, m, Proβ-H$_A$H$_B$, Proγ-H$_A$H$_B$), 2.06-2.13 (3H, m, Proγ-H$_A$H$_B$, Gluβ-H$_2$), 2.19-2.26 (1H, m, Proβ-H$_A$H$_B$), 2.33-2.42 [3H, m, CH$_2$(allyl), CH$_A$CH$_B$(allyl)], 2.47-2.54 (1H, m, CH$_A$CH$_B$(allyl)], 2.63 (1H, p, J 6.7, Gluγ-H), 3.56-3.72 (2H, m, Proδ-H$_2$), 4.18* (0.11H, q, J 6.2, Glyα-H), 4.38* (0.11H, d, J 7.7, Proα-H), 4.54-4.66 (2.78H, Glyα-H, Proα-H), Gluα-H), 4.86-5.18 (10H, m, 3×OCH$_2$Ph, 2×=CH$_2$), 5.60-5.81 (3H, m, 2×C(H)= CH$_2$, GlyN—H), 7.10 (0.89H, d, J 7.4, GluN—H), 7.26-7.39 (15H, m, Ph) and 7.10* (0.11H, d, J 7.9, GluN—H); δ$_C$(100 MHz; CDCl$_3$) 22.0* (CH$_2$, Proγ-C), 24.9 (CH$_2$, Proγ-C), 27.5 (CH$_2$, Proβ-C), 31.3* (CH$_2$, Proβ-C), 31.4* (CH$_2$, GluβC), 32.9 (CH$_2$, GluβC), 35.65* [CH$_2$, CH$_2$(allyl)], 35.71* [CH$_2$, CH$_2$(allyl)], 35.9 [CH$_2$, CH$_2$(allyl)], 36.9 [CH$_2$, CH$_2$(allyl)], 41.0 (CH, Gluγ-C), 41.9* (CH, Gluγ-C), 46.9* (CH$_2$, Proδ-C), 47.3 (CH$_2$, Proδ-C), 50.7 (CH, Gluα-C), 51.3* (CH, Gluα-C), 51.8 (CH, Glyα-C), 52.4* (CH, Glyα-C), 59.9 (CH, Proα-C), 60.8* (CH, Proα-C), 66.31* (CH$_2$, OCH$_2$Ph), 66.4 (CH$_2$, OCH$_2$Ph), 66.8 (CH$_2$, OCH$_2$Ph), 67.0* (CH$_2$, OCH$_2$Ph), 67.2 (CH$_2$, OCH$_2$Ph), 117.7, 119.0, 119.8* (CH$_2$, =CH$_2$), 127.9, 128.0, 128.14, 128.22, 128.24, 128.31, 128.42, 128.46, (CH, Ph), 131.7,* 132.4, 134.2 (CH, C(H)= CH$_2$), 135.2, 135.3,* 135.7, 136.0,* 136.2 (quat., Ph), 155.8 (quat., NCO$_2$), 156.2* (quat., NCO$_2$), 170.7* (quat., CO), 170.9 (quat., CO) 171.2 (quat., CO), 171.5 (quat., CO), 171.6* (quat., CO), 174.3* (quat., Gluγ-CO) and 174.4 (quat., Gluγ-CO); m/z (EI+) 695.3170 (M$^+$C$_{40}$H$_{45}$N$_3$O$_8$ requires 695.3207).

(3S, 8R, 10S, 13S) 3-Amino-1,11-diaza-8,10-carboxy-2,12-oxobicyclo[13.3.0]hexadecane trifluoroacetate 36

To a solution of protected tripeptide 34 (0.041 g, 0.0589 mmol) in dry dichloromethane (7.5 cm$^3$) was added bis(tricyclohexylphosphine)-benzylidineruthenium dichloride (0.015 g, 0.0126 mmol) under an atmosphere of nitrogen. The purple solution was heated at reflux for 48 h, cooled to room temperature and dimethyl sulphoxide (0.045 cm$^3$, 0.63 mmol) added. The orange-brown solution was stirred for 24 h, filtered through a short plug of silica gel (eluting with hexanes:ethyl acetate, 1:3), and purified by chromatography (C$_{18}$ RP silica, water:acetonitrile, 20%-70%) to give the metathesis product 35 (48 mg) and other unidentified product(s) as a yellow oil, [m/z (FAB+) 668.2977 (MH$^+$. C$_{38}$H$_{42}$N$_3$O$_8$ requires 668.2972]. Metathesis product was divided into 2 samples (~25 mg each); the first sample was dissolved in tetrahydrofuran/water (4:1, 5 cm$^3$) and 10 wt. % palladium on activated carbon (0.008 g, 0.00749 mmol) was added under an atmosphere of nitrogen. To the reaction flask was fitted a balloon of hydrogen and stirred for 21 h at room temperature. The reaction mixture was filtered through a pad of Celite™, washed with methanol/water (4:1) and concentrated in vacuo to yield a film. The second sample was dissolved in tetrahydrofuran (3 cm$^3$) and platinum (IV) oxide (0.00078 g, 0.0034 mmol) added was added under an atmosphere of nitrogen. To the reaction flask was fitted a balloon of hydrogen and stirred for 16 h at room temperature. The reaction mixture was filtered through a pad of Celite™, washed with methanol: and concentrated in vacuo to yield a film that was dissolved in methanol:water (4:1, 5 cm$^3$) and 10 wt. % palladium on activated carbon (0.008 g 0.00749 mmol) was added under an atmosphere of nitrogen. To the reaction flask was fitted a balloon of hydrogen and stirred for 5 h at room temperature. The reaction mixture was filtered through a pad of Celite™, washed with methanol/water (4:1) and concentrated in vacuo to yield a film. Both samples were combined, purified by RP HPLC [10% acetonitrile:90% water (containing 0.05% trifluoroacetic acid) then 80:20, 70:30] and dried on a freeze drier to give 36 (0.016 g, 58% from 34) as a white solid. 36 existed exclusively as the trans conformer: mp 150-240° C.; [α]$_D$ –39.4 (c 0.0864 in water); δ$_H$ (400 MHz; D$_2$O) 1.20-1.62 (6H, m, 5-H$_2$, 14-H$_2$, 7-H$_2$), 1.81-1.90 (1H, m, 4-H$_A$H$_B$), 2.04-2.36 (7H, m, 4-H$_A$H$_B$, 9-H$_2$, 6-H$_2$, 15-H$_2$), 2.43 (1H, br t, J 6.2, 8-H), 3.68-3.79 (2H, m, 16-H$_2$), 4.48-4.49 (1H, m, H-3) and 4.51-4.55 (1H, m, 10-H) [13-H obscured by HOD]; δ$_C$ (100 MHz; D$_2$O) 18.2 (CH$_2$, 5-C), 23.9 (CH$_2$, 14-C), 24.2 (CH$_2$, 15-C), 26.0 (CH$_2$, 6-C), 26.8 (CH$_2$, 4-C), 28.0 (CH$_2$, 7-C), 30.3 (CH$_2$, 9-C), 38.2 (CH, 8-C), 47.1 (CH$_2$, 16-C), 50.6 (CH, 10-C), 50.9 (CH, 3-C), 59.5 (CH, 13-C), 116.25 (q, J 291.7, CF$_3$), 162.8 (q, J 35.2, CF$_3$CO$_2$H), 169.2 (quat., 2-C), 174.0 (quat., 10-CO), and 179.8 (quat., 8-CO); m/z (FAB+) 356.1811 [MH(free base)+. $C_{16}H_{26}N_3O_6$ requires 356.1821].

Example 4

Synthesis of (2S, 3'S, 8'R,)-2-{[(3'-Amino-1'-aza-2'-oxo-bicyclo[6.3.0]undecyl)11'-carbonyl]amino}-1,5-pentandioic acid trifluoroacetate salt Scheme 1 Reagents, conditions and yields:

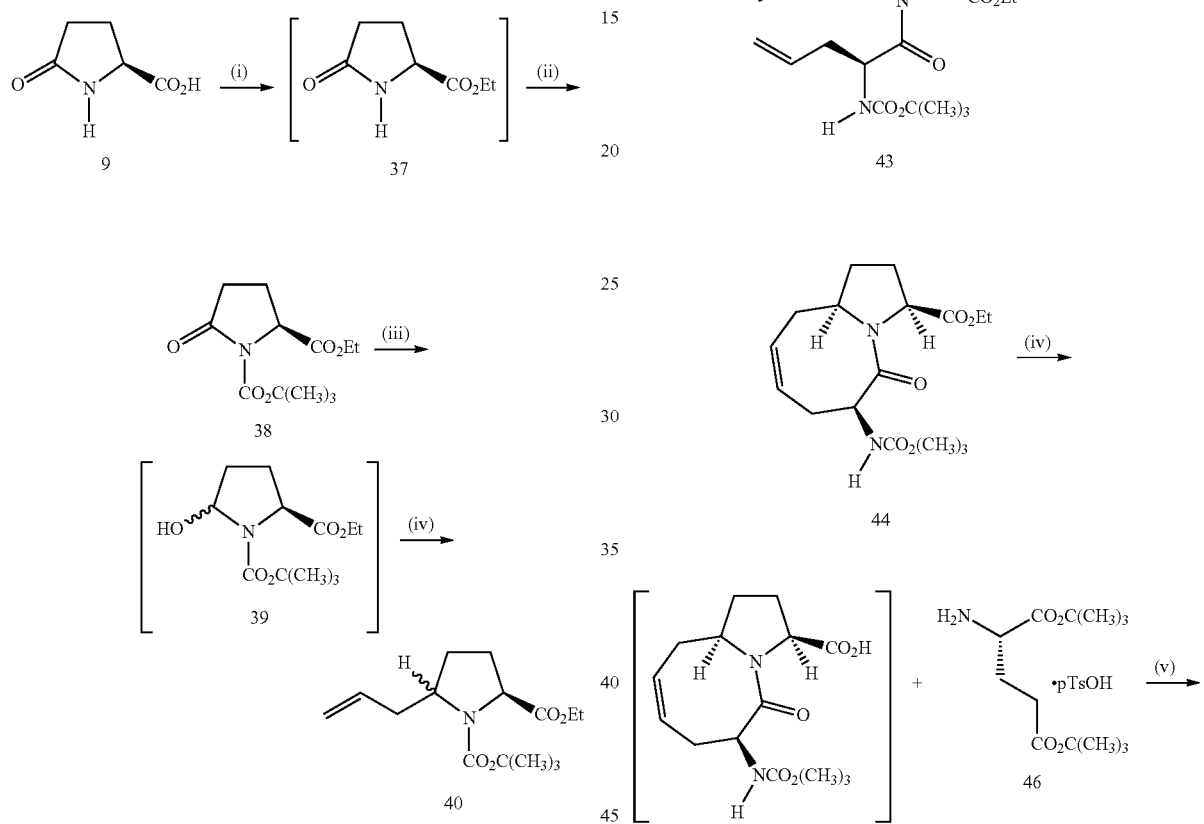

(i) EtOH, SOCl$_2$, 0° C. to RT, overnight;
(ii) DMAP, Boc$_2$O, CH$_3$CN, RT, 18 h (85% over 2 steps);
(iii) LiEt$_3$BH, THF, -78° C., 1 h, then 30% H$_2$O$_2$, 0° C., 0.5 h;
(iv) BF$_3$·OEt$_2$, allyltributylstannane, CH$_2$Cl$_2$, -78° C., 2 h (54%, over 2 steps).

Scheme 2 Reagents, conditions and yields:

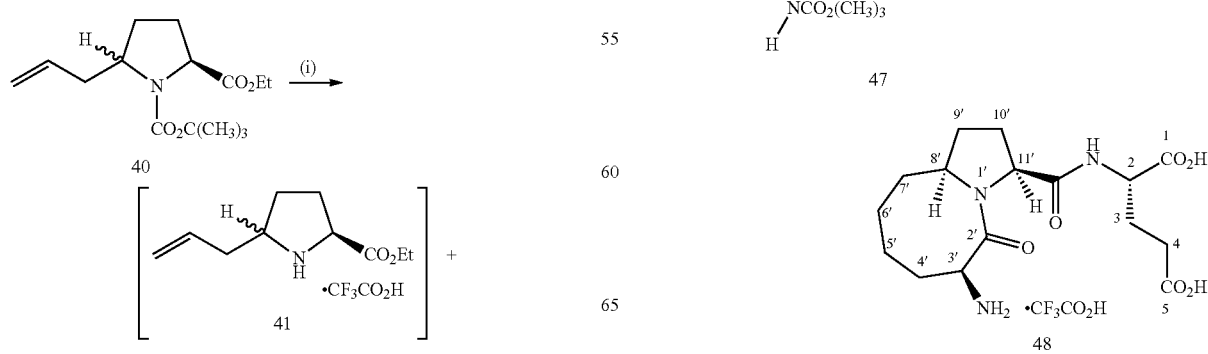

-continued (i) CF₃CO₂H, CH₂Cl₂, RT, 4 h;
(ii) DCC, Et₃N, CH₂Cl₂, 0° C. to RT, overnight (55%, 2 steps);
(iii) Grubbs's catalyst, CH₂Cl₂, 45° C., 24 h then DMSO, RT, overnight (74%);
(iv) 1M aq. NaOH, H₂O, dioxane, RT, 23 h;
(v) BoP-Cl, Et₃N, CH₂Cl₂, 0° C. to RT, 21 h (70%, 2 steps);
(vi) PtO₂, H₂, THF, RT, overnight, then CF₃CO₂H, CH₂Cl₂, RT, 5 h (60%, 2 steps).

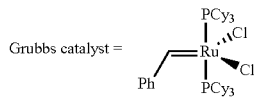

Grubbs catalyst =

(S)-Ethyl N-tert-butoxycarbonylpyroglutamate 38

(S)-Pyroglutamic acid 9 (3.0 g, 15.5 mmol) was suspended in ethanol (40 cm³) and cooled to 0° C. under a nitrogen atmosphere. Thionyl chloride (2.03 g, 17.0 mmol) was added dropwise and the solution was allowed to warm to room temperature overnight. The solution was cooled to 0° C., neutralised with saturated aqueous sodium hydrogen carbonate and extracted with chloroform. The combined organic layers were pooled, dried (Na₂SO₄), filtered and the solvent removed to give the crude ester 37 (2.53 g, 104%) which was used without further purification. To a solution of ester 37 (2.53 g) and dimethylaminopyridine (0.19 g, 1.55 mmol) in acetonitrile (30 cm³) was added di-tent-butyl dicarbonate (3.71 g, 17.05 mmol). The resultant solution was stirred at room temperature for 18 h, concentrated in vacuo and purified by chromatography (SiO₂, 3:1, 2:1, hexanes-ethyl acetate) to give a yellow solid that was recrystallised from hexanes to afford carbamate 38 (3.35 g, 85%, in 2 steps) as a white solid: mp 53-54° C. (lit. 53-54° C.); [α]_D −39.8 (c 0.5 in MeOH) [lit. −46.3 (c 1.5 in MeOH)]; δ_H (300 MHz; CDCl₃; Me₄Si) 1.26 (3H, t, J 7.1, OCH₂CH₃), 1.48 [9H, s, C(CH₃)₃], 1.96-2.06 (1H, m), 2.24-2.68 (3H, m), 4.22 (2H, q, J 7.2, OCH₂CH₃), and 4.58 (1H, dd, J 9.4 and 3.0, 5-H); δ_C (75 MHz; CDCl₃) 14.2 (CH₃, OCH₂CH₃), 21.5 (CH₂, 4-C), 27.9 [CH₃, C(CH₃)₃], 31.2 (CH₂, 3-C), 58.9 (CH, 5-C), 61.7 (CH₂, OCH₂CH₃), 83.5 [quat., C(CH₃)₃], 149.3 (quat., NCO₂), 171.3 (quat., 5-CO) and 173.2 (quat., 2-C).

N-tert-Butoxycarbonyl-(S)-allylglycine-5-allyl-L-proline ethyl ester 43

To a stirred solution of carbamate 38 (1.0 g, 3.89 mmol) in dry tetrahydrofuran (40 cm³) was added a 1 mol L⁻¹ tetrahydrofuran solution of lithium triethylborohydride (4.66 cm³, 4.66 mmol) at −78° C. under at atmosphere of nitrogen. The solution was stirred for 1 h, saturated aqueous sodium hydrogen carbonate (10 cm³) was added and the cooling bath removed. The temperature was allowed to reach 0° C. then 30% aqueous hydrogen peroxide (35 drops) was added and stirring was continued at 0° C. for 50 min. The aqueous layer was extracted with ether, the combined organic extracts were washed with brine, dried (MgSO₄), filtered and the solvent removed to give alcohol 39 (1.301 g). Crude alcohol 39 (0.363 g, ca. 1.40 mmol) was dissolved in dry dichloromethane (10 cm³), allyltributylstannane (0.87 cm³, 2.80 mmol) was added and the solution cooled to −78° C. under a nitrogen atmosphere. Boron trifluoride etherate (0.36 cm³, 2.80 mmol) was added dropwise, and the solution was stirred at −78° C. for 2 h, then saturated aqueous sodium hydrogen carbonate (10 cm³) was added and the reaction mixture warmed to room temperature. The aqueous layer was extracted with dichloromethane and the pooled organic extracts dried (Na₂SO₄) and filtered. Removal of the solvent in vacuo afforeded an oil (1.28 g) which was purified by chromatography (SiO₂, 16:1, 10:1, 8:1, 6:1, 4:1, 3:1, hexanes-ethyl acetate) to afford alkene 40 [0.217 g, 54%, in 2 steps (74% brsm)] as a colourless oil. Alkene 40 was shown to be a 66:33 mixture of C(1)/C(5) cis: trans isomers together with minor component(s). Due to the complex nature of the NMR spectrum this compound was not characterized and used as such for the next step.

Trifluoroacetic acid (2 cm³) was added to a solution of alkene 40 (0.22 g, 0.77 mmol) in dichloromethane (4 cm³) and the solution was stirred at room temperature for 4 h, then the volatiles removed in vacuo to yield the trifluoroacetate salt 41 as an oil. Half of this material (0.383 mmol) was dissolved in dichloromethane (7 cm³), N-tert-butoxycarbonyl-(S)-allylglycine 42 (0.07 g, 0.32 mmol) and triethylamine (0.042 g, 0.42 mmol) were added and the solution cooled to 0° C. N,N'-Dicyclohexylcarbodiimide (0.065 g, 0.316 mmol) was added, the mixture stirred overnight, then filtered through Celite™ to remove dicyclohexyl urea. The filtrate was subsequently washed with saturated aqueous sodium hydrogen carbonate, 2 M aqueous hydrochloric acid, dried (MgSO₄), filtered and the solvent removed to yield an oil (0.113 g) which was purified by chromatography (SiO₂, 4:1, hexane-ethyl acetate) to afford diene 43 (0.064 g, 55%, 2 steps) as a colourless oil. Diene 43 was an inseparable mixture of diastereomers [C2/C5, cis/trans, 77:23]: δ_H (400 MHz; CDCl₃; Me₄Si) 1.21-1.26 (3H, m, OCH₂CH₃), 1.37 [6.93H, s, C(CH₃)₃], 1.41 [2.07H, s, C(CH₃)₃], 1.64-1.97 (4H, m, Proβ-H₂ and Proγ-H₂), 2.0-2.52 [3.77H, m, 2×CH₂(allyl)], 2.75-2.95 [0.23H, m, CH_ACH_B(allyl)], 4.07-4.21 (2.23H, m, OCH₂CH₃ and Proα-H*), 4.32-4.48 (2.77H, Proδ-H, Glyα-H and Proα-H), 4.97-5.26 (5H, m, 2×=CH₂, N—H) and 5.64-5.84 [2H, m, 2×C(H)=CH₂]; δ_C (100 MHz; CDCl₃) 13.9* (CH₃, OCH₂CH₃), 14.1 (CH₃, OCH₂CH₃), 26.8 (CH₂, Proβ-C), 28.3 [CH₃, C(CH₃)₃], 29.0* (CH₂, Proγ-C), 29.5 (CH₂, Proγ-C), 37.7* [CH₂, CH₂(allyl)Pro], 37.8 [CH₂, CH₂(allyl)Gly], 38.4* [CH₂, CH₂(allyl)Gly], 39.4* [CH₂, CH₂(allyl)Pro], 50.9 (CH, Glyα-C), 51.9* (CH, Glyα-C), 58.2 (CH, Proα-C), 58.5* (CH, Proα-C), 59.5 (CH, Proδ-C), 59.8* (CH, Proδ-C), 61.0 (CH₂, OCH₂CH₃), 61.9* (CH₂, OCH₂CH₃), 79.4* [quat., C(CH₃)₃], 79.7 [quat., C(CH₃)₃], 117.2* (CH₂, =CH₂), 118.3 (CH₂, =CH₂), 118.35 (CH₂, =CH₂), 118.7* (CH₂, =CH₂), 132.7* (CH, C(H)=CH₂), 133.2 [CH, C(H)=CH₂], 134.0 [CH, C(H)=CH₂], 134.7* [CH, C(H)=CH₂], 154.7* (quat., NCO₂), 155.3 (quat., NCO₂), 170.5* (quat., CO), 171.4 (quat., CO), 171.6* (quat., CO) and 172.1 (quat., CO); m/z (FAB+) 381.23896 (MH⁺. C₂₀H₃₃N₂O₅ requires 381.23895).

(8R, 3S, 11S) 1-Aza-3-(tert-butyloxycarbonylamino)-1-ethoxycarbonyl-2-oxobicyclo[6.3.0]undec-5-ene 44

To a degassed solution of diene 43 (0.064 g, 0.170 mmol) in dry dichloromethane (43 cm³) was added bis(tricyclohexylphosphine)benzylidineruthenium dichloride (Grubbs catalyst) (0.014 g, 0.0170 mmol) under a nitrogen atmosphere and the resultant purple solution heated at reflux for 24 h. The orange/brown solution was cooled to room temperature, dimethyl sulphoxide (0.160 cm³, 2.26 mmol) was added and the solution stirred overnight. The solvent was removed in vacuo and the residue purified by chromatography (SiO₂, 2:1, 1:1, hexanes-ethyl acetate,) to give alkene 44 (0.044 g, 74%) as a colourless oil. Alkene 44 existed exclusively as the trans C(O)—NPro conformer: [α]_D −93.2 (c 0.29 in CH₂Cl₂); δ_H (400 MHz; CDCl₃; Me₄Si) 1.25 (3H, t, J 7.1, OCH₂CH₃), 1.42 [9H, s, C(CH₃)₃], 1.89-1.98 (2H, m, 10-H_AH_B and 9-H_AH_B), 2.01-2.09 (1H, m, 9-H_AH_B), 2.11-2.16 (1H, m, 10-H_AH_B), 2.24-2.33 (1H, m, 4-H_AH_B), 2.42 (1H, dq, J 15.2 and 3.4, 7-H_AH_B), 2.70-2.80 (2H, m, 4-H_AH_B and 7-H_AH_B), 4.15 (3H, q, J 7.1, OCH_2CH_3 and 8-H obscured), 4.47 (1H, dd, J 8.4 and 2.8, 11-H), 4.84 (3H, br q, J 7.8, 3-H), 5.59 (1H, d, J 7.3, N—H), 5.67-5.73 (1H, m, 6-H) and 5.77-5.83 (1H, m, 5-H); et (100 MHz; CDCl_3) 14.0 (CH_3, OCH_2CH_3), 27.1 (CH_2, 10-C), 28.2 [CH_3, C(CH_3)_3], 32.77 (CH_2, 7-C or 9-C), 32.84 (CH_2, 9-C or 7-C), 35.2 (CH_2, 4-C), 51.7 (CH, 3-C), 58.6 (CH, 8-C), 60.2 (CH, 11-C), 60.8 (CH_2, OCH_2CH_3), 79.4 [quat., C(CH_3)_3], 125.7 (CH, 6-C), 129.1 (CH, 5-C), 155.1 (quat., NCO_2), 170.9 (quat., 11-CO) and 171.7 (quat., 2-C); m/z (EI+) 352.2001 (M+. $C_{18}H_{28}N_2O_5$ requires 352.1998).

(2S, 3'S, 8'R, 11'S)-Di-tert-butyl 2-{[1'-aza-3'-(tert-butyloxycarbonylamino)-2'-oxobicyclo[6.3.0]-undec-5'-ene]-11-carbonyl]amino}-1,5-pentandioate 47

1M Aqueous sodium hydroxide (0.63 cm³, 0.63 mmol) was added to a solution of ester 44 in dioxane (1.3 cm³) and the opaque solution stirred for 23 h at room temperature. The reaction mixture was diluted with water, extracted with dichloromethane and the aqueous layer acidified with solid citric acid and extracted with dichloromethane. The combined organic layers were dried (Na_2SO_4), filtered and the solvent removed to yield acid 45 (0.040 g). Hydrochloride 46 (0.048 g, 0.1625 mmol) was added to a solution of 45 and the solution then cooled to 0° C. Triethylamine (0.033 cm³, 0.325 mmol) and bis(2-oxo-3-oxazolidinyl)phosphinic chloride (BoP-Cl) (0.041 g, 0.163 mmol) were added and the mixture stirred for 21 h. The reaction mixture was washed with saturated aqueous sodium hydrogen carbonate, 2 M aqueous hydrochloric acid, dried (Na_2SO_4), filtered and the solvent removed to yield an oil (0.078 g) which was purified by chromatography (SiO_2, 1:1,hexane-ethyl acetate) to afford amide 47 (0.050 g, 70%, in 2 steps) as a colourless oil. Amide 47 existed exclusively as the trans C(O)—NPro conformer:: $[\alpha]_D$ –79.4 (c 0.47 in CH_2Cl_2); δ_H (400 MHz; CDCl_3; Me_4Si) 1.39-1.50 [27H, m, 3×C(CH_3)_3], 1.78-1.91 (3H, m, 10'-H_AH_B, 3-H_AH_B and 9'-H_AH_B), 2.0-2.33 (7H, m, 10'-H_AH_B, 3-H_AH_B, 4-H_2, 9'-H_AH_B, 7'-H_AH_B and 4'-H_AH_B), 2.80-2.95 (2H, br m, 7'-H_AH_B and 4'-H_AH_B), 4.15 (1H, br q, J 7.1, 8'-H), 4.42 (1H, ddd, J 7.8, 7.8 and 5.2, 2-H), 4.66 (1H, d, J 7.5, 11'-H), 4.97 (1H, br q, J 7.4, 3'-H), 5.57 (1H, d, J 7.8, N—H), 5.61-5.67 (1H, m, 6'-H), 5.81 (1H, br t, J 7.8, 5'-H) and 7.47 (1H, d, J 8.0, N—H); δ_C (100 MHz; CDCl_3) 26.1 (CH_2, 10'-C), 27.9 [CH_3, C(CH_3)_3], 27.95 [CH_3, C(CH_3)_3], 28.2 [CH_3, C(CH_3)_3], 28.1, (CH_2, 3-C), 31.3 (CH_2, 4-C), 32.0 (CH_2, 7'-C), 33.2 (CH_2, 9'-C), 35.7 (CH_2, 4'-C), 51.0 (CH, 3'-C), 51.9 (CH, 2-C), 58.6 (CH, 8'-C), 60.8 (CH, 11'-C), 79.6 [quat., C(CH_3)_3], 80.4 [quat., C(CH_3)_3], 81.9 [quat., C(CH_3)_3], 124.9 (CH, 6'-C), 130.4 (CH, 5'-C), 155.0 (quat., NCO_2), 169.9 (quat., 1-C), 170.5 (quat., 11'-CO), 171.8 (quat., 2'-C or 5-C) and 171.9 (quat., 2'-C or 5-C); m/z (FAB+) 566.3454 [MH+. $C_{29}H_{48}N_3O_8$ requires 566.3441].

(2S, 3'S, 8'R, 11'S) 2-{[(3'-Amino-1'-aza-2'-oxobicyclo[6.3.0]-undecyl)-11'-carbonyl]amino}-1,5-pentanedioic acid trifluoroacetate salt 48

PtO_2 (0.00184 g, 0.0081 mmol) was added to a stirred solution of amide 47 (0.046 g, 0.081 mmol) in tetrahydrofuran (4 cm³) under a nitrogen atmosphere. The mixture was hydrogenated (1 atm. of hydrogen) overnight, filtered through Celite™, and the solvent removed in vacuo. The residue was dissolved in dichloromethane (5 cm³), trifluoroacetic acid (3 cm³) added and the solution stirred for 5 h at room temperature. Removal of the volatiles in vacuo, purification by RP HPLC [10% acetonitrile:90% water (containing 0.05% trifluoroacetic acid)] and trituration from ether/toluene gave 13 (0.0228 g, 60%, 2 steps) as a hygroscopic off-white solid. 48 existed exclusively as the trans C(O)—NPro conformer: mp 50-120° C.; $[\alpha]_D$ –27.9 (c 0.33 in MeOH); δ_H (400 MHz; D_2O) 1.37-1.85 (8H, m, 5'-H_2, 6'-H_2, 4'-H_2 and 9'-H_2), 1.98-2.28 (5H, m, 3-H_2, 7'-H_2 and 10'-H_AH_B), 2.36 (1H, dt, J 12.4 and 7.2, 10'-H_AH_B), 2.57 (2H, t, J 7.6, 4-H_2), 4.23 (1H, br t, J 8.2, 8'-H) and 4.41 (3H, m, 2-H, 11'-H, 3'-H); δ_C (100 MHz; D_2O) 21.6 (CH_2, 5'-C or 6'-C), 24.2 (CH_2, 5'-C or 6'-C), 25.5 (CH_2, 3-C), 27.1 (CH_2, 10'-C), 29.7 (CH_2, 4-C), 31.5 (CH_2, 9'-C), 32.8 (CH_2, 7'-C), 35.0 (CH_2, 4'-C), 51.2 (CH, 3'-C), 51.9 (CH, 2-C), 59.9 (CH, 8'-C), 61.4 (CH, 11'-C), 116.2 (quat., q, J 291, CF_3), 162.7 (quat., q, J 35.2, CF_3CO_2H), 168.5 (quat., 2'-C), 173.7 (quat., 11'-CO) and 176.8 (quat., 5-C); m/z (FAB+) 356.1816 [MH(free base)+. $C_{16}H_{26}N_3O_6$ requires 356.1822].

Example 5

Synthesis of (9R, 11S, 14S)-1,4,12-triaza-9,11-carboxy-2,13-dioxobicyclo[14.3.0]heptadecane trifluoroacetate Scheme 1 Reagents, conditions and yields:

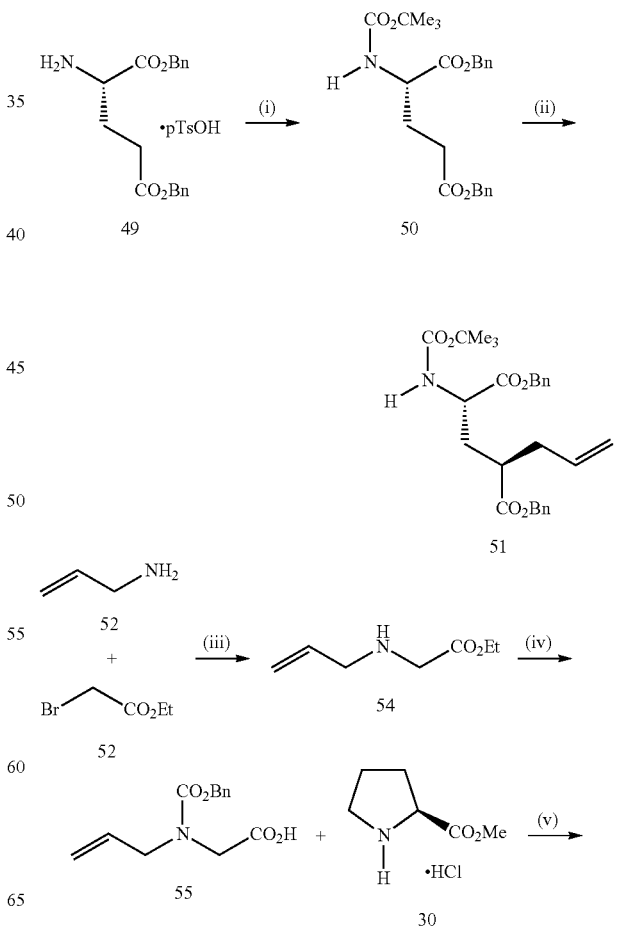

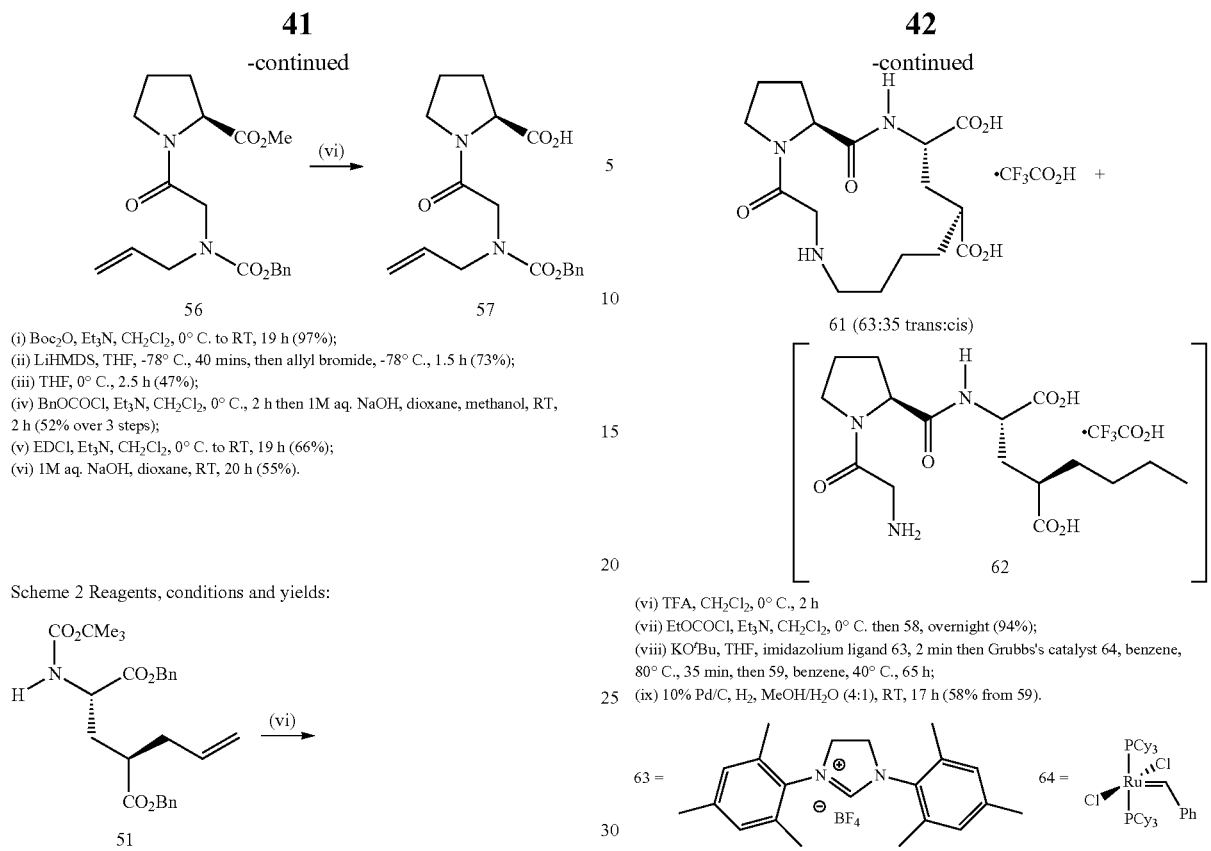

(i) Boc₂O, Et₃N, CH₂Cl₂, 0° C. to RT, 19 h (97%);
(ii) LiHMDS, THF, -78° C., 40 mins, then allyl bromide, -78° C., 1.5 h (73%);
(iii) THF, 0° C., 2.5 h (47%);
(iv) BnOCOCl, Et₃N, CH₂Cl₂, 0° C., 2 h then 1M aq. NaOH, dioxane, methanol, RT, 2 h (52% over 3 steps);
(v) EDCl, Et₃N, CH₂Cl₂, 0° C. to RT, 19 h (66%);
(vi) 1M aq. NaOH, dioxane, RT, 20 h (55%).

Scheme 2 Reagents, conditions and yields:

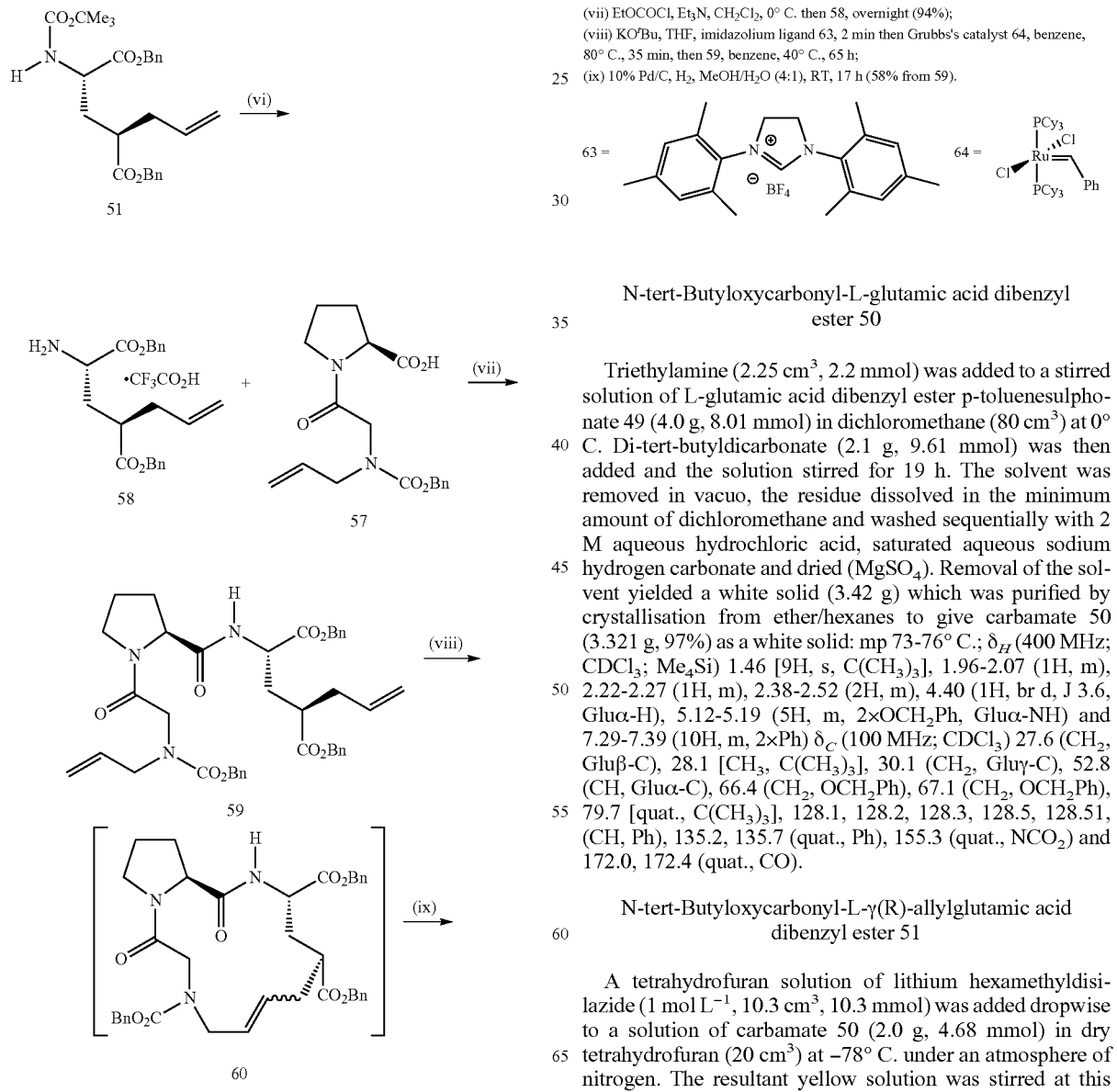

(vi) TFA, CH₂Cl₂, 0° C., 2 h
(vii) EtOCOCl, Et₃N, CH₂Cl₂, 0° C. then 58, overnight (94%);
(viii) KOᵗBu, THF, imidazolium ligand 63, 2 min then Grubbs's catalyst 64, benzene, 80° C., 35 min, then 59, benzene, 40° C., 65 h;
(ix) 10% Pd/C, H₂, MeOH/H₂O (4:1), RT, 17 h (58% from 59).

N-tert-Butyloxycarbonyl-L-glutamic acid dibenzyl ester 50

Triethylamine (2.25 cm$^3$, 2.2 mmol) was added to a stirred solution of L-glutamic acid dibenzyl ester p-toluenesulphonate 49 (4.0 g, 8.01 mmol) in dichloromethane (80 cm$^3$) at 0° C. Di-tert-butyldicarbonate (2.1 g, 9.61 mmol) was then added and the solution stirred for 19 h. The solvent was removed in vacuo, the residue dissolved in the minimum amount of dichloromethane and washed sequentially with 2 M aqueous hydrochloric acid, saturated aqueous sodium hydrogen carbonate and dried (MgSO$_4$). Removal of the solvent yielded a white solid (3.42 g) which was purified by crystallisation from ether/hexanes to give carbamate 50 (3.321 g, 97%) as a white solid: mp 73-76° C.; $\delta_H$ (400 MHz; CDCl$_3$; Me$_4$Si) 1.46 [9H, s, C(CH$_3$)$_3$], 1.96-2.07 (1H, m), 2.22-2.27 (1H, m), 2.38-2.52 (2H, m), 4.40 (1H, br d, J 3.6, Gluα-H), 5.12-5.19 (5H, m, 2×OCH$_2$Ph, Gluα-NH) and 7.29-7.39 (10H, m, 2×Ph) $\delta_C$ (100 MHz; CDCl$_3$) 27.6 (CH$_2$, Gluβ-C), 28.1 [CH$_3$, C(CH$_3$)$_3$], 30.1 (CH$_2$, Gluγ-C), 52.8 (CH, Gluα-C), 66.4 (CH$_2$, OCH$_2$Ph), 67.1 (CH$_2$, OCH$_2$Ph), 79.7 [quat., C(CH$_3$)$_3$], 128.1, 128.2, 128.3, 128.5, 128.51, (CH, Ph), 135.2, 135.7 (quat., Ph), 155.3 (quat., NCO$_2$) and 172.0, 172.4 (quat., CO).

N-tert-Butyloxycarbonyl-L-γ(R)-allylglutamic acid dibenzyl ester 51

A tetrahydrofuran solution of lithium hexamethyldisilazide (1 mol L$^{-1}$, 10.3 cm$^3$, 10.3 mmol) was added dropwise to a solution of carbamate 50 (2.0 g, 4.68 mmol) in dry tetrahydrofuran (20 cm$^3$) at −78° C. under an atmosphere of nitrogen. The resultant yellow solution was stirred at this temperature for 40 min and allyl bromide (1.31 cm$^3$, 14.0 mmol) was added. The solution was stirred for 1.5 h at −78° C. and quenched by the addition of saturated aqueous ammonium chloride (20 cm$^3$). The cooling bath was removed and the mixture allowed to warm to room temperature over 1.5 h. A white solid was removed by filtration, washed with ethyl acetate and the filtrate concentrated in vacuo to yield an orange oil (2.312 g) which was purified by chromatography (silica gel, 6:1, hexane:ethyl acetate, then 5:1) to give alkene 51 (1.589 g, 73%) as a colourless oil: [α]$_D$ +19.4 (c 0.232 in CH$_2$Cl$_2$); δ$_H$ (300 MHz; CDCl$_3$; Me$_4$Si) 1.43 [9H, s, C(CH$_3$)$_3$], 2.06 (2H, m, allyl-CH$_2$), 2.30-2.44 (2H, m, Gluβ-H$_2$), 2.64 (1H, p, J 6.7, Gluγ-H), 4.41 (1H, br d, J 7.6, Gluα-H), 5.01-5.71 (7H, m, 2×OCH$_2$Ph, =CH$_2$, Gluα-NH), 5.60-5.74 (1H, m, C(H)=CH$_2$) and 7.31-7.35 (10H, m, 2×Ph); δ$_C$ (75 MHz; CDCl$_3$) 28.2 [CH$_3$, C(CH$_3$)$_3$], 33.4 (CH$_2$, allyl-CH$_2$), 36.2 (CH$_2$, Gluβ-C), 41.7, (CH, Gluγ-C), 52.2 (CH, Gluα-C), 66.4 (CH$_2$, OCH$_2$Ph), 67.0 (CH$_2$, OCH$_2$Ph), 80.0 [quat., C(CH$_3$)$_3$], 117.6 (CH$_2$, =CH$_2$), 128.16, 128.18, 128.3, 128.44, 128.47, (CH, Ph), 134.1 (CH, C(H)=CH$_2$), 135.2, 135.7 (quat., Ph), 155.3 (quat., NCO$_2$), 172.1 (quat., Gluα-CO) and 174.6 (quat., Gluγ-CO); m/z (FAB+) 468.2382 (MH$^+$. C$_{27}$H$_{34}$NO$_6$ requires 468.2386).

N-Allylglycine ethyl ester 54

A solution of ethyl bromoacetate 52 (3 g, 18.0 mmol) in dry tetrahydrofuran (20 cm$^3$) was added dropwise to an ice-cold solution of allylamine 53 (2.05 g, 36 mmol) in dry tetrahydrofuran (20 cm$^3$) over 3 min. The solution was stirred at 0° C. for 2.5 h (a white precipitate was observed after 2 h), concentrated in vacuo and suspended in diethyl ether. The white suspension was filtered through Celite™ and the solvent removed to yield the crude product which was purified by chromatography (silica gel, 1:1, hexane:ethyl acetate) to give alkene 54 (1.209 g, 47%) as a light yellow oil: δ$_H$ (300 MHz; CDCl$_3$; Me$_4$Si) 1.17 (3H, t, J 7.1, OCH$_2$CH$_3$), 1.70 (1H, br s, N—H), 3.16 [211, d, J 5.9, CH$_2$(allyl)], 3.28 (2H, s, CH$_2$Gly), 4.08 (2H, q, J 7.1, OCH$_2$CH$_3$), 4.98-5.12 (2H, m, =CH$_2$) and 5.70-5.85 (1H, m, C(H)=CH$_2$); δ$_C$ (75 MHz; CDCl$_3$) 13.9 (CH$_3$, OCH$_2$CH$_3$), 49.7 (CH$_2$), 51.6 (CH$_2$), 60.4 (CH$_2$, OCH$_2$CH$_3$), 116.2 (CH$_2$, =CH$_2$), 135.9 (CH, C(H)=CH$_2$) and 172.2 (quat., CO).

N-Allyl-N-benzyloxycarbonylglycine 55

N-Allylglycine ethyl ester 54 was prepared as described above using ethyl bromoacetate (9 g, 53.9 mmol) and allylamine (6.15 g, 107.7 mmol). The crude product (7.054 g) that contained ~30% of N-allyl-N-bis(2-carboethyoxyethyl)amine as judged by NMR, was dissolved in dichloromethane (50 cm$^3$), cooled to 0° C. and triethylamine (6.53 g, 64.09 mmol) added. Benzylchloroformate (9.25 g, 54.2 mmol) was added dropwise over 10 min resulting in a white precipitate. After 2 h the mixture was stored overnight at 0° C., filtered and the filtrate concentrated in vacuo. The residue was subsequently suspended in dichloromethane, washed with 2M aqueous hydrochloric acid, dried (MgSO$_4$) and the solvent removed to reveal an oil (13.65 g) containing the desired carbamate (70%) and benzyl alcohol (30%) as judged by NMR. This mixture was dissolved in dioxane/methanol (8:3, 110 cm$^3$), 1M aqueous sodium hydroxide (40 cm$^3$, 40 mmol) added and the solution stirred for 2 h at room temperature. Brine (50 cm$^3$) was added and the aqueous layer extracted with diethyl ether. The aqueous layer was acidified with 32% hydrochloric acid and extracted with ethyl acetate. The combined organic layers were dried (MgSO$_4$), concentrated in vacuo, and the residue purified by chromatography (silica gel, hexane:ethyl aceate:acetic acid, 3:1:0.4) to give acid 7 (7.05 g, 52%, 3 steps) as a colourless syrup. Acid 55 existed as a 1:1 mixture of carbamate rotamers: δ$_H$ (400 MHz; CDCl$_3$; Me$_4$Si) 4.02-4.08 [4H, m, CH$_2$(allyl), C$_2$(Gly)], 5.17-5.24 (4H, m, OCH$_2$Ph, =CH$_2$), 5.77-5.84 (1H, m, C(H)=CH$_2$), 7.32-7.39 (m, 5H, Ph) and 8.45 (1H, br s, OH); δ$_C$ (100 MHz; CDCl$_3$) 47.1, 47.7 [CH$_2$, CH$_2$(Gly)], 50.5, 50.7 [CH$_2$, CH$_2$ (allyl)], 67.6, 67.7 (CH$_2$, OCH$_2$Ph), 117.8, 118.3 (CH$_2$, =CH$_2$), 127.7, 127.97, 128.01, 128.4, (CH, Ph), 132.7, 132.8 (CH, C(H)=CH$_2$) 136.1 (quat., Ph), 155.8, 156.5, (quat., NCO$_2$) and 174.7, 174.9 (quat., CO).

N-Allyl-N-benzyloxycarbonylglycyl-L-proline methyl ester 56

1-(3-Dimethylaminopropyl-3-ethylcarbodiimide hydrochloride (EDCI) (0.453 g, 2.36 mmol) was added to a solution of proline methyl ester hydrochloride 30 (0.356 g, 2.15 mmol), acid 55 (0.590 mmol, 2.35 mmol) and triethylamine (0.481 g, 4.73 mmol) in dichloromethane (20 cm$^3$) at 0° C. The resultant solution was stirred for 19 h, washed with 2M aqueous hydrochloric acid and saturated aqueous sodium hydrogen carbonate, dried (MgSO$_4$) and the solvent removed to yield an oil which was purified by chromatography (silica gel, hexanes:ethyl acetate, 2:1, 1:1) to afford protected dipeptide 56 (0.508 g, 66%) as a colourless oil. Dipeptide 56 was shown to be a 76:24 trans:cis mixture of conformers by $^{13}$C NMR analysis (the ratio was estimated by integration of signals at δ22.0 and 24.5, 24.7, assigned to the Proγ-C atoms of the minor and major conformers respectively). In addition, restricted rotation about the GlyN-CO carbamate bond was also observed resulting in a further 1:1 mixture of conformers: [α]$_D$ −54.6 (c 1.17 in CH$_2$Cl$_2$); δ$_H$ (400 MHz; CDCl$_3$; Me$_4$Si) 1.81-2.14 (4H, m, Proβ H$_2$, Proγ-H$_2$), 3.29-3.58 (2H, m, Proδ-H$_2$), 3.64, 3.66, 3.69* (3H, s, OCH$_3$), 3.84-4.20 [4H, m, CH$_2$(allyl), Glyα-H$_2$], 4.40-4.48 (1H, m, Proα-H), 5.07-5.17 (4H, m, OCH$_2$Ph, =CH$_2$), 5.69-5.81 (1H, m, C(H)=CH$_2$) and 7.24-7.30 (m, 5H, Ph); δ$_C$ (100 MHz; CDCl$_3$) 22.0* (CH$_2$, Proγ-C), 24.62, 24.73 (CH$_2$, Proγ-C), 28.66, 28.73 (CH$_2$, Proβ-C), 31.1,* 31.3* (CH$_2$, Proβ-C), 45.93, 45.98 (CH$_2$, Proδ C), 46.5* (CH$_2$, Proδ-C), 47.5, 48.0 (CH$_2$, Glyα-C), 50.0, 50.6 [CH$_2$, CH$_2$(allyl)], 50.0,* 50.6* [CH$_2$, CH$_2$ (allyl)], 52.0, (CH$_3$, OCH$_3$), 52.31,* 52.5* (CH$_3$, OCH$_3$), 58.4,* 58.5* (CH, Proα-C), 58.8 (CH, Proα-C), 67.2, 67.3 (CH$_2$, OCH$_2$Ph), 117.0, 117.5 (CH$_2$, =CH$_2$), 127.5, 127.7, 127.8, 128.3, (CH, Ph), 133.2, 133.4 (CH, C(H)=CH$_2$) 136.4, 136.5 (quat., Ph), 155.8, 156.3, (quat., NCO$_2$), 167.1 (quat., Gly-CO), 167.4,* 167.5* (quat., Gly-CO). 172.0,* 172.2* (quat., Pro-CO) and 172.3, 172.4 (quat., Pro-CO); m/z (EI+) 360.1676 (M$^+$. C$_{19}$H$_{24}$N$_2$O$_5$ requires 360.1685).

N-Allyl-N-benzyloxycarbonylglycyl-L-proline 57

To a solution of protected dipeptide 56 (0.474 g, 1.31 mmol) in dioxane (13 cm$^3$) was added 1M aqueous sodium hydroxide (6.71 cm$^3$, 6.71 mmol) and the mixture stirred at room temperature for 20 h. Water (10 cm$^3$) was added and the mixture extracted with dichloromethane. The aqueous layer was acidified with 10% HCl and the product extracted with dichloromethane. The organic layers were pooled, dried (MgSO$_4$) and the solvent removed to afford an oil (0.456 g) contaminated with 2-hydroxy-1,4-dioxane. Subsequent purification by chromatography (silica gel, hexanes:ethyl acetate, 1:1, 1:2, 1:3,) gave acid 57 (0.250 g, 55%) as a colourless oil: Acid 57 was shown to be a 86:14 trans:cis mixture of conformers by $^{13}$C NMR analysis (the ratio was estimated by integration of signals at δ22.1 and 24.6, 24.7, assigned to the Proγ-C atoms of the minor and major conformers respectively). In addition, restricted rotation about the GlyN-CO carbamate bond was also observed resulting in a further 1:1 mixture of conformers [α]$_D$–117 (c 0.8 in CH$_2$Cl$_2$); δ$_H$ (300 MHz; CDCl$_3$; Me$_4$Si) 1.88-2.25 (4H, m, Proγ(3-H$_2$), Proγ-H$_2$), 3.30-3.69 (2H, m, Proδ-H$_2$), 3.75-4.26 [4H, m, CH$_2$ (allyl), Glyα-H$_2$], 4.50-4.58 (1H, m, Proα-H), 5.10-5.22 (4H, m, OCH$_2$Ph, =CH$_2$), 5.73-5.82 (1H, m, C(H)=CH$_2$), 7.33-7.34 (m, 5H, Ph) and 7.84 (1H, br s, OH); δ$_C$ (75 MHz; CDCl$_3$) 22.1* (CH$_2$, Proγ-C), 24.6, 24.7 (CH$_2$, Proγ-C), 27.9, 28.0 (CH$_2$, Proγ(3-C), 31.1,* 31.3* (CH$_2$, Proγ(3-C), 46.5 (CH$_2$, ProδC), 46.7* (CH$_2$, Proδ-C), 47.5, 48.1 (CH$_2$, Glyα-C), 47.7,* 48.2* (CH$_2$, Glyα-C), 50.2, 50.7 [CH$_2$, CH$_2$(allyl)], 50.5,* 50.9* [CH$_2$, CH$_2$(allyl)], 58.6* (CH, Proα-C), 59.5 (CH, Proα-C), 67.6 (CH$_2$, OCH$_2$Ph), 117.3, 117.9 (CH$_2$, =CH$_2$), 127.6, 127.9, 128.0, 128.4, (CH, Ph), 133.0, 133.2 (CH, C(H)=CH$_2$) 136.3 (quat., Ph), 155.9, 156.5, (quat., NCO$_2$), 156.7* (quat., NCO$_2$), 167.8* (quat., Gly-CO), 168.9, 169.0 (quat., Gly-CO), 173.6, 173.7 (quat., Pro-CO) and 174.4* (quat., Pro-CO); m/z (EI+) 346.1524 (M$^+$. C$_{18}$H$_{22}$N$_2$O$_5$ requires 346.1529).

N-Allyl-N-benzyloxycarbonylglycyl-L-prolyl-L-γ (R)-allylglutamic acid dibenzyl ester 59

Alkene 51 (0.359 g, 0.768 mmol) was dissolved in dichloromethane (10 cm$^3$), cooled to 0° C. and trifluoroacetic acid (2 cm$^3$) was added. After stirring for 2 h the volatiles were removed in vacuo to yield trifluoroacetate 58 as a white solid. To an ice cold solution of acid 57 (0.288 g, 0.655 mmol) and triethylamine (0.150 cm$^3$, 0.80 mmol) was added dropwise ethyl chloroformate (0.075 cm$^3$, 0.786 mmol). The solution was stirred at 0° C. for 40 min then an ice-cold solution of 58 and triethylamine (0.150 cm$^3$, 0.80 mmol) in dichloromethane (15 cm$^3$) was added dropwise and the mixture stirred overnight. The solution was subsequently washed with 2M aqueous hydrochloric acid, saturated aqueous sodium hydrogen carbonate, dried (MgSO$_4$) and the solvent removed to yield an oil which was purified by chromatography (silica gel, hexane:ethyl acetate, 1:1) to give fully protected tripeptide 59 (0.432 g, 94%) as a colourless oil. Tripeptide 59 was shown to be a 85:15 trans:cis mixture of conformers by $^{13}$C NMR analysis (the ratio was estimated by integration of signals at δ22.1 and 24.9 assigned to the Proγ-C atoms of the minor and major conformers respectively). In addition, restricted rotation about the GlyN-CO carbamate bond was also observed resulting in a further 1:1 mixture of conformers: [α]$_D$ –38.7 (c 0.73 in CH$_2$Cl$_2$); δ$_H$ (300 MHz; CDCl$_3$; Me$_4$Si) 1.75-2.33 [8H, m, Proβ-H$_2$, Proγ-H$_2$, Gluβ-H$_2$, CH$_2$ (allyl)], 2.55-2.66 (1H, m, Gluγ-H), 3.25-3.63 (m, 2H, Proδ-H$_2$), 3.77-4.19 [4H, m, Glyα-H$_2$, CH$_2$(allyl)], 4.32* (0.15H, d, J 7.7, Proα-H), 4.46-4.60 (1.85H, m, Proα-H, Gluα-H), 4.99-5.15 (10H, m, 3×OCH$_2$Ph, 2×=CH$_2$), 5.57-5.82 (2H, m, 2×C(H)=CH$_2$) and 7.19-7.34 (16H, m, 3×Ph, GluN—H); δ$_C$ (75 MHz; CDCl$_3$) 22.2* (CH$_2$, Proγ-C), 24.9 (CH$_2$, Proγ-C), 27.2* (CH$_2$, Proβ-C), 27.5 (CH$_2$, Proγ(3-C), 31.8° [CH$_2$, CH$_2$(allyl)], 32.7 [CH$_2$, CH$_2$(allyl)], 35.9 (CH$_2$, Gluβ-C), 36.0* (CH$_2$, Gluβ-C), 41.2 (CH, Gluγ-C), 41.9* (CH, Gluγ-C), 46.4 (CH$_2$, Proδ-C), 46.9* (CH$_2$, Proδ-C), 47.6,* (CH$_2$, Glyα-C), 48.3 (CH$_2$, Glyα-C), 48.2,* (CH$_2$, Glyα-C), 50.4 [CH$_2$, CH$_2$(allyl)], 50.7, 50.9 (CH$_2$, Gluα-C), 51.2* [CH$_2$, CH$_2$(allyl)], 51.4* (CH$_2$, Gluα-C), 59.96* (CH, Proα-C), 60.0 (CH, Proα-C), 60.4* (CH, Proα-C), 66.3 (CH$_2$, OCH$_2$Ph), 66.4* (CH$_2$, OCH$_2$Ph), 66.5* (CH$_2$, OCH$_2$Ph), 67.0 (CH$_2$, OCH$_2$Ph), 67.1* (CH$_2$, OCH$_2$Ph), 67.35 (CH$_2$, OCH$_2$Ph), 67.4 (CH$_2$, OCH$_2$Ph), 117.0 (CH$_2$, =CH$_2$), 117.1* (CH$_2$, =CH$_2$), 117.5 (CH$_2$, =CH$_2$), 117.6 (CH$_2$, =CH$_2$), 117.8* (CH$_2$, =CH$_2$) 118.0* (CH$_2$, =CH$_2$), 127.56,* 127.63,* 127.77,* 127.85,* 128.08, 128.13, 128.17, 128.35, 128.39, 128.43 (CH, Ph), 133.3 (CH, C(H)=CH$_2$), 133.5* (CH, C(H)=CH$_2$), 134.0* (CH, C(H)=CH$_2$), 134.2* (CH, C(H)=CH$_2$), 134.3 (CH, C(H)=CH$_2$), 135.2* (quat., Ph), 135.3 (quat., Ph), 135.7 (quat., Ph), 136.4 (quat., Ph), 136.6* (quat., Ph), 155.9* (quat., NCO$_2$), 156.5, (quat., NCO$_2$), 168.4 (quat., Gly-CO), 170.9,* 171.0, 171.4, 171.8* (quat., Pro-CON, Gluα-CO), 174.3* (quat., Gluγ-CO) and 174.4 (quat., Gluγ-CO); m/z (FAB+) 696.3280 (MH$^+$. C$_{40}$H$_{46}$N$_3$O$_8$ requires 696.3285).

(9R, 11S, 14S)-1,4,12-Triaza-9,11-carboxy-2,13-dioxobicyclo[14.3.0]-heptadecane trifluoroacetate 61

Freshly sublimed potassium tert-butoxide (0.009 g, 0.0792 mmol) was added to a stirred suspension of 1,3-bis(2,4,6-trimethylphenyl)-4,5-dihydroimidazolium tetrafluoroborate$^3$ 63 (0.031 g, 0.0792 mmol) in tetrahydrofuran (6 cm$^3$) under an atmosphere of nitrogen. The resultant suspension was stirred for 2 min then a solution of bis(tricyclohexylphosphine)benzylideneruthenium dichloride 64 (0.054 g, 0.066 mol) in dry benzene (6 cm$^3$) was added and the purple solution was heated at 80° C. for 35 min. The dark brown solution was cooled to room temperature and a solution of protected tripeptide 59 (0.155 g, 0.22 mmol) in dry benzene (85 cm$^3$) added and the mixture heated at 45° C. for 65 h. The solvent was removed in vacuo and the residue purified by chromatography (silica gel, hexane:ethyl acetate, 1:1, 1:2, 1:3, 1:4) to give the metathesis product 60 and unidentified product(s) (0.110 g) as a brown oil: [m/z (FAB+) 668.2982 (MH$^+$. C$_{38}$H$_{42}$N$_3$O$_8$ requires 668.2972]. The mixture was subsequently dissolved in methanol/water (4:1, 50 cm$^3$) and 10 wt. % palladium on activated carbon (0.035 g, 0.033 mmol) was added under an atmosphere of nitrogen. To the reaction flask was fitted a balloon of hydrogen and the mixture stirred for 17 h at room temperature. The reaction mixture was filtered through a pad of Celite™, washed with methanol/water (4:1, 100 cm$^3$) and concentrated in vacuo to yield a film (0.064 g) that was purified by RP HPLC [20% acetonitrile: 80% water (containing 0.05% trifluoroacetic acid)]. Repeated evaporation from a toluene/ether mixture and drying on a freeze drier gave 61 (0.045 g, 58% from 59) as an off white solid. 61 was shown to be a 65:35 trans:cis mixture of conformers by $^1$H NMR analysis (the ratio was estimated by integration of signals at δ 2.99 and 3.17-3.33 assigned to the 5-H atoms of the minor and major conformers respectively): mp 120-130° C.; [α]$_D$ –12.5 (c 0.104 in H$_2$O); δ$_H$ (300 MHz; D$_2$O), 1.24-2.68 (13.65H, m, 5-H$_A$H$_B$, 6-H$_2$, 7-H$_2$, 8-H$_2$, 9-H, 10-H$_2$, 15-H$_2$, 16-H$_2$), 2.99* (0.35H, dt, J 12.9 and 7.3, 5-H$_A$H$_B$), 3.17-3.33 (1H, m, 5-H), 3.40* (0.35H, d, J 15.6, 3-H$_A$H$_B$), 3.50-3.73 (2H, m, 17-H$_2$), 3.98* (0.35H, d, J 15.6, 3-H$_A$H$_B$), 4.01 (0.65H, d, J 15.6, 3-H$_A$H$_B$), 4.08 (0.65H, d, J 15.8, 3-H$_A$H$_B$), 4.44 (0.65H, dd, J 11.6 and 4.3, 11-H), 4.51 (0.65H, dd, J 7.5 and 5.0, 14-H) and 4.59-4.64* (0.7H, m, 11-H, 14-H); δ$_C$ (75 MHz; D$_2$O) 21.0, 21.4,* 21.7,* 22.2,* 23.6, 24.8, 25.2, 28.2, 31.2,* 31.3,* 31.6 (CH$_2$, 6-C, 7-C, 8-C, 10-C, 15-C, 16-C), 38.4* (CH, 9-C), 40.2 (CH, 9-C), 45.5* (CH$_2$, 3-C, 5-C), 46.9, 47.0 (CH$_2$, 17-C, 5-C), 47.5*, (CH$_2$, 17-C), 48.2, (CH$_2$, 3-C), 49.6 (CH, 11-C), 50.5* (CH, 11-C), 59.9* (CH, 14-C), 61.3 (CH, 14-C), 116.2 (q, J 291, CF$_3$), 162.6 (q, J 35.5, CF$_3$CO$_2$H), 164.4* (quat., 2-C), 164.9 (quat., 2-C), 173.4,* 173.4* (quat., 13-C, 11-CO), 173.4, 173.4 (quat., 13-C, 11-CO), 179.3* (quat., 9-CO) and 179.8 (quat., 9-CO); m/z (FAB+) 356.1829 [MH(free base)$^+$. C$_{16}$H$_{26}$N$_3$O$_6$ requires 356.1822]; [the minor component was tentatively assigned as glycyl-L-prolyl-L-γ-butylglutamic acid trifluoroacetate 62 and was shown to be a 78:22 trans:cis mixture of conformers by $^{13}$C NMR analysis (the ratio was estimated by integration of the signals at δ51.2 and 51.8 assigned to the Gluα-C atoms of the minor and major conformers respectively): mp 155-190° C. (dec.); $\delta_H$ (400 MHz; D$_2$O), 0.90 (3H, t, J 6.5, Gluγ-CH$_2$CH$_2$CH$_2$CH$_3$), 1.33 (4H, br s, Gluγ-CH$_2$CH$_2$CH$_2$CH$_3$), 1.64 (2H, br q, J 7.0, Gluγ-CH$_2$CH$_2$CH$_2$CH$_3$), 2.03-2.17 (5H, m, Gluβ-H$_2$, Proγ-H$_2$, Proβ-H$_A$H$_B$), 2.31-2.35 (0.78H, m, Pro13-H$_A$H$_B$), 2.57 (1H, p, J 6.9, Gluγ-H), 3.59-3.75 (2.18H, m, Proδ-H$_2$, Glyα-H$_A$H$_{B*}$), 3.98-4.10 (1.82H, Glyα-H$_2$, Glyα-H$_A$H$_{B*}$), 4.47 (1H, t, J 7.5, Gluα-H) and 4.51-4.56 (1H, m, Proα-H); $\delta_C$ (100 MHz; D$_2$O) 13.0 (CH$_3$, Gluγ-CH$_2$CH$_2$CH$_2$CH$_3$), 21.7 (CH$_2$, Gluγ-CH$_2$CH$_2$CH$_2$CH$_3$), 21.8* (CH$_2$, Gluγ-CH$_2$CH$_2$CH$_2$CH$_3$), 24.0 (CH$_2$, Proγ-C), 28.1 (CH$_2$, Gluγ-CH$_2$CH$_2$CH$_2$CH$_3$), 28.2* (CH$_2$, Gluγ-CH$_2$CH$_2$CH$_2$CH$_3$), 29.3 (CH$_2$, Proβ-C), 30.9 (CH$_2$, Gluγ-CH$_2$CH$_2$CH$_2$CH$_3$), 31.3*, 31.6*, 32.1* (CH$_2$), 32.3 (CH$_2$, GluβC), 40.1* (CH$_2$, Glyα-C), 40.3 (CH$_2$, Glyα-C), 42.0 (CH, Gluγ-C), 43.0* (CH, Gluγ-C), 46.8 (CH$_2$, Proδ-C), 47.4* (CH$_2$, Proδ-C), 51.2 (CH, Gluα-C), 51.8* (CH, Gluα-C), 59.9* (CH, Proα-C), 60.2 (CH, Proα-C), 115.5 (q, J 291, CF$_3$), 162.9 (q, J 35.2, CF$_3$CO$_2$H), 165.5 (quat., Gly-CO), 166.0* (quat., Gly-CO), 173.5* (quat., CO), 174.0 (quat., CO), 174.5* (quat., CO), 174.8 (quat., CO), 180.0 (quat., Gluγ-CO) and 180.2* (quat., Gluγ-CO); m/z (FAB+) 358.1978 [MH(free base)$^+$. C$_{16}$H$_{28}$N$_3$O$_6$ requires 358.1978].

Example 6

Synthesis of (2S, 9'R, 12'S)-2-{[(1',4'-Diaza-2'-oxobicyclo[7.3.0]-dodecyl)-12'-carbonyl]amino}-1,5-pentanedioic acid trifluoroacetate salt Scheme 1 Reagents, conditions and yields:

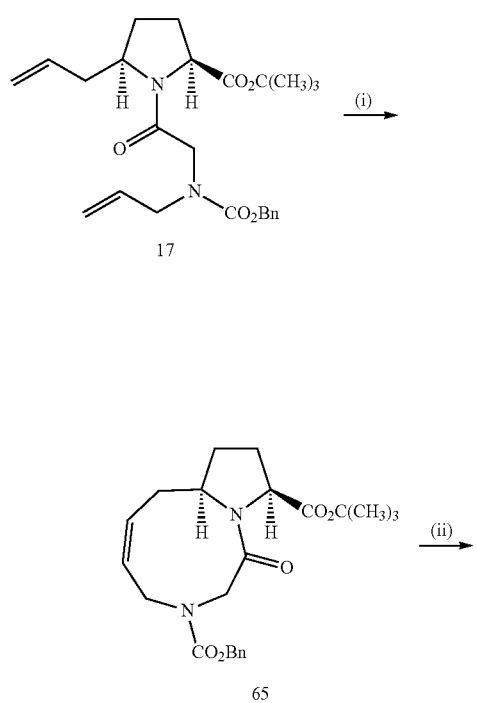

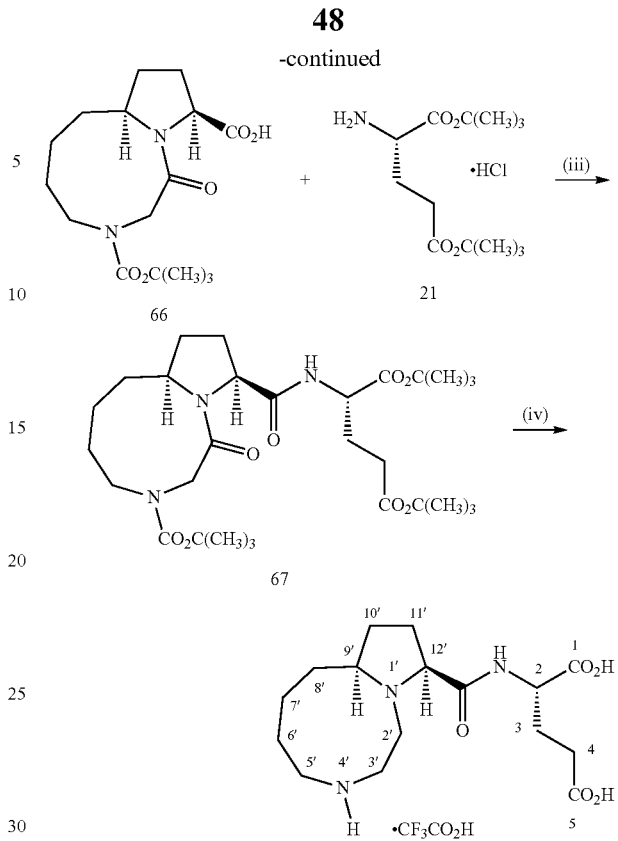

(i) Grubbs catalyst, CH$_2$Cl$_2$, reflux, 48 h, then DMSO, RT, 24 h (46%);
(ii) PtO$_2$, THF, H$_2$, RT, 16 h then 30% HBr/HOAc, RT, 2 h then NaHCO$_3$, H$_2$O, dixoane, Boc$_2$O, RT, 4 d (78%, 3 steps);
(iii) BoP-Cl, Et$_3$N, CH$_2$Cl$_2$, 0° C. to RT, 24 h (64%);
(iv) CF$_3$CO$_2$H, CH$_2$Cl$_2$, RT, 4 h (80%).

(6Z, 9R, 12S)-1,4-Diaza-4-benzyloxycarbonyl-12-tert-butoxycarbonyl-2-oxobicyclo[7.3.0]dodec-6-ene 65

To a degassed solution of diene 17 (0.11 g, 0.242 mmol) in dry dichloromethane (60 cm$^3$) was added bis(tricyclohexylphosphine)benzylidineruthenium dichloride (Grubbs's catalyst) (0.020 g, 0.024 mmol) under an atmosphere of nitrogen and the resultant purple solution heated at reflux for 24 h. Further bis(tricyclohexylphosphine)benzylidineruthenium dichloride (Grubbs's catalyst) (0.020 g, 0.024 mmol) was then added, and refluxing continued for a further 24 h. The solution was cooled to room temperature, dimethyl sulphoxide (0.16 cm$^3$, 2.26 mmol) was added and the orange/brown solution stirred for 22 h. The solvent was removed in vacuo and the residue purified by chromatography (SiO$_2$, hexanes-ethyl acetate, 3:1, 2:1, 1:1) to give an almost colourless oil which was further purified by chromatography (C$_{18}$RP silica, 100:0, 9:1, 9:3, 1:1, 1:9, water-acetonitrile,) to give alkene 65 (0.046 g, 46%) as a colourless oil. Alkene 65 existed exclusively as the trans C(O)—NPro conformer. In addition, restricted rotation about the N—CO carbamate bond was also observed resulting in a 1:1 mixture of conformers: [α]$_D$ −243.9 (c 0.27 in CH$_2$Cl$_2$); δ$_H$ (400 MHz; CDCl$_3$; Me$_4$Si) 1.49 [9H, s, C(CH$_3$)$_3$], 1.84-2.34 (5H, m, 8-H$_A$H$_B$, 10-H$_2$ and 11-H$_2$), 2.98-3.08 (1H, m, 8-H$_A$H$_B$), 3.69-3.88 (2H, m, 5-H$_A$H$_B$ and 3-H$_A$H$_B$), 4.0 (1H, p, J 7.6, 9-H), 4.33-4.61 (3H, m, 5-H$_A$H$_B$, 3-H$_A$H$_B$ and 12-H), 5.10-5.30 (2H, m, OCH$_2$Ph), 5.51-5.65 (1H, m, 6-H), 5.98-6.09 (1H, m, 7-H) and 7.29-7.38 (5H, m, Ph); δ$_C$ (100 MHz; CDCl$_3$) 27.2 (CH$_2$, 11-C), 28.0 [CH$_3$, C(CH$_3$)$_3$], 33.9 (CH$_2$, 8-C), 35.1 (CH$_2$, 10-C), 42.2 (CH$_2$, 5-C), 42.3 (CH$_2$, 5-C), 45.7 (CH$_2$, 3-C), 45.9 (CH$_2$, 3-C), 59.5 (CH, 9-C), 59.6 (CH, 9-C), 61.2 (CH, 12-C), 61.3 (CH, 12-C), 67.4 (CH$_2$, OCH$_2$Ph), 67.5 (CH$_2$, OCH$_2$Ph), 81.4 [quat., C(CH$_3$)$_3$], 81.5 [quat., C(CH$_3$)$_3$], 125.8 (CH, 6-C), 126.0 (CH, 6-C), 127.7 (CH, Ph), 127.8 (CH, Ph), 127.81 (CH, Ph), 127.9 (CH, Ph), 128.3 (CH, Ph), 132.0 (CH, 7-C), 132.4 (CH, 7-C), 136.5 (quat., Ph), 155.8 (quat., NCO$_2$), 156.2 (quat., NCO$_2$), 167.2 (quat., 2-C), 167.4 (quat., 2-C), 171.2 (quat., 12-CO) and 171.4 (quat., 12-CO); m/z (EI+) 414.2154 (M$^+$. C$_{23}$H$_{30}$N$_2$O$_5$ requires 414.2154).

(9R,12S)-1,4-Diaza-4-tert-butyloxycarbonyl-2-oxo-bicyclo[7.3.0]dodec-2-carboxylic acid 66

To a stirred solution of alkene 65 (0.12 g, 0.29 mmol) in tetrahydrofuran (4 cm$^3$) was added platinum oxide (0.0066 g, 0.029 mmol) under a flow of nitrogen. The mixture was hydrogenated (1 atm of H$_2$) for 16 h, filtered through Celite™, and the solvent removed in vacuo. The residue was dissolved in a solution of hydrobromic acid in acetic acid (30% w/w, 3 cm$^3$) and stirred at room temperature for 2 h. Removal of the volatiles in vacuo at 30° C. followed by addition and evaporation of methanol:water (3:1) several times yielded the hydrobromide salt which was dissolved in a solution of saturated sodium hydrogen carbonate (3 cm$^3$). Dioxane (2 cm$^3$) was then added and di-tert-butyl dicarbonate added to the opaque solution (0.076 g, 0.350 mmol). The resultant suspension was stirred for 24 h, di-tent-butyl dicarbonate (0.076 g, 0.3504 mmol), added and stirring continued for a further 72 h. Water (10 cm$^3$) was added, the solution washed with dichloromethane, and the aqueous layer acidified with 2 M aqueous hydrochloric acid and extracted with dichloromethane. The combined organic layers were dried (Na$_2$SO$_4$), filtered and the solvent removed to yield an oil (0.08 g) that was purified by chromatography (SiO$_2$, 2:1:0, 2:1:0.3, hexanes-ethyl acetate-acetic acid,) to give acid 66 (0.074 g, ca. 78%) as a colourless oil. Acid 66 existed exclusively as the trans C(O)—NPro conformer. In addition, restricted rotation about the N—CO carbamate bond was also observed resulting in a 1:1 mixture of conformers: δ$_H$ (400 MHz; CDCl$_3$; Me$_4$Si) 1.25-1.48 [11H, m, C(CH$_3$)$_3$, 8-H$_A$H$_B$ and 6-H$_A$H$_B$ or 7-H$_A$H$_B$], 1.54-1.82 (5H, m, 8-H$_A$H$_B$, 10-H$_A$H$_B$ and 6-H$_A$H$_B$ or 7-H$_A$H$_B$), 1.90-2.03 (1H, m, 10-H$_A$H$_B$), 2.10-2.33 (2H, m, 11-H$_2$), 2.78 (1H, td, J 12.7 and 2.6, 5-H$_A$H$_B$), 3.78-3.95 (2H, m, 5-H$_A$H$_B$ and 3-H), 4.20-4.30 (1H, m, 9-H), 4.52 (0.5H, d, J 17.7, 3-H$_A$H$_B$), 4.62 (1H, t, J 8.6, 12-H) and 4.76 (0.5H, d, J 17.2, 3-H$_A$H$_B$); δ$_C$ (100 MHz; CDCl$_3$) 22.2 (CH$_2$, 6-C or 7-C), 27.6 (CH$_2$, 6-C or 7-C), 24.3 (CH$_2$, 11-C), 24.8 (CH$_2$, 11-C), 26.8 (CH$_2$, 6-C or 7-C), 27.9 (CH$_2$, 6-C or 7-C), 28.3 [CH$_3$, C(CH$_3$)$_3$], 32.6 (CH$_2$, 10-C), 33.1 (CH$_2$, 10-C), 34.8 (CH$_2$, 8-C), 35.3 (CH$_2$, 8-C), 51.1 (CH$_2$, 5-C), 51.7 (CH$_2$, 5-C), 54.7 (CH$_2$, 3-C), 55.9 (CH$_2$, 3-C), 56.6 (CH, 9-C), 56.7 (CH, 9-C), 60.8 (CH, 12-C), 61.1 (CH, 12-C), 80.7 [quat., C(CH$_3$)$_3$], 154.8 (quat., NCO$_2$), 155.6 (quat., NCO$_2$), 170.0 (quat., 2-C), 170.5 (quat., 2-C), 174.1 (quat., 12-CO) and 174.7 (quat., 12-CO); m/z (FAB+) 327.1925 (MH$^+$. C$_{16}$H$_{27}$N$_2$O$_5$ requires 327.1920).

(2S, 9'S, 12'S)-Di-tert-butyl 2-{[(1',4'-diaza-4'-tert-butyloxycarbonyl-2'-oxobicyclo[7.3.0]dodecyl)-12'-carbonyl]amino}-1,5-pentanoate 67

Bis(2-oxo-3-oxazolidinyl)phosphinic chloride (BoP-Cl) (0.08 g, 0.31 mmol) was added to a solution of acid 66 (0.07 g, 0.20 mmol), L-glutamic acid di-tent-butyl ester hydrochloride 21 (0.085 g, 0.289 mmol) and triethylamine (0.084 cm$^3$, 0.60 mmol) in dichloromethane (7 cm$^3$) at 0° C. The mixture was stirred for 24 h, washed with saturated aqueous sodium hydrogen carbonate, 2 M aqueous hydrochloric acid, dried (Na$_2$SO$_4$), filtered and the solvent removed under reduced pressure. The resultant oil (0.141 g) was purified by chromatography (SiO$_2$, 1:1, 1:2, hexane-ethyl acetate) to afford amide 67 (0.077 g, ca. 64%) as a colourless oil. Amide 67 existed exclusively as the trans C(O)—NPro conformer. In addition, restricted rotation about the N—CO carbamate bond was also observed resulting in a 46:54 mixture of conformers: δ$_H$ (300 MHz; CDCl$_3$; Me$_4$Si) 1.14-1.30 [2H, m, 8'-H$_A$H$_B$ and H'-6(1H) or H'-7(1H)], 1.34-1.41 [27H, m, 3×C(CH$_3$)$_3$], 1.54-2.28 (11H, m, 8'-H$_A$H$_B$, 10'-H$_2$, 3-H$_2$, 4-H$_2$, 6'-H(3H) or 7'-H(3H)] and 11'-H$_A$H$_B$), 2.31-2.49 (1H, m, 11'-H$_A$H$_B$), 2.60-2.70 (1H, m, 5'-H$_A$H$_B$), 3.65-3.87 (2H, m, 5'-H$_A$H$_B$ and 3'-H$_A$H$_B$), 4.18 (1H, br s, 9'-H), 4.39 (1H, q, J 7.6, 2'-H), 4.48 (0.5H, d, J 17.5, 3'-H$_A$H$_B$), 4.65 (1H, t, J 7.8, 12'-H), 4.74 (0.5H, d, J 17.0, 3'-H$_A$H$_B$), 7.45 (0.46H, d, J 7.4, N—H), and 7.64 (0.54H, d, J 7.7, N—H); δ$_C$ (75 MHz; CDCl$_3$) 22.7 (CH$_2$, 11'-C), 23.3 (CH$_2$, 6'-C or 7'-C), 23.4 (CH$_2$, 6'-C or 7'-C), 27.0 (CH$_2$, 3-C, 6'-C or 7'-C), 27.7 (CH$_2$, 3-C, 6'-C or 7'-C), 27.8 (CH$_2$, 3-C, 6'-C or 7'-C), 28.2 (CH$_2$, 3-C, 6'-C or 7'-C), 27.9 [CH$_3$, C(CH$_3$)$_3$], 28.0 [CH$_3$, C(CH$_3$)$_3$], 28.4 [CH$_3$, C(CH$_3$)$_3$], 31.4 (CH$_2$, 4-C), 32.5 (CH$_2$, 10'-C), 32.8 (CH$_2$, 10'-C), 34.4 (CH$_2$, 8'-C), 35.1 (CH$_2$, 8'-C), 50.7 (CH$_2$, 5'-C), 51.5 (CH$_2$, 5'-C), 52.25 (CH, 2-C), 52.33 (CH, 2-C), 54.6 (CH$_2$, 3'-C), 55.0 (CH$_2$, 3'-C), 56.6 (CH, 9'-C), 56.8 (CH, 9'-C), 60.2 (CH, 12'-C), 60.8 (CH, 12'-C), 80.4 [quat., C(CH$_3$)$_3$], 80.6 [quat., C(CH$_3$)$_3$], 81.9 [quat., C(CH$_3$)$_3$], 154.7 (quat., NCO$_2$), 155.5 (quat., NCO$_2$), 169.4 (quat., 2'-C), 169.8 (quat., 2'-C), 170.6 (quat., 12'-CO, 1-C, 5-C), 170.8 (quat., 12'-CO, 1-C, 5-C) and 171.8 (quat., 12'-CO, 1-C, 5-C); m/z (FAB+) 568.3592 (MH$^+$. C$_{29}$H$_{50}$N$_3$O$_8$ requires 568.3598).

(2S, 9'S, 12'S)-2-{[(1',4'-Diaza-2'-oxobicyclo[7.3.0]dodecyl)-12'-carbonyl]amino}-1,5-pentanedioic acid trifluoroacetate 68

Amide 67 (0.072 g, 0.126 mmol) was dissolved in a mixture of dichloromethane and trifluoroacetic acid (5:2, v/v) and stirred at room temperature for 4 h. Evaporation of the volatiles, and subsequent purification by RP-HPLC [water (0.05% trifluoroacetic acid):acetonitrile, 90:10, 13 ml min$^{-1}$], gave 68 (0.059 g, 80%) as a white solid after drying on a freeze drier. Macrocycle 68 existed exclusively as the trans C(O)—NPro conformer: mpτ 30-130° C.; [α]$_D$ −36.9 (c 0.195 in MeOH); δ$_H$(400 MHz; CDCl$_3$; Me$_4$Si) 1.71-2.29 (11H, m, 6'-H$_2$, 7'-H$_2$, 10'-H$_2$, 3-H$_2$ and 11'-H$_A$H$_B$), 2.33-2.39 (1H, m, 11'-H$_A$H$_B$), 3.27 (1H, dt, J 10.2 and 4.1, 5'-H$_A$H$_B$), 3.39 (1H, td, J 12.0 and 2.2, 5% H$_A$H$_B$), 3.76 (1H, d, J 13.6, 3'-H$_A$H$_B$), 4.25-4.20 (2H, m, 3'-H$_A$H$_B$ and 9'-H), 4.45 (1H, dd, J 9.3 and 5.1, 2-H) and 4.51 (1H, dd, J 9.2 and 8.3, 12'-H); δ$_C$ (100 MHz; CDCl$_3$) 24.06 (CH$_2$, 6'-C or 7'-C), 24.1 (CH$_2$, 6'-C or 7'-C), 25.7 (CH$_2$, 3-C), 27.7 (CH$_2$, 11'-C), 29.6 (CH$_2$, 4-C), 32.5 (CH$_2$, 10'-C), 33.4 (CH$_2$, 8'-C), 43.3 (CH$_2$, 5'-C), 46.8 (CH$_2$, 3'-C), 51.8 (CH, 2-C), 61.9 (CH, 12'-C), 62.8 (CH, 9'-C), 116.2 (quat., q, J 290, CF$_3$), 162.6 (quat., q, J 35.2, CF$_3$CO$_2$H), 164.7 (quat., 2'-C), 173.4 (quat., 12'-CO), 174.6

(quat., 1-C), and 176.8 (quat., 5-C); m/z (FAB+) 356.1823 [MH(free base)+. $C_{16}H_{26}N_3O_6$ requires 356.1822].

Example 7

Synthesis of (2S, 3'S, 8'S, 11'S)-2{[(3'-Amino-1'-aza-2'-oxo-bicyclo[6.3.0]undecyl)-11'-carbonyl]amino}-1,5-pentanedioic acid trifluoroacetate salt

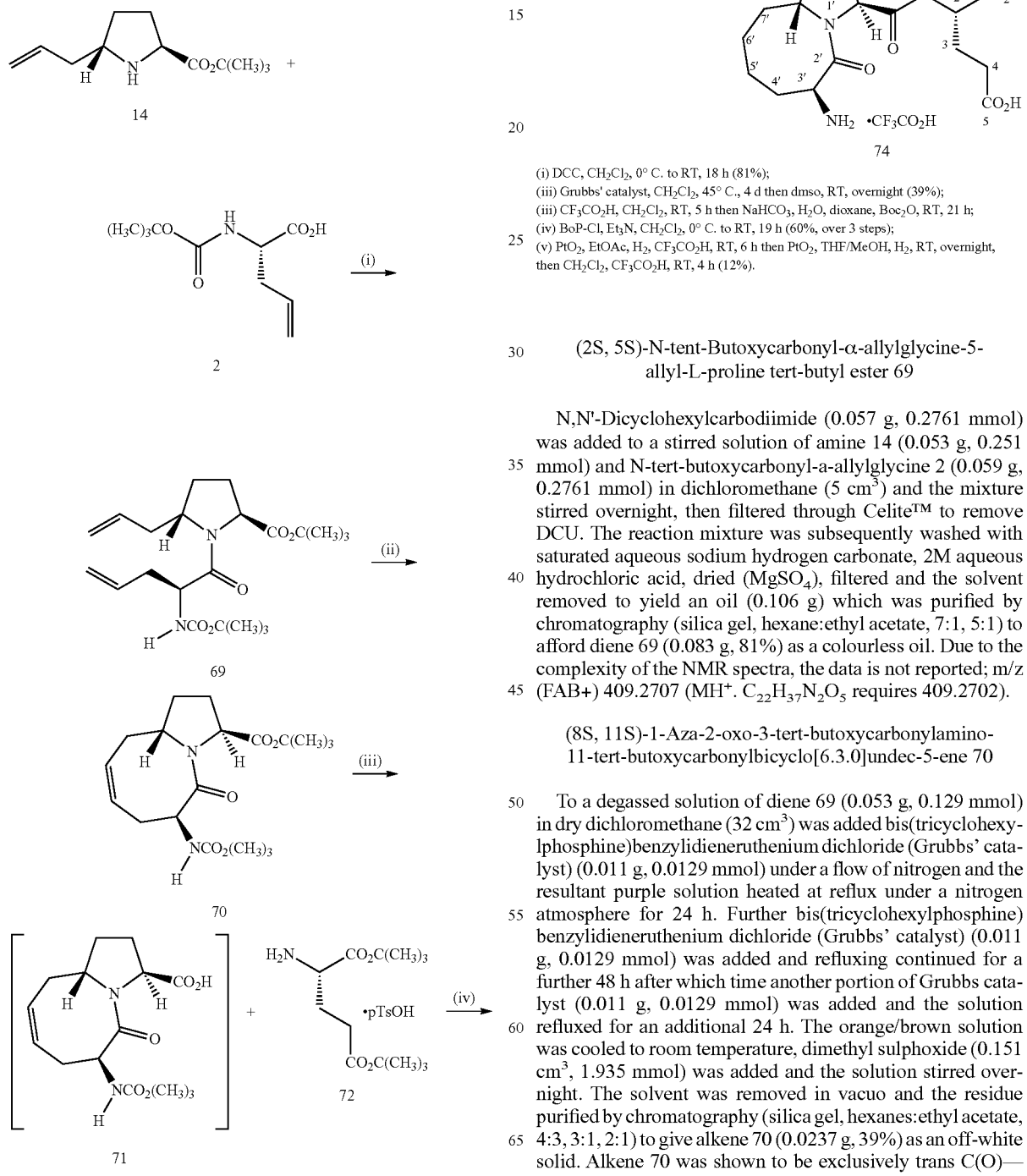

(i) DCC, $CH_2Cl_2$, 0° C. to RT, 18 h (81%);
(ii) Grubbs' catalyst, $CH_2Cl_2$, 45° C., 4 d then dmso, RT, overnight (39%);
(iii) $CF_3CO_2H$, $CH_2Cl_2$, RT, 5 h then $NaHCO_3$, $H_2O$, dioxane, $Boc_2O$, RT, 21 h;
(iv) BoP-Cl, $Et_3N$, $CH_2Cl_2$, 0° C. to RT, 19 h (60%, over 3 steps);
(v) $PtO_2$, EtOAc, $H_2$, $CF_3CO_2H$, RT, 6 h then $PtO_2$, THF/MeOH, $H_2$, RT, overnight, then $CH_2Cl_2$, $CF_3CO_2H$, RT, 4 h (12%).

(2S, 5S)-N-tent-Butoxycarbonyl-α-allylglycine-5-allyl-L-proline tert-butyl ester 69

N,N'-Dicyclohexylcarbodiimide (0.057 g, 0.2761 mmol) was added to a stirred solution of amine 14 (0.053 g, 0.251 mmol) and N-tert-butoxycarbonyl-a-allylglycine 2 (0.059 g, 0.2761 mmol) in dichloromethane (5 cm³) and the mixture stirred overnight, then filtered through Celite™ to remove DCU. The reaction mixture was subsequently washed with saturated aqueous sodium hydrogen carbonate, 2M aqueous hydrochloric acid, dried ($MgSO_4$), filtered and the solvent removed to yield an oil (0.106 g) which was purified by chromatography (silica gel, hexane:ethyl acetate, 7:1, 5:1) to afford diene 69 (0.083 g, 81%) as a colourless oil. Due to the complexity of the NMR spectra, the data is not reported; m/z (FAB+) 409.2707 (MH+. $C_{22}H_{37}N_2O_5$ requires 409.2702).

(8S, 11S)-1-Aza-2-oxo-3-tert-butoxycarbonylamino-11-tert-butoxycarbonylbicyclo[6.3.0]undec-5-ene 70

To a degassed solution of diene 69 (0.053 g, 0.129 mmol) in dry dichloromethane (32 cm³) was added bis(tricyclohexylphosphine)benzylidieneruthenium dichloride (Grubbs' catalyst) (0.011 g, 0.0129 mmol) under a flow of nitrogen and the resultant purple solution heated at reflux under a nitrogen atmosphere for 24 h. Further bis(tricyclohexylphosphine) benzylidieneruthenium dichloride (Grubbs' catalyst) (0.011 g, 0.0129 mmol) was added and refluxing continued for a further 48 h after which time another portion of Grubbs catalyst (0.011 g, 0.0129 mmol) was added and the solution refluxed for an additional 24 h. The orange/brown solution was cooled to room temperature, dimethyl sulphoxide (0.151 cm³, 1.935 mmol) was added and the solution stirred overnight. The solvent was removed in vacuo and the residue purified by chromatography (silica gel, hexanes:ethyl acetate, 4:3, 3:1, 2:1) to give alkene 70 (0.0237 g, 39%) as an off-white solid. Alkene 70 was shown to be exclusively trans C(O)—NPro conformer: mp 175-195° C.; $[α]_D$ −24.9 (c 0.237 in MeOH); $\delta_H$ (400 MHz; CDCl$_3$; Me$_4$Si) 1.45 [9H, s, C(CH$_3$)$_3$], 1.47 [9H, s, C(CH$_3$)$_3$], 1.68-1.74 (1H, m, 9-H$_A$H$_B$), 1.82 (1H, td, J 11.0 and 5.9, 10-H$_A$H$_B$), 2.17-2.26 (2H, m, 9-H$_A$H$_B$ and 10-H$_A$H$_B$), 2.27-2.40 (1H, br m, 7-H$_A$H$_B$), 2.49 (1H, br d, J 17.6, 7-H$_A$H$_B$), 2.55-2.63 (1H, m, 4-H$_A$H$_B$), 2.66 2.80 (1H, m, 4-H$_A$H$_B$), 4.40 (1H, dd, J 8.6 and 4.2, 11-H), 4.45-4.62 (2H, m, 3-H and 8-H), 5.62-5.68 (2H, m, H-6 and N—H) and 5.80-5.90 (1H, m, 5-H); $\delta_C$ (100 MHz; CDCl$_3$) 25.5 (CH$_2$, 10-C), 27.9 [CH$_3$, C(CH$_3$)$_3$], 28.3 [CH$_3$, C(CH$_3$)$_3$], 32.6 (CH$_2$, 4-C), 33.4 (CH$_2$, 7-C and 9-C), 55.8 (CH, 3-C), 57.2 (CH, 8-C), 61.5 (CH, 11-C), 79.5 [quat., C(CH$_3$)$_3$], 81.2 [quat., C(CH$_3$)$_3$], 128.6 (CH, 5-C and 6-C), 155.1 (quat., NCO$_2$), 169.6 (quat., 2-C) and 171.2 (quat., 11-CO); m/z (EI+) 380.2304 (M$^+$. C$_{20}$H$_{32}$N$_2$O$_5$ requires 380.2311).

(2S, 8'S, 11'S)-Di-tert-butyl 2-{[(1-Aza-2-oxo-3-tert-butoxycarbonylaminobicyclo[6.3.0]undec-5-ene)-11-carbonyl]amino}-1,5-pentanedioate 73

Alkene 70 (0.021 g, 0.055 mmol) was stirred at room temperature in dichloromethane:trifluoroacetic acid (3:1, v/v, 4 cm$^3$) for 5 h. Removal of the volatiles in vacuo yielded an oil that was dissolved in saturated aqueous sodium hydrogen carbonate (1.5 cm$^3$). Dioxane (1 cm$^3$) was added followed by di-tert-butyl dicarbonate (0.015 g, 0.066 mmol) and the milky suspension was stirred at room temperature for 21 h. The reaction was diluted with water until a solution was obtained and extracted with dichloromethane. The aqueous layer was acidified with 2M aqueous hydrochloric acid, extracted with dichloromethane and the combined organic extracts were dried (Na$_2$SO$_4$). Removal of the solvent in vacuo gave acid 71 (0.012 g) that was dissolved in dichloromethane (3 cm$^3$). Glutamic acid di-tert-butyl ester hydrochloride 72 (0.013 g, 0.044 mmol) was added and the solution cooled to 0° C. Triethylamine (0.013 cm$^3$, 0.092 mmol) and bis(2-oxo-3-oxazolidinyl)phosphinic chloride (BoP-Cl) (0.012 g, 0.048 mmol) were added and the mixture stirred for 19 h. The reaction mixture was washed with saturated aqueous sodium hydrogen carbonate, 2M aqueous hydrochloric acid, dried (Na$_2$SO$_4$) and the solvent removed to yield an oil (0.033 g) which was purified by chromatography (silica gel, hexane: ethyl acetate, 2:1, 1:1, 1:2) to afford amide 73 (0.0125 g, 60%, 3 steps) as a colourless oil: [$\alpha$]$_D$ +12.1 (c 0.247 in CH$_2$Cl$_2$); $\delta_H$ (400 MHz; CDCl$_3$; Me$_4$Si) 1.45-1.48 [27H, s, 3×C(CH$_3$)$_3$], 1.65-1.75 (1H, m, 9'-H$_A$H$_B$), 1.87 1.96 (1H, m, 3-H$_A$H$_B$), 2.02-2.41 (7H, m, 10'-H$_2$, 4-H$_2$, 3-H$_A$H$_B$, 9'-H$_A$H$_B$ and 7'-H$_A$H$_B$), 2.51 (1H, br d, J 17.4, 7'-H$_A$H$_B$), 2.57-2.64 (1H, m, 4'-H$_A$H$_B$), 2.70-2.80 (1H, m, 4'-H$_A$H$_B$), 4.39-4.48 (2H, m, 11'-H and 2-H), 4.52-4.62 (2H, m, 8'-H and 3'-H), 5.63-5.69 (1H, m, 6'-H), 5.78-5.84 (1H, m, 5'-H), 5.91 (1H, br s, N—H) and 6.73 (1H, d, J 7.0, N—H); $\delta_C$ (100 MHz; CDCl$_3$) 25.4 (CH$_2$, 10'-C), 27.2 (CH$_2$, 3-C), 27.9 [CH$_3$, C(CH$_3$)$_3$], 28.0 [CH$_3$, C(CH$_3$)$_3$], 28.3 [CH$_3$, C(CH$_3$)$_3$], 31.3 (CH$_2$, 4-C), 32.5 (CH$_2$, 5'-C), 33.3 (CH$_2$, 9'-C), 33.7 (CH$_2$, 7'-C), 52.3 (CH, 2-C), 56.3 (CH, 3'-C), 57.8 (CH, 8'-C), 61.9 (CH, 11'-C), 79.7 [quat., C(CH$_3$)$_3$], 80.6 [quat., C(CH$_3$)$_3$], 82.0 [quat., C(CH$_3$)$_3$], 127.9 (CH, 5'-C), 128.6 (CH, 6'-C), 155.4 (quat., NCO$_2$), 170.4 (quat., 2'-C), 170.8 (quat., CO), 171.7 (quat., CO) and 172.6 (quat., CO);

(2S, 3'S, 8'S, 11'S)-2{[(3'-Amino-1'-aza-2'-oxo-bicyclo[6.3.0]undecyl)-11'-carbonyl]amino}-1,5-pentanedioic acid trifluoroacetate salt 74

PtO$_2$ (0.001 g, 0.0042 mmol) was added to a stirred solution of amide 73 (0.012 g, 0.021 mmol) in ethyl acetate: trifluoroacetic acid (5:3, v/v, 8 cm$^3$) under a nitrogen atmosphere. The mixture was hydrogenated (1 atm. of hydrogen) overnight, filtered through Celite™, and the solvent removed in vacuo. NMR and HPLC analysis showed the reaction to be incomplete (both double bond and protecting groups remaining). Thus PtO$_2$ (0.0003 g, 0.0126 mmol) was added to a stirred solution of the residue in tetrahydrofuran:methanol (1:1, v/v, 2 cm$^3$) under a nitrogen atmosphere. The mixture was hydrogenated (1 atm. of hydrogen) overnight, filtered through Celite™, and the solvent removed in vacuo. The residue was dissolved in dichloromethane (3 cm$^3$), trifluoroacetic acid (1 cm$^3$) added and the solution stirred for 4 h at room temperature. Removal of the volatiles in vacuo, purification by RP HPLC [90% water (containing 0.05% trifluoroacetic acid):10% acetonitrile, 13 ml min$^{-1}$] and drying on a freeze drier gave 74 (1.4 mg 12%, from 73) as a thin film. Due to the small amount of sample obtained an optical rotation was not recorded: $\delta_H$ (400 MHz; D$_2$O) 1.74-2.42 (14H, m, 5'-H$_2$, 6'-H$_2$, 4'-H$_2$, 9'-H$_2$, 3-H$_2$, 7'-H$_2$ and 10'-H$_2$), 2.52 (2H, t, J 8.8, 4-H$_2$), 4.3-4.4 (1H, m, 2H), 4.43-4.5 (1H, m) and 4.62-4.69 (1H, m); $\delta_C$ (100 MHz; D$_2$O) 22.3 (CH$_2$), 25.4 (CH$_2$), 28.4 (CH$_2$), 29.0 (CH$_2$), 30.2 (CH$_2$), 32.4 (CH$_2$), 33.7 (CH$_2$), 53.9 (CH), 55.1 (CH), 60.2 (CH), 62.8 (CH), 168.1 (quat., CO) and 173.7 (quat., CO); Note: due to small amount of sample 2 quaternary carbons and trifluoroacetate signals not detected; m/z (FAB+) 356.1816 [MH(free base)$^+$. C$_{16}$H$_{26}$N$_3$O$_6$ requires 356.1822].

In Vitro Testing

The following Examples are provided to demonstrate features of this invention. They are not intended to be limiting, and other compositions and methods of this invention can be developed without undue experimentation. All of those compositions and methods are considered to be part of this invention. All references cited herein are incorporated fully by reference.

All the following experiments were carried out using protocols developed under guidelines approved by the University of Auckland Animal Ethics Committee.

Example 8

Effects of Cyclic G-2AllylP on Cerebellar Cell Explants

To determine the effects of the compounds of the invention on neuronal cells in vitro, a series of studies was carried out using cerebellar explants from adult rats. In vitro systems are suitable for studying neuronal proliferation, neurite growth, formation of nerve bundles and effects of toxins on neural cells, effects that parallel effects observed in vivo. Thus, results of studies using in vitro cerebellar explants are predictive of effects of interventions in vivo.

In a first series of studies, effects of glutamate on cerebellar explants were determined. At physiological concentrations, glutamate is a neurotransmitter in the CNS of mammals, including humans. However, at sufficiently high concentrations, glutamate is neurotoxic, resulting in neuronal cell death. Because glutamate is a naturally occurring neurotransmitter in the CNS of mammals, including humans, and because glutamate neurotoxicity is recognized in the art as reflective of neurotoxicity in general, and including cell death and degeneration, it is a valuable tool useful for identifying and characterizing agents effective in treatment of neurodegeneration and neural cell death.

Materials and Methods

Cover slips were placed into a large Petri dish and washed in 70% alcohol for 5 minutes, then washed with Millipore H₂O. The cover slips were air dried, and coated with Poly-D-Lysine (1 mg/ml stock solution in PBS, 90-100 µl) for 2 hours at 34° C.

Extraction of Cerebellar Tissue

Postnatal day 8 Wistar rats were used for the study. The rats were sacrificed and placed in ice for 1 minute, decapitated and the cerebellum removed and placed on ice. Cerebellum tissue was placed in 1 ml of 0.65% glucose-supplemented PBS (10 µl 65% stock D (+)glucose/1 ml PBS) in a large Petri dish, chopped up into smaller sections and triturated with a 1 ml insulin syringe via a 23 G (0.4 mm) needle, and then squirted back into the glucose solution in the large Petri dish. The tissue was sieved through (125 µm pore size gauze) and centrifuged (2 minutes at 60 g) twice to exchange the medium into serum-free BSA-supplemented START V medium (Biochrom, Germany). The second centrifugation step was done with 1 ml of START V medium. The microexplants were reconstituted into 500 µl of START V medium and put on ice.

Cultivation of Cerebellar Cells

Two hours after PDL-coating, the slides were washed with Millipore H₂O and air dried. Each slide was placed into a small Petri dish (diameter: 35 mm) and 40 µl of START V/cell suspension was added. The tissue was incubated for 2 hours at 34° C. (settlement period). START V-medium (1 ml) was then added to the Petri dish and cultivated at 34° C. in the presence of 5% CO₂ in air at 100% humidity for 48 hours.

Drug Application

For the study, certain explant cultures were exposed to vehicle (PBS) only. In the first study (Study 1) 10 µl of toxin 1 (L-glutamate-100 mM in Millipore water; final concentration: 1 mM) and 10 µl of toxin 2 (3-nitropropionic acid-50 mM- pH 7- in Millipore water, final concentration: 0.5 mM) was applied simultaneously with the compounds to be tested (10 mM stock solution prepared in PBS and diluted to final concentrations between 1-100 nM). In each case, the drugs were left in contact with the explants for the duration of the study.

Methods for Determining Drug Effects

After explants were exposed to drugs for the study period, cells were then rinsed in PBS and then fixed in increasing concentrations of paraformaldehyde (5000 of 0.4% PFA was applied; then 1.2% PFA; then 3% PFA and finally 4% PFA (each fixation step: 2-3 minutes). Finally, the microexplants were rinsed in PBS.

Neurons in the explants were then evaluated for morphology (presence of neurites) and counted as live cells per microscopic field. Four fields displaying highest cell density were counted per cover slip and the data presented as mean±standard error of the mean (SEM); n=4 each. Statistical significance was evaluated by using the non-paired Student's t-test.

Results

Figure 2:
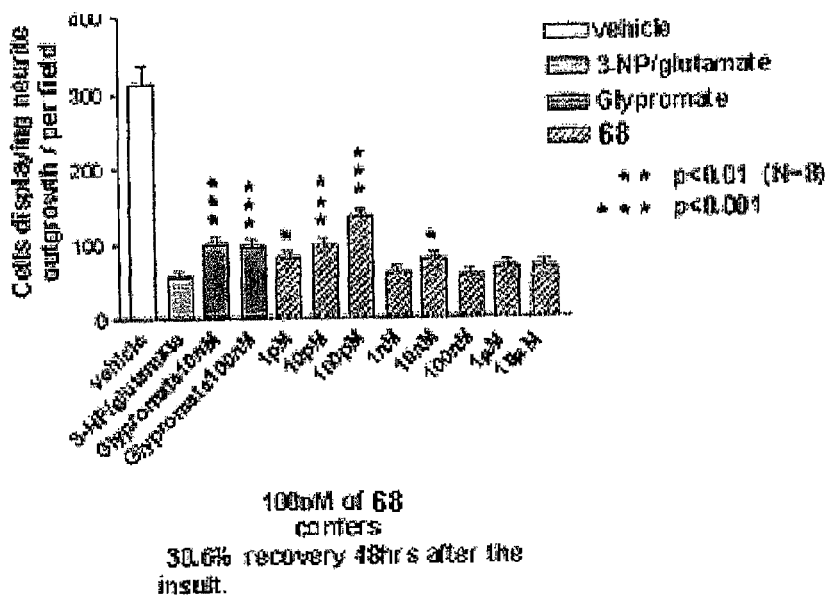
FIG. 2 is a graph showing effects of (2S, 9'S, 12'S)-2-{[(1', 4'-Diaza-2'-oxobicyclo[7.3.0]dodecyl)-12'-carbonyl] amino}-1,5-pentanedioic acid trifluoroacetate 68 on neuronal survival in animals following excitotoxic oxidative stress.

The results of the study are shown in FIG. 1 and FIG. 2. Glutamate treatment (1 mM) resulted in about an 80% loss of cerebellar neurons having neurites compared to vehicle-treated controls. In contrast, administration of (2S, 3'S, 8'R, 11'S) 2-{[(3'-Amino-1'-aza-2'-oxobicyclo[6.3.0]-undecyl)-11'-carbonyl]amino}-1,5-pentanedioic acid trifluoroacetate salt 48 and (2S, 9'S, 12'S)-2-{[(1',4'-Diaza-2'-oxobicyclo[7.3.0]dodecyl)-12'-carbonyl]amino}-1,5-pentanedioic acid trifluoroacetate 68 (FIGS. 1 and 2 respectively) significantly increased the numbers of cells having neurites in a dose-dependent manner when administered simultaneously with glutamate. Treatment with (2S, 3'S, 8'R, 11'S) 2-{[(3'-Amino-1'-aza-2'-oxobicyclo[6.3.0]-undecyl)-11'-carbonyl]amino}-1,5-pentanedioic acid trifluoroacetate salt 48 and (2S, 9'S, 12'S)-2-{[(1',4'-Diaza-2'-oxobicyclo[7.3.0]dodecyl)-12'-carbonyl]amino}-1,5-pentanedioic acid trifluoroacetate 68 (FIGS. 1 and 2 respectively) showed a significant recovery from glutamate-induced neurotoxicity.

Conclusions

Treatment with (2S, 3'S, 8'R, 11'S) 2-{[(3'-Amino-1'-aza-2'-oxobicyclo[6.3.0[-undecyl)-11'-carbonyl]amino}-1,5-pentanedioic acid trifluoroacetate salt 48 and (2S, 9'S, 12'S)-2-{[(1',4'-Diaza-2'-oxobicyclo[7.3.0]dodecyl)-12'-carbonyl]amino}-1,5-pentanedioic acid trifluoroacetate 68 prevented glutamate-induced neurotoxicity, indicating that (2S, 3'S, 8'R, 11'S) 2-{[(3'-Amino-1'-aza-2'-oxobicyclo[6.3.0]-undecyl)-11'-carbonyl]amino}-1,5-pentanedioic acid trifluoroacetate salt 48 and (2S, 9'S, 12'S)-2-{[(1',4'-Diaza-2'-oxobicyclo[7.3.0]dodecyl)-12'-carbonyl]amino}-1,5-pentanedioic acid trifluoroacetate 68 are neuroprotective and can be used to reverse and/or inhibit neuronal degeneration or cell death.

Example 9

Hypoxic-Ischemic Injury

Materials and Methods

To determine whether compounds of the invention might prevent neuronal injury in response to stroke, cardiac arterial bypass graft surgery (CABG) or other hypoxic insults, a series of studies were carried out in rats that had been exposed to hypoxic-ischemic injury (HI). Adult rats (Wistar, 280-310 g, male) were used. The modified Levine model preparation and experimental procedures were used (Rice et al, 1981, *Ann. Neurol.*: 9: 131-141; Guan et al J., 1993, *Cereb. Blood Flow Metab.*: 13(4): 609-16). These procedures in brief, consist of an HI injury induced by unilateral carotid artery ligation followed by inhalational asphyxia in the animals with an implanted lateral ventricular cannula. A guide cannula was stereotaxically placed on the top of the dura 1.5 mm to the right of the mid-line and 7.5 mm anterior to the interaural zero plane under halothane anaesthesia. The right carotid artery was double ligated two days after the cannulation. After 1 hour recovery from the anaesthesia, each of the rats were placed in an incubator where the humidity (90±5%) and temperature (31°±0.5° C.) were controlled for another hour, then exposed to hypoxia (6% oxygen) for 10 min. The animals were kept in the incubator for an additional 2 hours before treatment.

Pairs of rats were treated intracerebral ventricularly (icv) with either (2S, 9'S,12'S)-2-{[(1',4'-Diaza-2'-oxobicyclo[7.3.0]dodecyl)-12'-carbonyl]amino}-1,5-pentanedioic acid trifluoroacetate (68) (100 pM) or vehicle (normal saline) 2 hours after hypoxic-ischemic insult. Rats in each group were simultaneously infused with (2S, 9'S, 12'S)-2-{[(1',4'-Diaza-2'-oxobicyclo[7.3.0]dodecyl)-12'-carbonyl]amino}-1,5-pentanedioic acid trifluoroacetate (68) or vehicle under light anaesthesia (1.5% halothane) 2 hours after the insult. A total volume of 20µl was infused (icv) over 20 minutes by a microinfusion pump.

Histological examination was performed on rats 5 days after the hypoxic-ischemic injury. The rats were killed with an overdose of sodium pentobarbital and were perfused transcardially with normal saline followed by 10% formalin. The brains were kept in the same fixative for a minimum of 2 days before being processed using a standard paraffin imbedding procedure.

Coronal sections 8 µm in thickness were cut from the striatum, cerebral cortex and hippocampus and were stained with thionin and acid fuchsin. The histological outcome was assessed at three levels: (1) the mid level of the striatum, (2)

where the completed hippocampus first appeared and (3) the level where the ventral horn of the hippocampus just appears. The severity of tissue damage was scored in the striatum, cortex and the CA1-2, CA3, CA4 and dentate gyrus of the hippocampus. Tissue damage was identified as neuronal loss (acidophilic (red) cytoplasm and contracted nuclei), pannecrosis and cellular reactions. Tissue damage was scored using the following scoring system: 0: tissue showed no tissue damage, 1: <5% tissue was damaged, 2: <50% tissue was damaged, 3: >50% tissue was damaged and 4: >95% tissue was damaged.

RESULTS AND CONCLUSION

Figure 3:
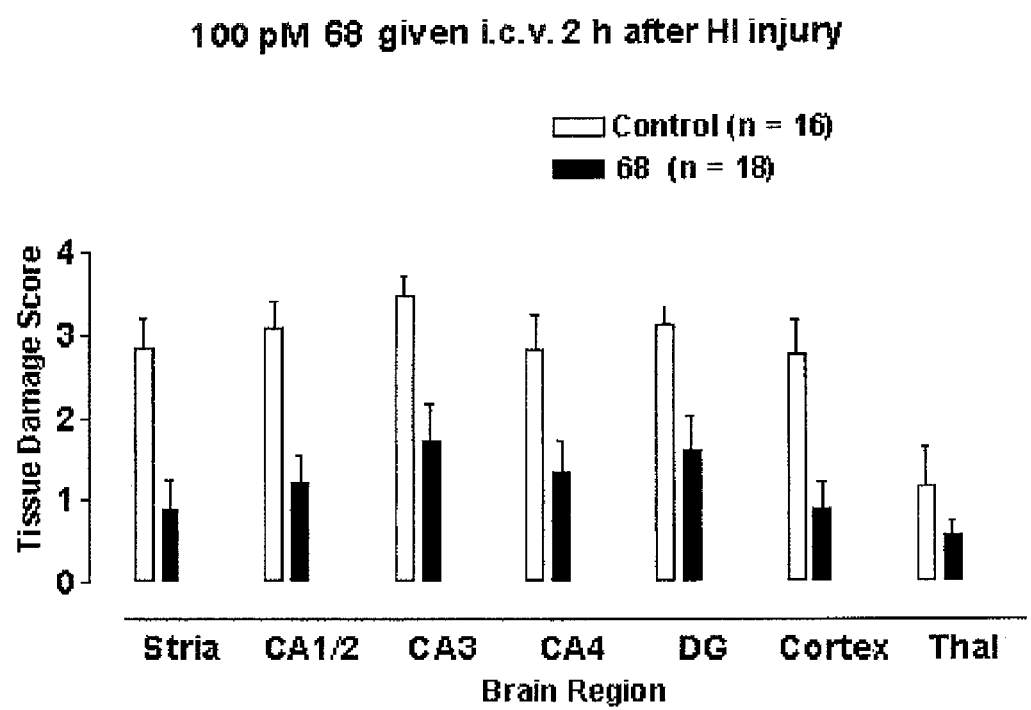
FIG. 3 is a graph showing the neuroprotective effects of (2S, 9'S, 12'S)-2-{[(1',4'-Diaza-2'-oxobicyclo[7.3.0]dodecyl)-12'-carbonyl]amino}-1,5-pentanedioic acid trifluoroacetate 68 in a global model of brain ischaemia.

The results of this study are shown in FIG. 3. FIG. 3 shows that hypoxic-ischemic injury (left bars of each set) resulted in significant damage scores in each of the areas of the brain studied. FIG. 3 also shows that central administration of a relatively low dose of (2S, 9'S, 12'S)-2-{[(1',4'-Diaza-2'-oxo-bicyclo[7.3.0]dodecyl)-12'-carbonyl]amino}-1,5 pentanedioic acid trifluoroacetate (68) (right bars of each set; 100 pM) significantly reduced the tissue damage in each brain region examined compared to the vehicle treated group (p<0.001).

It can be seen that (2S, 9'R, 12'S)-2-{[(1',4'-Diaza-2'-oxo-bicyclo[7.3.0]dodecyl)-12'-carbonyl]amino}-1,5-pentanedioic acid trifluoroacetate (68) can be neuroprotective against neural damage caused by hypoxic-ischemic injury, even when administered after hypoxic-ischemic injury. This surprising finding indicates that (2S, 9'S, 12'S)-2-{[(1',4'-Diaza-2'-oxobicyclo[7.3.0]dodecyl)-12'-carbonyl]amino}-1, 5-pentanedioic acid trifluoroacetate (68) is a useful agent to treat a variety of conditions characterized by neural degeneration or cell death.

What is claimed is:
1. A compound having the formula:

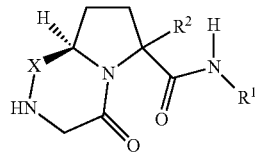

or a pharmaceutically acceptable salt thereof, wherein:
$R^1 =$ —CH(COOH)—$(CH_2)_2$—COOH;
$R^2 =$ H; and
$X =(CH_2)_4$.

2. A compound having the structure:

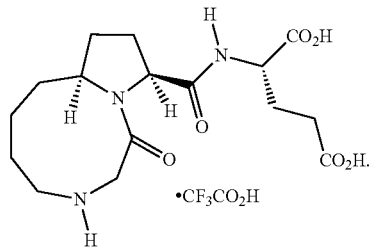

* * * * *